(12) United States Patent
Han

(10) Patent No.: US 11,285,103 B2
(45) Date of Patent: Mar. 29, 2022

(54) DEGRADABLE HYDROGEL UNDER PHYSIOLOGICAL CONDITIONS

(71) Applicant: Jie Han, Suzhou (CN)

(72) Inventor: Jie Han, Suzhou (CN)

( * ) Notice: Subject to any disclaimer, the term of this patent is extended or adjusted under 35 U.S.C. 154(b) by 85 days.

(21) Appl. No.: 16/063,687

(22) PCT Filed: Dec. 19, 2016

(86) PCT No.: PCT/CN2016/110876
§ 371 (c)(1),
(2) Date: Jun. 18, 2018

(87) PCT Pub. No.: WO2017/101883
PCT Pub. Date: Jun. 22, 2017

(65) Prior Publication Data
US 2020/0268658 A1    Aug. 27, 2020

(30) Foreign Application Priority Data

Dec. 18, 2015 (CN) .......................... 201510953277.0

(51) Int. Cl.
| | | |
|---|---|---|
| *A61K 38/26* | (2006.01) | |
| *A61K 38/28* | (2006.01) | |
| *A61K 47/60* | (2017.01) | |
| *A61K 47/69* | (2017.01) | |
| *A61K 9/06* | (2006.01) | |

(52) U.S. Cl.
CPC ................ *A61K 9/06* (2013.01); *A61K 38/26* (2013.01); *A61K 38/28* (2013.01); *A61K 47/60* (2017.08); *A61K 47/6903* (2017.08)

(58) Field of Classification Search
CPC ...... A61K 9/06; A61K 47/6903; A61K 47/60; A61K 38/26; A61K 38/28
See application file for complete search history.

(56) References Cited

U.S. PATENT DOCUMENTS

| | | | |
|---|---|---|---|
| 3,313,765 A | * | 4/1967 | Roberts |
| 3,671,644 A | * | 6/1972 | Irani |
| 2012/0156259 A1 | * | 6/2012 | Rau et al. |
| 2015/0246958 A1 | | 9/2015 | Han |

FOREIGN PATENT DOCUMENTS

| | | |
|---|---|---|
| CN | 102573913 | 7/2012 |
| CN | 103945870 | 7/2014 |
| WO | WO-2010/059883 | 5/2010 |
| WO | WO-2013/036847 | 3/2013 |

OTHER PUBLICATIONS

International Preliminary Report on Patentability for International Application No. PCT/CN2016/110876 dated Jun. 19, 2018. (5 pages).
International Search Report and Written Opinion for International Application No. PCT/CN2016/110876 dated Mar. 16, 2017. (16 pages).
Peng et al., "Synthesis and Characterization of a Novel Biodegradable Amphoteric pH-sensitive Hydrogel", Materials Review, 2010, vol. 24, No. 7, pp. 48-51, Abstract.

* cited by examiner

*Primary Examiner* — Alma Pipic
(74) *Attorney, Agent, or Firm* — Sheppard Mullin Richter & Hampton LLP

(57) ABSTRACT

The present invention discloses a hydrogel that can be degraded under physiological conditions. The hydrogel includes at least one backbone moiety and an optional crosslinking moiety, and biodegradable linkers connecting backbone moieties and crosslinking moieties can be degraded by intramolecular cyclization.

19 Claims, 1 Drawing Sheet
Specification includes a Sequence Listing.

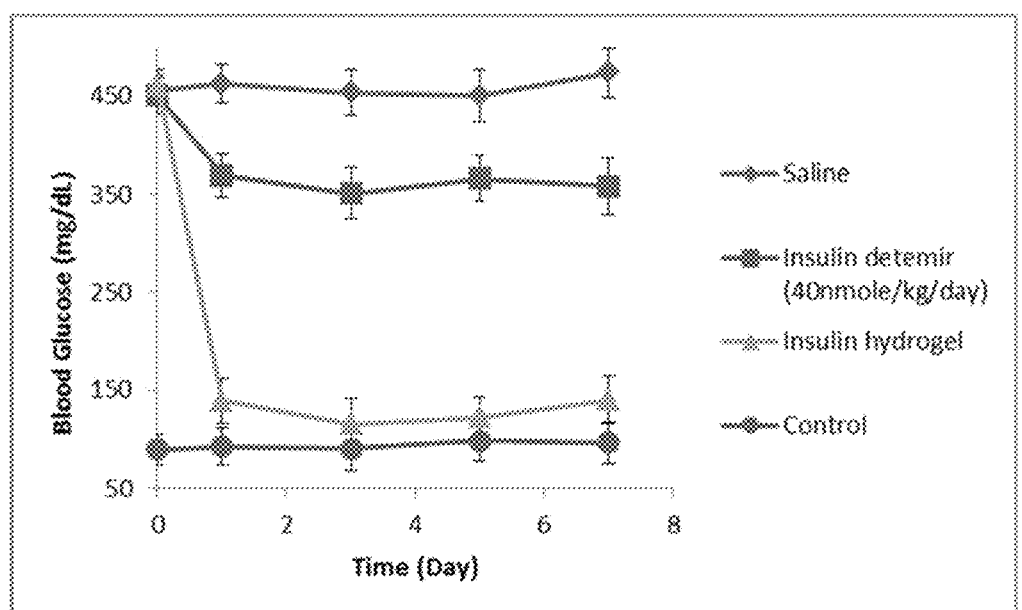

DEGRADABLE HYDROGEL UNDER PHYSIOLOGICAL CONDITIONS

CROSS-REFERENCE TO RELATED APPLICATIONS

This application is a U.S. National Stage Application under 35 U.S.C. § 371 of International Application No. PCT/CN2016/110876, filed Dec. 19, 2016, which application claims the benefit of Chinese Application No. 201510953277.0, filed Dec. 18, 2015, each of which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Mar. 22, 2021, is named 60SG_274657_US_ST25.txt and is 1,276 bytes in size.

FIELD

The present invention relates to the field of biological engineering, in particular, relates to a hydrogel which can be degraded under physiological conditions.

BACKGROUND ART

Hydrogels are promising materials for drug delivery systems. The high water content of hydrogels renders the material biocompatible and minimizes inflammation reactions of tissue in contact with the hydrogels. While hydrogels can be used for both small molecule and macromolecule drugs, hydrogels provide a well-hydrated environment particularly suitable for activity and structural integrity of peptide, protein, oligonucleotide or polynucleotide drugs.

Hydrogels loaded with biologically active substances may be administered to a patient to form a depot in vivo and provides a sustained release of biologically active substances over a desired length of time. In accordance with the connection between a hydrogel and a biologically active substance two different approaches for the preparation of hydrogel-based depots are known in the art, non-covalent depots and covalent depots.

In the non-covalent approach, biologically active substances such as drugs are encapsulated physically without chemical linkage to the hydrogel. In this approach, the average pore size in the three-dimensional network of the hydrogel has to be smaller than the size of the biologically active substance for efficient encapsulation by the hydrogel. Therefore, a biologically active substance cannot be incorporated into the hydrogel after hydrogel formation. In the non-covalent approach, hydrogels have to be chemically crosslinked in the presence of biologically active substances or pores have to be formed through physical crosslinks in a self-assembly process also in the presence of biologically active substances. The hydrogels can be prepared by crosslinking hydrophilic biopolymers or synthetic polymers. Examples of the hydrogels formed from physical or chemical crosslinking of hydrophilic biopolymers, include but are not limited to, hyaluronans, chitosans, alginates, collagen, dextran, pectin, carrageenan, polylysine, gelatin or agarose. Examples of hydrogels formed by chemically or physically cross-linked synthetic polymers include polyethylene glycol, polypropylene glycol, poly (lactic acid-ethylene glycol copolymer) acid (PLGA) polymer. In non-covalent depots, pore size of three-dimensional network in hydrogels is gradually enlarged with hydrogel degradation and the encapsulated biologically active substance is thus liberated.

In covalent approach, biologically active substances are attached to hydrogels by reversible or biodegradable linkers.

Whether it is a non-covalent or covalent depot, the majority of existing hydrogels depends on enzymatic catalysis for degradation. Enzyme levels and specificities vary greatly among patients and even in the same patient in different health conditions, and depend on the tissue chosen injection point and other difficult-to-control parameters. The difference between actual and expected dosage has an impact on the therapeutic outcome and the side effects of drugs with low therapeutic index is magnified.

Another complication lies in the fact that polymer degradation under in vivo conditions may also occur chemically. Ester bonds typically employed as biodegradable bonds may spontaneously hydrolyze at the physiological pH of 7.4 in plain buffer in the absence of enzymes. Many hydrogels are composed of a large amount of ester bonds in order to effect efficient release of biologically active substances. Both the high local concentration of ester bonds and the tight encapsulation of biologically active substances may lead to side reactions. It is possible that an amino group present in the biologically active substance may be positioned in proximity to an ester group, with the amino group providing a nucleophile effecting ester cleavage and subsequent amidation. This process results in a very stable amide linkage between the biologically active substance and the polymer. The biologically active substance will not be released until the polymer chain to which the biologically active substance is attached is degraded, and the biologically active substance will be permanently modified. Such modifications are known to reduce potency and specificity of the biologically active substance and may also cause side effects. In addition, this undesirable modification process is largely uncontrolled and gives rise to a variety of molecular species.

After the completion of the therapy, hydrogels need to be cleared from the body. Surgical removal of hydrogels tends to increase the suffering of patients. Although some of the known hydrogels claim to be theoretically biodegradable, in practice the degradation is uncontrolled and thus unpredictable.

SUMMARY OF THE INVENTION

The present invention introduces biodegradable linkers inside a hydrogel backbone moiety or in a crosslinkable moiety between hydrogel backbone moieties. These biodegradable linkers are capable of being automatically cleaved by chemical reactions under physiological conditions (eg, 37° C., pH 7.0-7.6) at a rate that depends on temperature and pH and does not require the aid of enzymes or other reagents. Since physiological conditions are generally constant in the human population, this new type of hydrogel is biodegradable at a predetermined rate and the variation is de minimus intra and interpatiently. More consistent therapeutic effect can be produced. In addition, this new type of hydrogel can be completely degraded into small molecular weight fragments that are cleared from the body and does not accumulate at the injection site or in the body. The present invention provides a hydrogel which is degraded non-enzymatically under physiological conditions into water soluble, smaller molecular weight components, and methods for preparing said hydrogels. Backbone moieties or crosslinking moieties of hydrogels comprise biodegradable linkers, which be cleaved under biological conditions, resulting in degradation of the hydrogels. The present invention further relates to a biodegradable linker groups themselves, and intermediates in the synthesis process of the present invention.

Biodegradable linkers of the present invention comprise moieties that can be automatically cleaved under physiological conditions and also comprise reactive groups that forme covalent bonds with reactive polymers. A reactive polymer in the present invention may be a hydrogel backbone moiety or a crosslinkable moiety. The moiety which is automatically cleaved under physiological conditions has the following formula

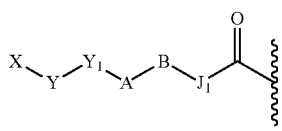

X, Y, $Y_1$, A, B, $J_1$ are defined in detail hereinafter. Y, A, and B contain at least one reactive group which can form a covalent bond with the reactive polymer. The wavy line indicates the attachment point of an amide bond or an ester bond formed between a biodegradable linker and a biologically active substance or a reactive polymer. Biodegradable linkers connect two or more reactive polymers.

The hydrogels prepared according to the present invention may be applied to different fields such as drug delivery systems and biomedical engineering.

The hydrogels prepared according to the present invention may further comprise one or more pharmaceutically or biologically active substances. One or more drugs or biologically active substances may be encapsulated inside a hydrogel by physical means rather than by chemical bonds. A drug or a biologically active substance may be connected to one end of a biodegradable linker, and the other end of the biodegradable linker may be coupled to the hydrogel. After cleavage of the biodegradable linker a drug or a biologically active substance can be released independently without depending on the degradation of the hydrogel. The present invention also provides methods for preparing biodegradable hydrogels, wherein the drug release rate and hydrogel degradation rate are controllable.

BRIEF DESCRIPTION OF DRAWINGS

FIG. 1 illustrates weekly blood glucose change after the diabetic rats were given saline, insulin detemir and insulin hydrogels.

DETAILED DESCRIPTION OF THE INVENTION

The hydrogel of the present invention is a polymer that is crosslinked by linkers which are biodegradable under physiological conditions. At physiological pH and temperature, these hydrogels lose structural integrity after cleavage of crosslinkers, resulting in formation of fragments that are sufficiently small and soluble, and thus undergo clearance from the system through the usual physiological pathways.

Unless otherwise indicated, the following definitions of terms apply throughout this patent. Terms not defined herein have the meaning as commonly understood in the relevant literature.

In the present invention, "a biologically active substance" refers to a therapeutic or pharmacological substance. A biologically active substance may be small molecules, polypeptides, proteins, DNA, RNA, cells and the like. Examples of biologically active substances include, but are not limited to those falling into the following therapeutic categories: ACE-inhibitors; anti-anginal drugs; anti-arrhythmias; anti-asthmatics; anti-cholesterolemics; anti-convulsants; anti-depressants; anti-diarrhea preparations; anti-histamines; anti-hypertensive drugs; anti-infectives; anti-inflammatory agents; anti-lipid agents; anti-manics; anti-nauseants; antistroke agents; anti-thyroid preparations; anti-tumor drugs; anti-tussives; anti-uricemic drugs; anti-viral agents; acne drugs; alkaloids; amino acid preparations; anabolic drugs; analgesics; anesthetics; angiogenesis inhibitors; antacids; anti-arthritics; antibiotics; anticoagulants; antiemetics; anti-obesity drugs; antiparasitics; antipsychotics; antipyretics; antispasmodics; antithrombotic drugs; anxiolytic agents; appetite stimulants; appetite suppressants; beta blocking agents; bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypnotics; hypoglycemic agents; laxatives; migraine treatments; mucolytics; narcotics; neuroleptics; neuromuscular drugs; NSAIDS; peripheral vasodilators; prostaglandins; psychotropics; renin inhibitors; respiratory stimulants; steroids; stimulants; sympatholytics; thyroid preparations; tranquilizers; uterine relaxants; vaginal preparations; vasoconstrictors; vasodilators; vertigo agents; vitamins; and wound healing agents. In the present invention, the term "(bio)degradable" or "cleaved automatically" indicates degradation occurs under physiological conditions without enzymatic catalysis. Such linkages include, but are not limited to, acetal bond, ester bond, imine bond, hydrazone bond, carboxylic acid anhydride, aconitic bond, ortho ester bond, amide bond of maleic acid, phosphoramide bond, phosphoric ester bond, sulfonic ester bond, aromatic urethane bond and their combinations thereof. Carboxylic ester bond and carbonate bond are preferred. However, a common disadvantage of these bonds is poor stability, which is easily degraded by various enzymes and is also prone to hydrolysis. Drug release rate and the degradation rate of the hydrogel based on these bonds can not be accurately controlled.

Amide bonds are known for their stability. Hydrolysis typically requires a strong acid (e.g. sulfuric acid, hydrochloric acid) or a strong base (e.g., sodium hydroxide) and high temperatures (e.g. 100° C.). Due to the relative stability of amides in vivo amide structures that can be automatically cleaved without the need for enzymatic hydrolysis are quite rare. The present invention shows, by taking advantage of intramolecular chemical catalysis, amide bonds can be hydrolyzed under mild conditions. Design and modification of the appropriate molecular scaffolds, as well as the choice of spatial, electron-withdrawing or electron-donating substituents at different positions of the scaffold, can modulate the reaction rates of amide bonds under physiological conditions. The same principle applies to ester bonds.

A moiety of biodegradable linkers of the present invention that can be cleaved under physiological conditions has the following formula:

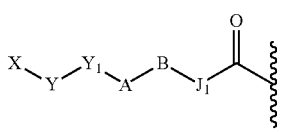

wherein X is selected from —OH and —HN—$R_0$;
Y is selected from:
(1) $NR_0$;
(2) $C(R_pR_q)$;
(3) O, with the proviso that X is not OH;
(4) $C(R_pR_q)$, when X is —HN—$R_0$, $R_0$ and $R_p$ together with the atoms to which they are attached form a 4, 5, or 6 membered heterocyclic ring;
$Y_1$ is selected from
(1) $C(R_3R_4)$;
(2) C(O) or C(S), with the proviso that A is not C(O), C(S), SO, or $SO_2$;
(3) O, S, SO, or $SO_2$, with the proviso that none of Y and A is O;
(4) $NR_0$; and
(5) a bond;
$J_1$ is $C(R_{10}R_{11})$ or a bond.

A and B together form a ring system, including aryl having from 6 to 15 carbon atoms; cycloalkyl having a 4, 5, 6, 7, 8, 9, or 10 membered ring; cycloalkenyl having a 4, 5, 6, 7, 8, 9, or 10 membered ring; cycloalkynyl having a 5, 6, 7, 8, 9, or 10 membered ring; saturated and unsaturated monocyclic, polycyclic, and fused cyclic; saturated and unsaturated monoheterocyclic, polyheterocyclic and fused heterocyclic, containing one or more heteroatoms N, S or O in each heterocyclic ring thereof and each ring being from 3- to 10-membered. Each of aforementioned ring is optionally substituted with one or more groups selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate (or salt), isothiocyanate, thiocyanate (or salt), lower alkylthio, amino, imino, amino lower alkyl, lower alkylamino, lower dialkylamino, hydroxyl, hydroxyl alkyl, nitro, nitrile, isonitrile, pyridyl, azido, carboxyl, carboxamido, acetic acid, thiolalkyl, carbonate (or salt), carbamate, loweralkylcarbamyl, diloweralkylcarbamyl, sulfonic acid group, sulfonamide group, sulfonate group (or salt), sulfonyl group, sulfoxide group, sulfide group, disulfide group, mercapto (or sulfhydryl) group.

Or A and B together with the atoms to which they are attached form an aromatic ring or a hetroaromatic ring optionally substituted by at least one group defined above; or A and B together with the atoms to which they are attached form a polyaromatic ring or a polyheteroaromatic ring optionally substituted by at least one group defined above.

Examples of the rings include, but not limited to, acridine, azepane, azepine, azocane, benzofuran, benzimidazole, benzothiophene, benzo[c]thiophene, benzoxazole, benzisoxazole, benzothiazole, cinnoline, diazepine, dioxolane, dithiolane, furan, furazan, imidazolidine, imidazole, indazole, indole, isoindole, isobenzofuran, isothiazole, isothiazolidine, isoxazole, isoxazolidines, morpholine, oxazines, oxadiazole, oxazole, oxazolidine, oxepane, quinazoline, quinoline, isoquinoline, quinoxaline, phosphole, phthalazine, piperidine, purine, pyridine, pyran, pyrrolidine, pyrrole, pyrazidine, pyrazine, pyrazole, piperazine, pyrimidine, pyridazine, thiazole, tetrazole, 1,2,3-triazine, 1,2,4-triazine, 1,3,5-triazine, triazole, thiane, thiazolidine, thiopyran, tetrahydrofuran, tetrahydrothiophene, thiadiazole, thiophene, thiomorpholine, thiazine, thiazepine, zocine $Y_1$ (or Y, if $Y_1$ is a covalent bond) and $J_1$ (or C(O), if $J_1$ is a covalent bond) are attached to two atoms on the same ring but are separated by one bond.

$R_0$, $R_O$, $R_3$, $R_4$, $R_{10}$, $R_{11}$, $R_n$, $R_p$, $R_q$ are independently selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate (or salt), isothiocyanate, thiocyanate (or salt), lower alkylthio, amino, imino, amino lower alkyl, lower alkylamino, lower dialkylamino, hydroxyl, hydroxyl alkyl, nitro, nitrile, isonitrile, pyridyl, azido, carboxyl, carboxamido, acetic acid, thiolalkyl, carbonate (or salt), carbamate, loweralkylcarbamyl, diloweralkylcarbamyl, sulfonic acid group, sulfonamide group, sulfonate group (or salt), sulfonyl group, sulfoxide group, sulfide group, disulfide group, mercapto (or sulfhydryl) group. Or $R_0$, $R_O$, $R_3$, $R_4$, $R_{10}$, $R_{11}$, $R_n$, $R_p$, $R_q$ are independently selected from —$SO_2OH$, —$SO_2NR_{m1}R_{m2}$, —$SO_2R_{m3}$, —O—$R_{m4}$, —S—$R_{m5}$, —N—$R_{m6}R_{m7}$, —C(O)$R_{m8}$, —C(O)O$R_{m9}$, —OC(O)$R_{m10}$, —NHC(O)$R_{m11}$, —C(O)NR$_{m12}R_{m13}$, —NHC(O)NR$_{m14}R_{m15}$, wherein $R_{m1}$, $R_{m2}$, $R_{m3}$, $R_{m4}$, $R_{m5}$, $R_{m6}$, $R_{m7}$, $R_{m8}$, $R_{m9}$, $R_{m10}$, $R_{m11}$, $R_{m12}$, $R_{m13}$, $R_{m14}$, and $R_{m15}$ are independently selected from hydrogen (H), ($C_1$-$C_{18}$) alkyl, aryl, ($C_1$-$C_{18}$ alkyl)OH, ($C_1$-$C_{18}$ alkyl)SH, ($C_1$-$C_{18}$ alkyl)COOH, ($C_1$-$C_{18}$ alkyl)NH$_2$, ($C_0$-$C_4$ alkyl)($C_5$-$C_6$ cycloalkyl), ($C_0$-$C_{10}$ alkyl)($C_5$-$C_6$ heterocyclic), ($C_0$-$C_4$ alkyl)($C_6$-$C_{10}$ aryl), ($C_0$-$C_4$ alkyl)($C_4$-$C_9$ heteroaryl). Or $R_p$ and $R_q$ are independently selected from ($C_1$-$C_{20}$)alkyl, ($C_1$-$C_{10}$alkyl)OH, ($C_1$-$C_{10}$ alkyl)SH, ($C_2$-$C_3$ alkyl)SCH$_3$, ($C_1$-$C_4$ alkyl)CONH$_2$, ($C_1$-$C_{10}$ alkyl)COOH, ($C_1$-$C_{10}$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl), ($C_0$-$C_4$ alkyl)($C_6$-$C_{10}$ aryl)R$_{16}$, ($C_1$-$C_4$ alkyl)($C_3$-$C_9$ heteroaryl), and $C_1$-$C_{12}$ alkyl($W_1$)$C_1$-$C_{12}$ alkyl, wherein Wiis a heteroatom selected from N, S and O; $R_{16}$ is selected from H, OH, halo, $C_1$-$C_7$ alkyl, $C_2$-$C_7$ alkenyl, $C_2$-$C_7$ alkynyl, CO$_2$H, CO$_2$($C_1$-$C_7$ alkyl), NH ($C_0$-$C_{10}$ alkyl), O($C_1$-$C_{10}$ alkyl), aryl, and heteroaryl.

It will be understood by those skilled in the art, with respect to any biodegradable linker containing one or more substituents, that such linkers are not intended to introduce any substitution or substitution patterns that are sterically impractical, synthetically non-feasible and/or inherently unstable.

The degradable moieties of biodegradable linkers in the present invention can be degraded by intramolecular cyclization reaction.

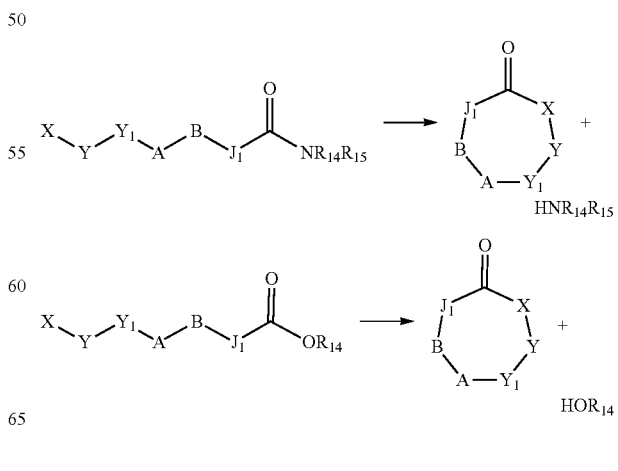

Wherein $R_{14}$ and $R_{15}$ may be a substructure of the nitrogen- or hydroxyl-containing biologically active substance, or a component of a nitrogen or hydroxyl-containing polymer.

Degradation by intramolecular cyclization does not require enzyme participation and reaction rate depends on the temperature and physiological pH. Since temperature and physiological pH are generally constant in human population, this degradation mechanism minimizes inter and intra patient variations seen in enzymatic hydrolysis, resulting in more consistent and reproducible therapeutic effects.

In some embodiments, $J_1$ is $C(R_{10}R_{11})$ and $Y_1$ is a bond, and biodegradable linkers are of the following formula:

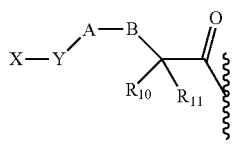

In some embodiments, $Y_1$ is $C(R_3R_4)$, $J_1$ is a bond, and biodegradable linkers are of the following formula:

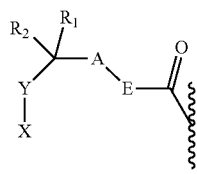

In some embodiments, $Y_1$ is $C(R_3R_4)$, $J_1$ is $C(R_{10}R_{11})$, and biodegradable linkers are of the following formula:

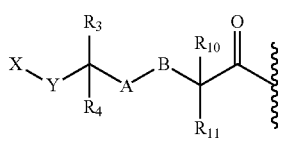

In some embodiments, biodegradable linkers are of the following formula:

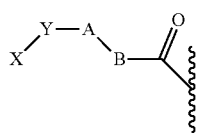

Subclass 1

In some embodiments, one subclass of biodegradable linking groups is of the following formula:

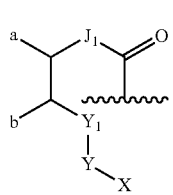 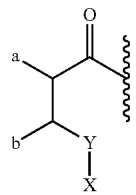 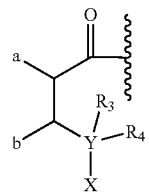

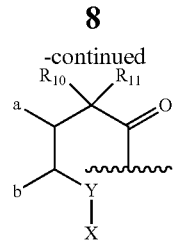

wherein X is OH or HN—$R_0$;

Y is selected from
(1) N—$R_0$;
(2) $C(R_pR_q)$;
(3) O, with the proviso that X is not OH;
(4) $C(R_pR_q)$, when X is HN—$R_0$, $R_0$ and $R_p$ together with the atoms to which they are attached form a 4, 5, or 6 membered heterocyclic ring;

$Y_1$ is selected from
(1) $C(R_3R_4)$;
(2) C(O) or C(S), with the proviso that none of Y and A is C(O), C(S), SO, or $SO_2$;
(3) O, S, SO, or $SO_2$, with the proviso that none of Y and A is O;
(4) N—$R_0$; and
(5) a covalent bond.

$J_1$ is $C(R_{10}R_{11})$ or a covalent bond.

a and b together with the atoms to which they are attached form a bicyclic ring system, comprising a saturated five-membered or 6-membered ring to which an aromatic ring is fused. A saturated five-membered or 6-membered ring may be a cycloalkyl group, or a heterocyclic ring comprising one or more heteroatoms N, S or O. $Y_1$ (or Y, if $Y_1$ is a covalent bond) and $J_1$ (or C(O), if $J_1$ is a covalent bond) are attached to two atoms on the same saturated five-membered or 6-membered ring but are separated by one bond. A hydrogen atom on the aromatic ring is optionally substituted with one or more groups selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate (or salt), isothiocyanate, thiocyanate (or salt), lower alkylthio, amino, imino, amino lower alkyl, lower alkylamino, lower dialkylamino, hydroxyl, hydroxyl alkyl, nitro, nitrile, isonitrile, pyridyl, azido, carboxyl, carboxamido, acetic acid, thiolalkyl, carbonate (or salt), carbamate, loweralkylcarbamyl, diloweralkylcarbamyl, sulfonic acid group, sulfonamide group, sulfonate group (or salt), sulfonyl group, sulfoxide group, sulfide group, disulfide group, mercapto (or sulfhydryl) group.

When the ring is a saturated cycloalkyl group, an exemplary, non-limiting example is of the following formula:

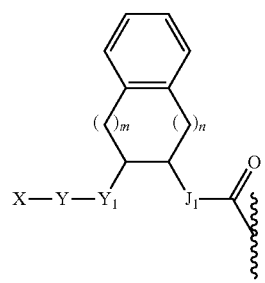

wherein m, n are an integer of 0 or 1, but m, n are not simultaneously 0.

In some embodiments, a subclass of biodegradable linkers is of the formula below, wherein X, Y, $R_3$, $R_4$, $R_{10}$, $R_n$, a and b are the same as defined above:

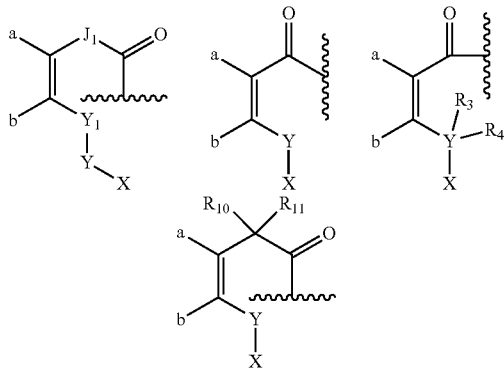

Or a and b together with the atoms to which they are attached form a monocyclic aromatic ring, a polycyclic aromatic ring, a fused aromatic ring, a monoheteroaromatic ring, a poly heteroaromatic ring, or a fused heteroaromatic ring, optionally substituted with one or more groups selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate (or salt), isothiocyanate, thiocyanate (or salt), lower alkylthio, amino, imino, amino lower alkyl, lower alkylamino, lower dialkylamino, hydroxyl, hydroxyl alkyl, nitro, nitrile, isonitrile, pyridyl, azido, carboxyl, carboxamido, acetic acid, thiolalkyl, carbonate (or salt), carbamate, loweralkylcarbamyl, diloweralkylcarbamyl, sulfonic acid group, sulfonamide group, sulfonate group (or salt), sulfonyl group, sulfoxide group, sulfide group, disulfide group, mercapto (or sulfhydryl) group.

Subclass 2

In some embodiments, one subclass of biodegradable linkers containing a 6-member ring is of the following formula:

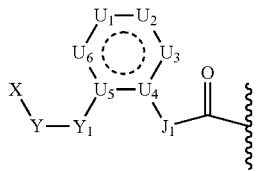

wherein $U_1$, $U_2$, $U_3$, $U_4$, $U_5$, and $U_6$ are independently selected from C—$R_{12}$ and N; X is OH or HN—$R_0$;
Y is selected from:
(1) N—$R_O$;
(2) C($R_p R_q$);
(3) O, with the proviso that X is not OH;
(4) C($R_p R_q$), when X is HN—$R_0$, $R_0$ and $R_p$ together with the atoms to which they are attached form a 4, 5, or 6 membered heterocyclic ring;
$Y_1$ is selected from
(1) C($R_3 R_4$);
(2) C(O) or C(S), with the proviso that A is not C(O), C(S), SO, or $SO_2$;
(3) O, S, SO, or $SO_2$, with the proviso that none of Y and A is O;
(4) N—$R_n$; and
(5) a bond;
$J_1$ is C($R_{10} R_{11}$) or a bond;

$R_{12}$ is selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate (or salt), isothiocyanate, thiocyanate (or salt), lower alkylthio, amino, imino, amino lower alkyl, lower alkylamino, lower dialkylamino, hydroxyl, hydroxyl alkyl, nitro, nitrile, isonitrile, pyridyl, azido, carboxyl, carboxamido, acetic acid, thiolalkyl, carbonate (or salt), carbamate, loweralkylcarbamyl, diloweralkylcarbamyl, sulfonic acid group, sulfonamide group, sulfonate group (or salt), sulfonyl group, sulfoxide group, sulfide group, disulfide group, mercapto (or sulfhydryl) group. Or $R_{12}$ is selected from —$SO_2$—OH, —$SO_2$—$NR_{m1}R_{m2}$, —$SO_2$—$R_{m3}$, —O—$R_{m4}$, —S—$R_{m5}$, —N—$R_{m6}R_{m7}$, —C(O)$R_{m8}$, —C(O)O$R_{m9}$, —OC(O)$R_{m10}$, —NHC(O)$R_{m11}$, —C(O)N$R_{m12}R_{m13}$, —NHC(O)N$R_{m14}R_{m15}$, wherein $R_{m1}$, $R_{m2}$, $R_{m3}$, $R_{m4}$, $R_{m5}$, $R_{m6}$, $R_{m7}$, $R_{m8}$, $R_{m9}$, $R_{m10}$, $R_{m11}$, $R_{m12}$, $R_{m13}$, $R_{m14}$, and $R_{m15}$ are independently selected from hydrogen (H), ($C_1$-$C_{18}$) alkyl, aryl, ($C_1$-$C_{18}$ alkyl)OH, ($C_1$-$C_{18}$alkyl)SH, ($C_1$-$C_{13}$alkyl) COOH, ($C_1$-$C_{18}$ alkyl)$NH_2$, ($C_0$-$C_4$ alkyl)($C_5$-$C_6$ cycloalkyl), ($C_0$-$C_{10}$ alkyl)($C_5$-$C_6$ heterocyclic), ($C_0$-$C_4$ alkyl)($C_6$-$C_{10}$ aryl), ($C_0$-$C_4$ alkyl)($C_4$-$C_9$ heteroaryl).

In some embodiments, $R_{12}$ contains a hydroxyl group, an amino group, a carboxyl group, a mercapto group and the like which can be used to form a covalent bond with crosslinking functional groups of reactive polymers. In some embodiments, $R_2$ contains an azide or alkyne which can react with corresponding alkyne or azide on a reactive polymer by click chemistry.

Subclass 3

In some embodiments, one subclass of biodegradable linkers containing a 6-member ring is of the following formula:

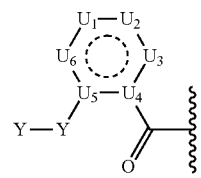

Wherein X is OH or HN—$R_0$;
Y is selected from:
(1) N—$R_O$;
(2) C($R_p R_q$);
(3) O, with the proviso that X is not OH;
(4) C($R_p R_q$), when X is HN—$R_0$, $R_0$ and $R_p$ together with the atoms to which they are attached form a 4, 5, or 6 membered heterocyclic ring;
$U_1$, $U_2$, $U_3$, $U_4$, $U_5$, $U_6$, $R_0$, Ro, $R_p$ and $R_q$ are the same as defined above.

Biodegradable linkers in this subclass include, but are not limited to, the following examples:

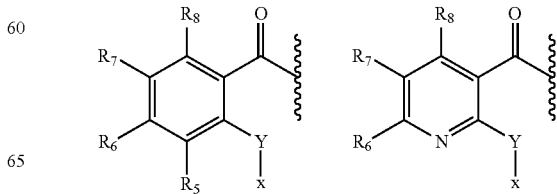

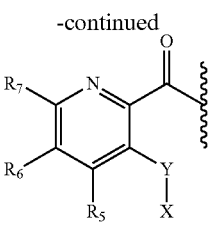

In some embodiments, Y in above three formulae is selected from NH, N—R$_O$, O (with the proviso that X is not OH).

In some embodiments, Y is N—R$_O$, X is HN—R$_0$ or OH. Biodegradable linkers in this subclass are of the following formulae:

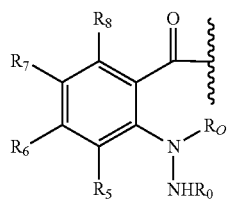 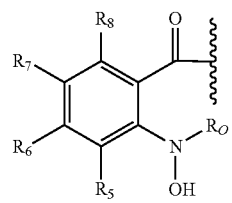

In some embodiments, R$_0$ is hydrogen (H) and biodegradable linkers in this subclass are of the following formulae:

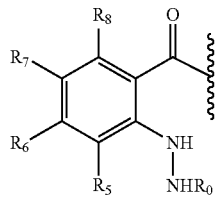 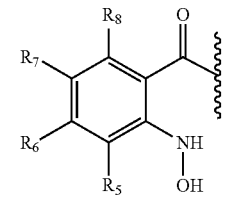

R$_5$, R$_6$, R$_7$, and R$_8$ are selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate (or salt), isothiocyanate, thiocyanate (or salt), lower alkylthio, amino, imino, amino lower alkyl, lower alkylamino, lower dialkylamino, hydroxyl, hydroxyl alkyl, nitro, nitrile, isonitrile, pyridyl, azido, carboxyl, carboxamido, acetic acid, thiolalkyl, carbonate (or salt), carbamate, loweralkylcarbamyl, diloweralkylcarbamyl, sulfonic acid group, sulfonamide group, sulfonate group (or salt), sulfonyl group, sulfoxide group, sulfide group, disulfide group, mercapto (or sulfhydryl) group. Or R$_5$, R$_6$, R$_7$, and R$_8$ are selected from —SO$_2$OH, —SO$_2$NR$_{m1}$R$_{m2}$, —SO$_2$R$_{m3}$, —O—R$_{m4}$, —S—R$_{m5}$, —N—R$_{m6}$R$_{m7}$, —C(O)R$_{m8}$, —C(O)OR$_{m9}$, —OC(O)R$_{m10}$, —NHC(O)R$_{m11}$, —C(O)NR$_{m12}$R$_{m13}$, —NHC(O)NR$_{m14}$R$_{m15}$, wherein R$_{m1}$, R$_{m2}$, R$_{m3}$, R$_{m4}$, R$_{m5}$, R$_{m6}$, R$_{m7}$, R$_{m8}$, R$_{m9}$, R$_{m10}$, R$_{m11}$, R$_{m12}$, R$_{m13}$, R$_{m14}$, and R$_{m15}$ are independently selected from hydrogen (H), (C$_1$-C$_{18}$) alkyl, aryl, (C$_1$-C$_{18}$ alkyl)OH, (C$_1$-C$_{18}$ alkyl)SH, (C$_1$-C$_{18}$ alkyl)COOH, (C$_1$-C$_{18}$ alkyl)NH$_2$, (C$_0$-C$_4$ alkyl)(C$_5$-C$_6$ cycloalkyl), (C$_0$-C$_{10}$ alkyl)(C$_5$-C$_6$ heterocyclic), (C$_0$-C$_4$ alkyl)(C$_6$-C$_{10}$ aryl), (C$_0$-C$_4$ alkyl)(C$_4$-C$_9$ heteroaryl).

In some embodiments, Y is O, and this subclass of biodegradable linkers is of the following formula, wherein R$_5$, R$_6$, R$_7$, and R$_8$ are defined as above:

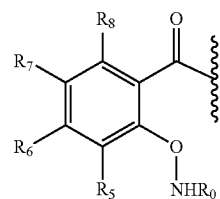

In some embodiments, Y is C(R$_p$R$_a$), and the biodegradable linkers in this subclass are of the following formula, wherein X, U$_1$, U$_2$, U$_3$, U$_4$, U$_5$, and U$_6$ are defined as above:

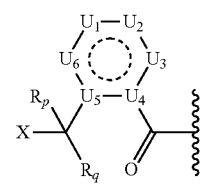

In some embodiments, the biodegradable linkers in this subclass include, but are not limited to the following examples, wherein X, R$_5$, R$_6$, R$_7$, and R$_8$ are defined as above:

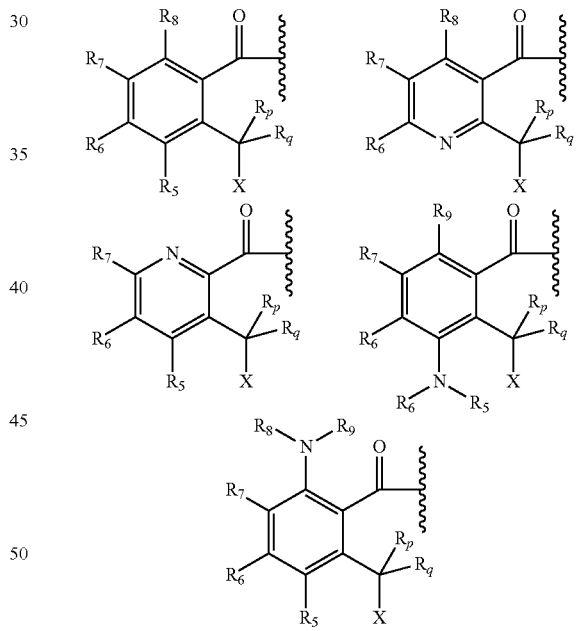

R$_9$ is selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate (or salt), isothiocyanate, thiocyanate (or salt), lower alkylthio, amino, imino, amino lower alkyl, lower alkylamino, lower dialkylamino, hydroxyl, hydroxyl alkyl, nitro, nitrile, isonitrile, pyridyl, azido, carboxyl, carboxamido, acetic acid, thiolalkyl, carbonate (or salt), carbamate, loweralkylcarbamyl, diloweralkylcarbamyl, sulfonic acid group, sulfonamide group, sulfonate group (or salt), sulfonyl group, sulfoxide group, sulfide group, disulfide group, mercapto (or sulfhydryl) group. Or R$_9$ is selected from —SO$_2$—OH, —SO$_2$—NR$_{m1}$R$_{m2}$, —SO$_2$—R$_{m3}$, —O—R$_{m4}$, —S—R$_{m5}$, —N—R$_{m6}$R$_{m7}$, —C(O)R$_{m5}$, —C(O)OR$_{m9}$, —OC(O)R$_{m10}$, —NHC(O)R$_{m11}$, —C(O)NR$_{m12}$R$_{m13}$, —NHC(O) NR$_{m14}$R$_{m15}$, wherein R$_{m1}$, R$_{m2}$, R$_{m3}$, R$_{m4}$, R$_{m5}$, R$_{m6}$, R$_{m7}$, R$_{m8}$, R$_{m9}$, R$_{m10}$, R$_{m11}$, R$_{m12}$, R$_{m13}$, R$_{m14}$, and R$_{m15}$ are independently selected from hydrogen (H), (C$_1$-C$_{18}$) alkyl, aryl, (C$_1$-C$_{18}$alkyl)OH, (C$_1$-C$_{18}$alkyl)SH, (C$_1$-C$_{13}$alkyl) COOH, (C$_1$-C$_{18}$alkyl)NH$_2$, (C$_0$-C$_4$ alkyl)(C$_5$-C$_6$ cycloalkyl), (C$_0$-C$_{10}$ alkyl)(C$_5$-C$_6$ heterocyclic), (C$_0$-C$_4$ alkyl)(C$_6$-C$_{10}$ aryl), (C$_0$-C$_4$ alkyl)(C$_4$-C$_9$ heteroaryl).

In some embodiments, R$_5$, R$_6$, R$_7$, R$_8$, and R$_9$ contain a hydroxyl group, an amino group, a carboxyl group, a mercapto group and the like which can be used to form a covalent bond with the crosslinking functional groups of reactive polymers. In some embodiments, R$_5$, R$_6$, R$_7$, R$_8$, and R$_9$ contains an azide or alkyne which can react with corresponding alkyne or azide on a reactive polymer by click chemistry.

In some embodiments R$_p$ and R$_q$ are hydrogen (H). A group of biodegradable linkers in this subclass is of the following formula, wherein X, R$_5$, R$_6$, R$_7$, and R$_8$ are defined as above:

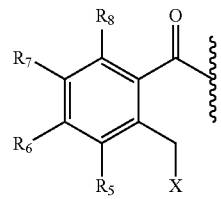

In some embodiments, biodegradable linkers in this group are of the following formulae:

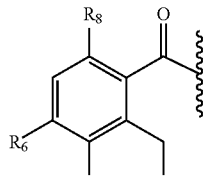 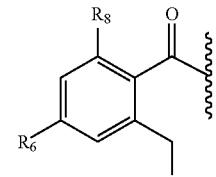

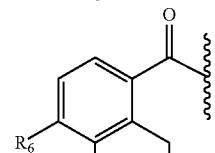 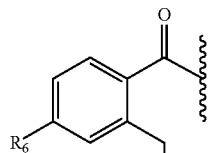

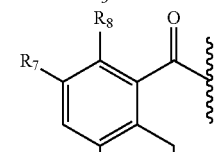 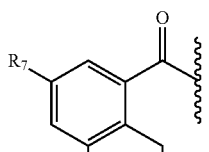

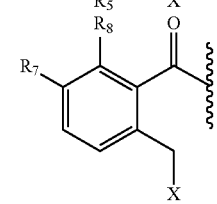 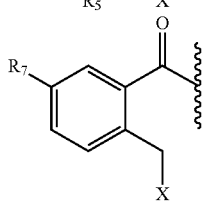

In some embodiments, biodegradable linkers in this subclass are of the following formula, wherein X, R$_6$, and R$_7$ are defined as above:

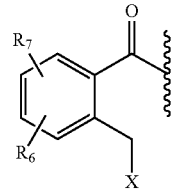

In some embodiments, biodegradable linkers in this group are of the following formulae, wherein X, R$_6$, and R$_7$ are defined as above:

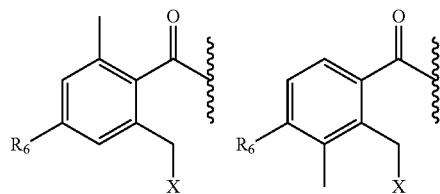

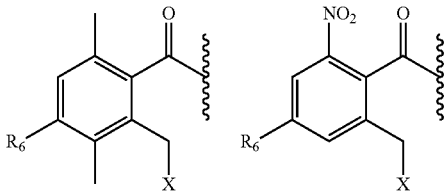

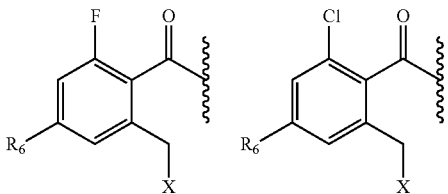

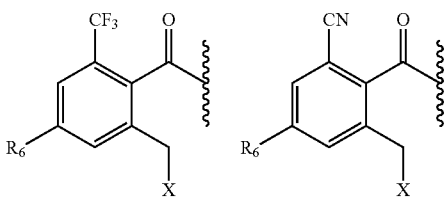

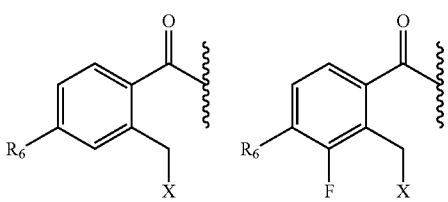

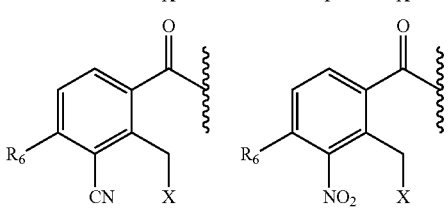

15

-continued

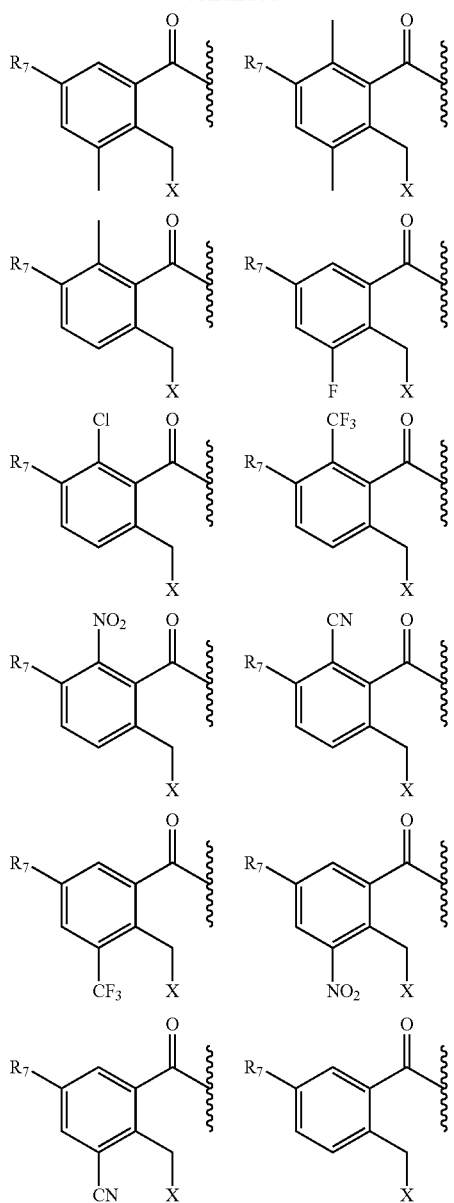

In some embodiments, X in above formulae is OH or HN—R₀.

In some embodiments, X in above formulae is OH.

In some embodiments, X in above formulae is HN—R₀.

In some embodiments, X in above formulae is $NH_2$.

Illustrative, non-limiting examples of biodegradable linkers include:

16

-continued

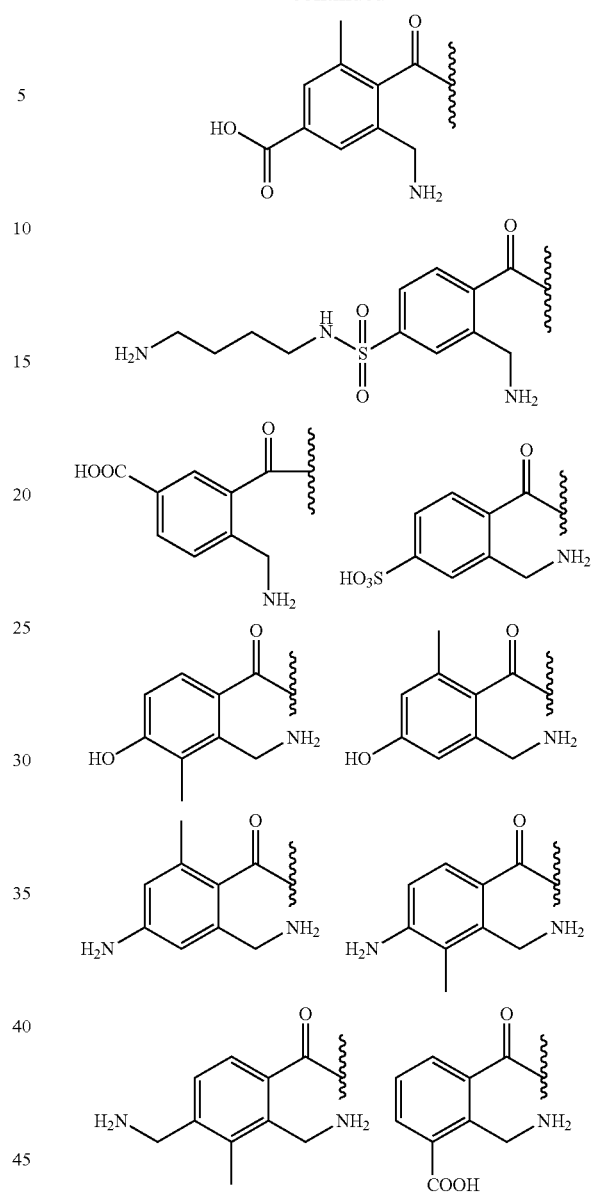

Subclass 4

In some embodiments, $Y_1$ is $C(R_3R_4)$ and one subclass of biodegradable linkers containing a 6-member ring is of the following formula:

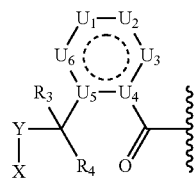

wherein X is OH or HN—$R_O$;

Y is selected from (1) N—$R_O$;

(2) C($R_p R_q$);

(3) O, with the proviso that X is not OH; and (4) C($R_p R_q$), when X is HN—$R_0$, $R_0$ and $R_p$ together with the atoms to which they are attached form a 4, 5, or 6 membered heterocyclic ring; and $U_1$, $U_2$, $U_3$, $U_4$, $U_5$, $U_6$, $R_3$, $R_4$, $R_0$, Ro, $R_p$ and $R_q$ are defined as above.

In some embodiments, the biodegradable linkers in this subclass include, but are not limited to the following examples, wherein X, Y, and $R_3$-$R_9$ are defined as above:

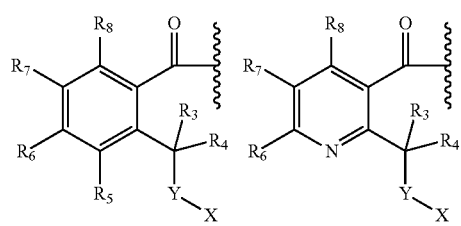

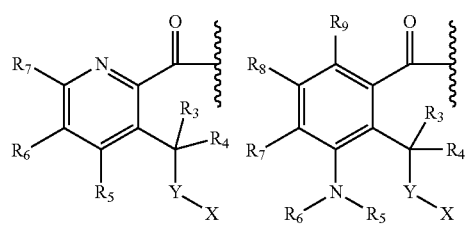

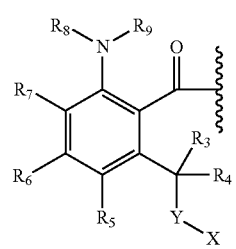

In some embodiments, Y is selected from (1) $NR_O$;

(2) O, with the proviso that X is not OH.

In some embodiments Y is C($R_p R_q$) and the biodegradable linkers in this subclass are of the formula, wherein X, $R_3$-$R_9$, $R_p$, and $R_q$ are defined as above:

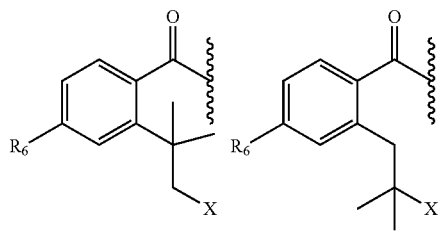

Examples of biodegradable linkers include, but not limited to, the following formulae:

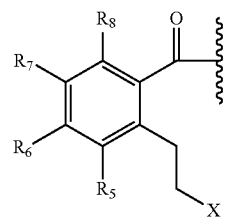

In some embodiments, Y is CH$_2$, and the biodegradable linkers in this subclass are of the following formula, wherein X and $R_5$-$R_8$ are defined above:

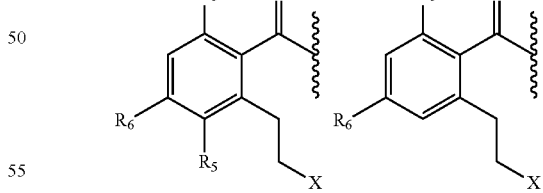

In some embodiments, the biodegradable linkers in this subclass are of the following formulae, wherein $R_5$-$R_8$ are defined above:

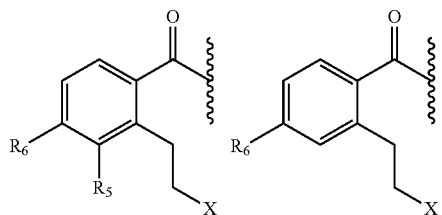

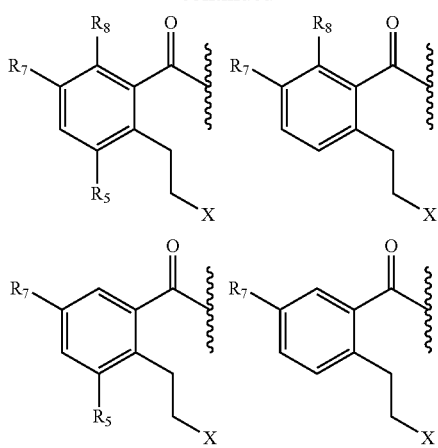

In some embodiments, X is OH or HN—R₀.

In some embodiments, X is OH.

In some embodiments, X is HN—R₀.

Examples of biodegradable linkers in this subclass include, but not limited to, the following formulae:

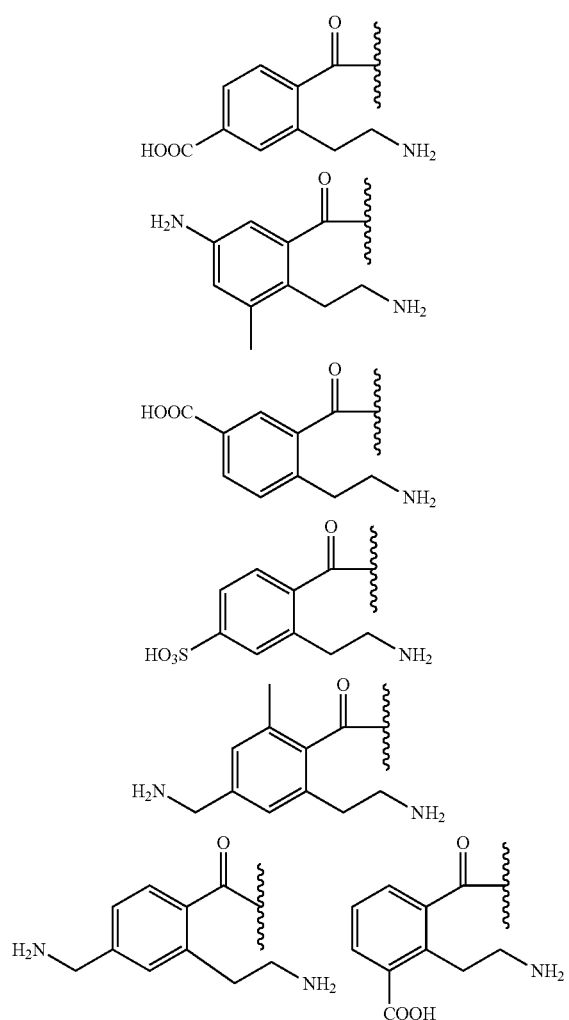

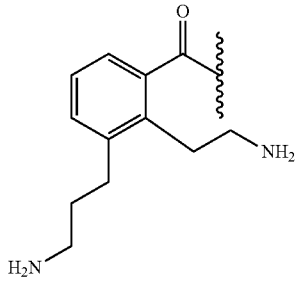

Subclass 5

In some embodiments, $U_5$ is C, $Y_1$ is N—$R_n$, Y is $C(R_p R_q)$, and one subclass of biodegradable linkers containing a 6-member ring is of the following formula, wherein $U_1$-$U_4$, $U_6$, $R_n$, $R_p$, $R_q$, and X are defined as above:

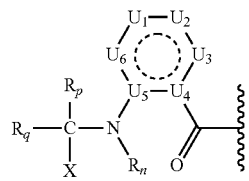

In some embodiments, the biodegradable linkers in this subclass include, but are not limited to, the following formula, wherein $R_5$-$R_8$, $R_n$, $R_p$, $R_q$, and X are defined as above:

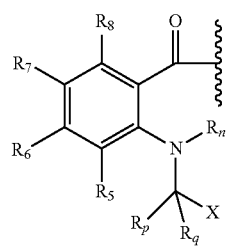

Subclass 6

In some embodiments, $U_5$ is C, $Y_1$ is O, Y is C—$R_p R_q$, and one subclass of biodegradable linkers containing a 6-member ring is of the following formula, wherein $U_1$-$U_4$, $U_6$, $R_p$, $R_q$, and X are the same defined as above:

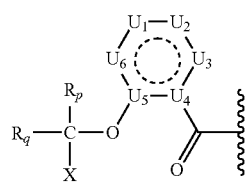

In some embodiments, the biodegradable linkers in this subclass include, but are not limited to, the following formula, wherein $R_5$-$R_8$, $R_p$, $R_q$, and X are defined as above:

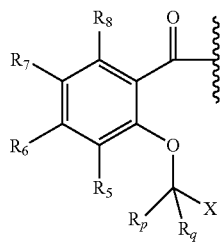

Subclass 7
In some embodiments, $Y_1$ is C(O), C(S), SO, or $SO_2$, and the biodegradable linkers in this subclass are of the following formula:

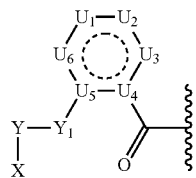

wherein X is OH or HN—$R_0$;
Y is
(1) N—$R_O$;
(2) C($R_p R_q$);
(3) O, with the proviso that X is not OH; and
(4) C($R_p R_q$), when X is HN—$R_0$, $R_0$ and $R_p$ together with the atoms to which they are attached can form a 4, 5, or 6 membered heterocyclic ring;
wherein $R_O$, $R_0$, $R_p$, $R_q$, and $U_1$—$U_6$ are the same as defined above.

In some embodiments, biodegradable linkers in this subclass are of the following formulae, wherein $R_5$-$R_8$ are the same as defined above:

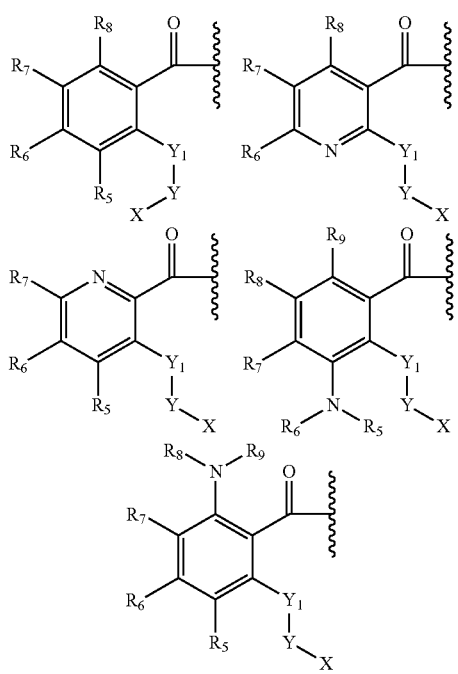

In some embodiments, $Y_1$ is C(O) and the biodegradable linkers in this subclass are of the following formulae, wherein $R_5$-$R_8$ are the same as defined above:

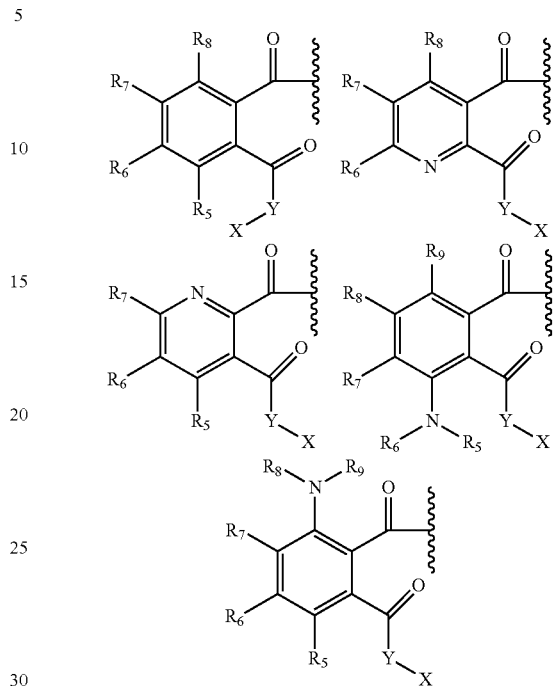

In some embodiments, Y is N—$R_O$, wherein $R_O$ is the same as defined above.
In some embodiments, Y is C—$R_p R_q$, wherein $R_p$ and $R_q$ are the same as defined above.
In some embodiments, X is OH or HN—$R_0$, wherein $R_0$ is the same as defined above.

Subclass 8
In some embodiments, $J_1$ is C($R_{10} R_{11}$) and one subclass of biodegradable linkers containing a 6-member ring is of the following formula:

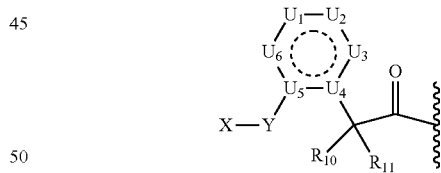

wherein $U_1$, $U_2$, $U_3$, $U_4$, $U_5$, $U_6$ are independently selected from C—$R_{12}$ and N;
X is OH or HN—$R_0$;
Y is
(1) N—$R_O$;
(2) C($R_p R_q$);
(3) O, with the proviso that X is not OH; and
(4) C($R_p R_q$), when X is HN—$R_0$, $R_0$ and $R_p$ together with the atoms to which they are attached can form a 4, 5, or 6 membered heterocyclic ring;
wherein $R_O$, Ro, $R_p$, $R_q$, and $R_{10}$-$R_{12}$ are the same as defined above.
In some embodiments, Y is selected from N—$R_O$ and O (with the proviso that X is not OH).
In some embodiments, Y is C($R_p R_q$).

In some embodiments, biodegradable linkers in this subclass are of the following formulae, wherein $R_5$-$R_8$, $R_p$, $R_q$, $R_{10}$, and $R_{11}$ are the same as defined above:

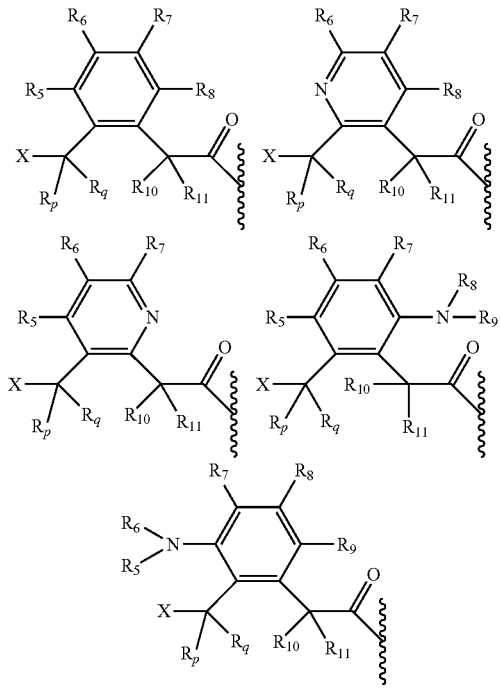

In some embodiments, $R_{10}$, $R_{11}$, $R_p$, $R_q$ are hydrogen (H) and biodegradable linkers in this subclass are of the following formula, wherein $R_5$-$R_8$ are the same as defined above:

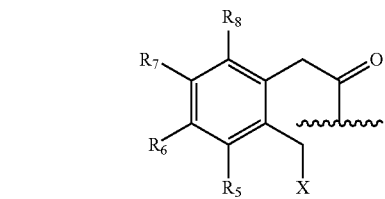

In some embodiments, $R_{10}$, $R_{11}$, $R_p$, $R_q$ are hydrogen (H) and the biodegradable linkers in this subclass are of the following formulae, wherein $R_5$-$R_8$ are the same as defined above:

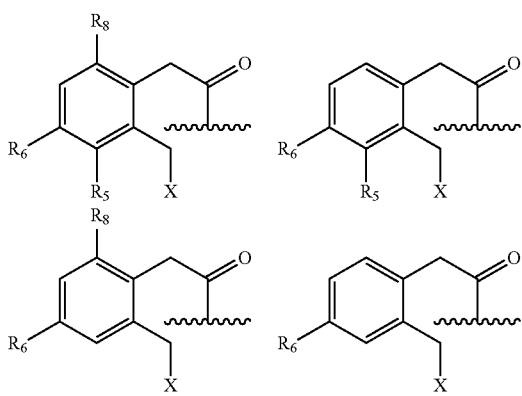

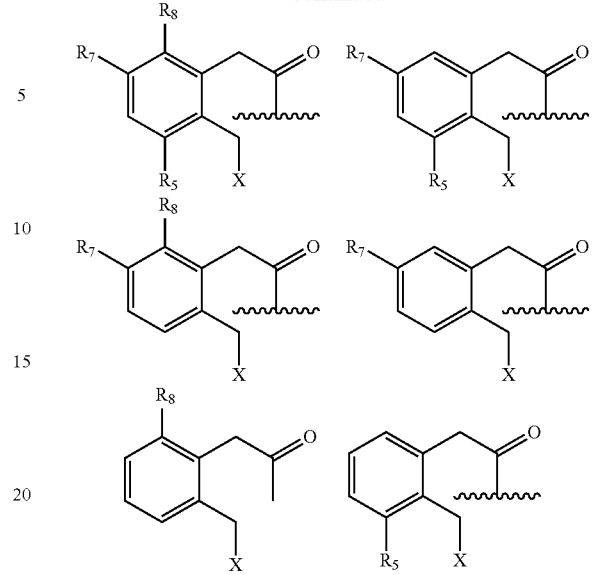

In some embodiments, X is OH or HN—$R_0$, wherein $R_0$ is the same as defined above.

In some embodiments, X is OH.

In some embodiments, X is HN—$R_0$, wherein $R_0$ is the same as defined above.

In some embodiments, X is $NH_2$.

Examples of biodegradable linkers in this subclass include, but are not limited to, the following formulae:

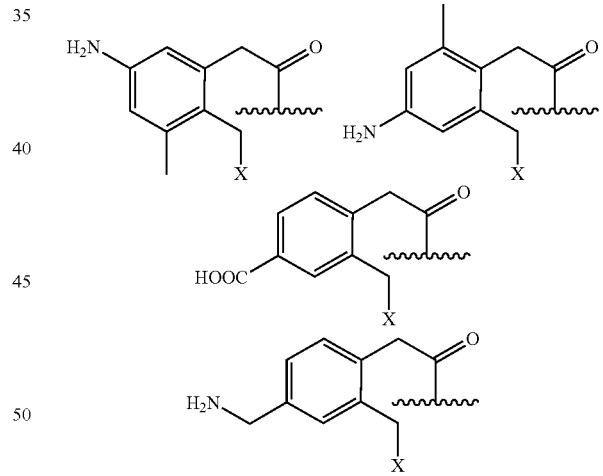

Subclass 9

In some embodiments, one subclass of biodegradable linkers containing a 5-member ring is of the following formula:

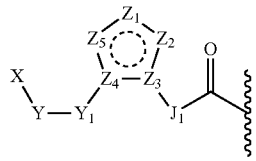

wherein $Z_1$, $Z_2$, $Z_3$, $Z_4$, $Z_5$ are independently selected from C—$R_{12}$, N,N—$R_{13}$, O, and S; X is OH or HN—$R_0$; Y is
(1) N—$R_O$;
(2) C($R_pR_q$);
(3) O, with the proviso that X is not OH;
(4) C($R_pR_q$), when X is HN—$R_0$, $R_0$ and $R_p$ together with the atoms to which they are attached can form a 4, 5, or 6 membered heterocyclic ring;
$Y_1$ is selected from
(1) C($R_3R_4$);
(2) C(O) or C(S), with the proviso that none of Y and A is C(O), C(S), SO, or $SO_2$;
(3) O, S, SO, or $SO_2$, with the proviso that none of Y and A is O;
(4) N—$R_n$; and
(5) a covalent bond.
$J_1$ is C($R_{10}R_{11}$) or a covalent bond;
$R_{13}$ is selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate (or salt), isothiocyanate, thiocyanate (or salt), lower alkylthio, amino, imino, amino lower alkyl, lower alkylamino, lower dialkylamino, hydroxyl, hydroxyl alkyl, nitro, nitrile, isonitrile, pyridyl, azido, carboxyl, carboxamido, acetic acid, thiolalkyl, carbonate (or salt), carbamate, loweralkylcarbamyl, diloweralkylcarbamyl, sulfonic acid group, sulfonamide group, sulfonate group (or salt), sulfonyl group, sulfoxide group, sulfide group, disulfide group, mercapto (or sulfhydryl) group. Or $R_{13}$ is selected from —$SO_2$—OH, —$SO_2NR_{m1}R_{m2}$, —$SO_2$—$R_{m3}$, —O—$R_{m4}$, —S—$R_{m5}$, —N—$R_{m6}R_{m7}$, —C(O)$R_{m8}$, —C(O)O$R_{m9}$, —OC(O)$R_{m10}$, —NHC(O)$R_{m11}$, —C(O)N$R_{m12}R_{m13}$, —NHC(O) N$R_{m14}R_{m15}$, wherein $R_{m1}$, $R_{m2}$, $R_{m3}$, $R_{m4}$, $R_{m5}$, $R_{m6}$, $R_{m7}$, $R_{m8}$, $R_{m9}$, $R_{m10}$, $R_{m11}$, $R_{m12}$, $R_{m13}$, $R_{m14}$, and $R_{m15}$ are independently selected from hydrogen (H), ($C_1$-$C_{18}$) alkyl, aryl, ($C_1$-$C_{18}$alkyl)OH, ($C_1$-$C_{18}$alkyl)SH, ($C_1$-$C_{18}$alkyl)COOH, ($C_1$-$C_{18}$alkyl)$NH_2$, ($C_0$-$C_4$ alkyl)($C_5$-$C_6$ cycloalkyl), ($C_0$-$C_{10}$ alkyl)($C_5$-$C_6$ heterocyclic), ($C_0$-$C_4$ alkyl)($C_6$-$C_{10}$ aryl), ($C_0$-$C_4$ alkyl)($C_4$-$C_9$ heteroaryl).

In some embodiments, $R_{13}$ contains a hydroxyl group, an amino group, a carboxyl group, a mercapto group and the like which can be used to form a covalent bond with the crosslinking functional groups of reactive polymers. In some embodiments, $R_{13}$ contains an azide or alkyne which can react with corresponding alkyne or azide on a reactive polymer by click chemistry.

$R_0$, Ro, $R_p$, $R_q$, $R_3$, $R_4$, and $R_{10}$-$R_{12}$ are the same as defined above.

Some examples of these 5-member rings formed by $Z_1$-$Z_5$ are tetrazoles and triazoles, wherein $R_5$ is the same as defined above:

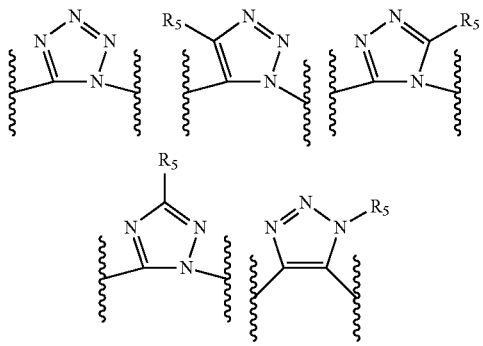

Some examples of these 5-member rings formed by $Z_1$-$Z_5$ are imidazoles, wherein $R_5$ and $R_6$ are the same as those defined above:

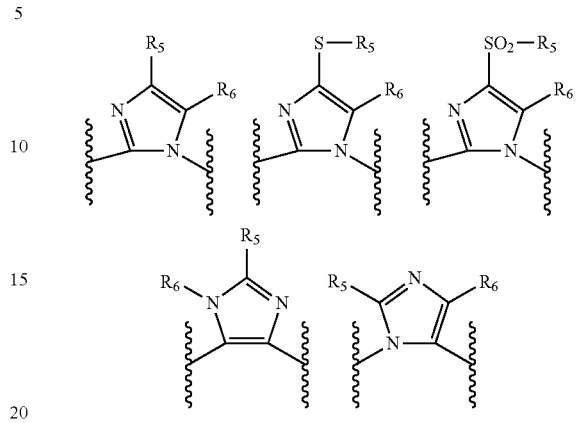

Some examples of these 5-member rings formed by $Z_1$-$Z_5$ are pyrroles, wherein $R_5$-$R_7$ are the same as those defined above:

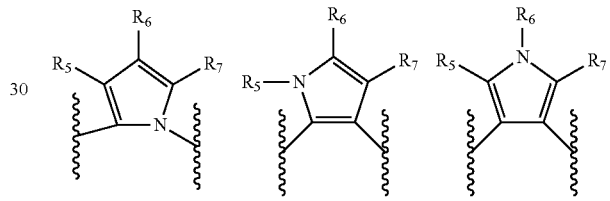

Some examples of these 5-member rings formed by $Z_1$—$Z_5$ are pyrazoles, wherein $R_5$ and $R_6$ are the same as those defined above:

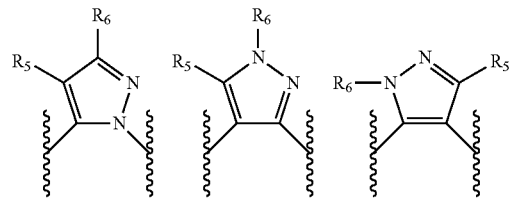

Some other examples of these 5-member rings formed by $Z_1$-$Z_5$ are furans, wherein $R_5$ and $R_6$ are the same as those defined above:

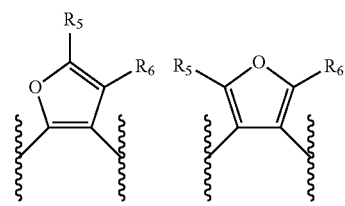

Some other examples of these 5-member rings formed by $Z_1$-$Z_5$ are thiophenes, wherein $R_5$ and $R_6$ are the same as those defined above:

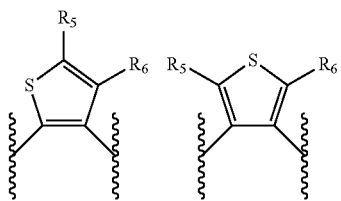

Some other examples of these 5-member rings formed by $Z_1$-$Z_5$ are thiazoles, isothiazoles, oxazoles, and isoxazoles, wherein $R_5$ is the same as defined above:

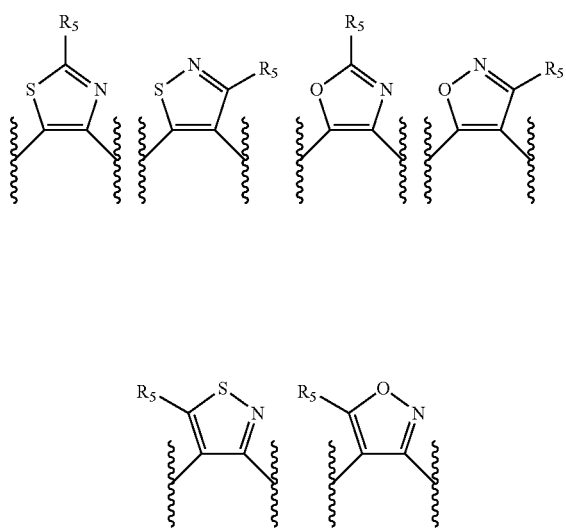

In some embodiments, $Y_1$ is a bond, $J_1$ is $C(R_{10}R_{11})$, and one subclass of biodegradable linkers containing a 5-member ring is of the following formula:

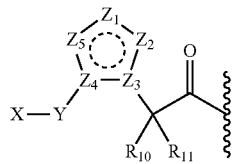

In some embodiments, $J_1$ is $C(R_{10}R_{11})$, $Y_1$ is a bond, Y is $C(R_pR_q)$, and one subclass of biodegradable linkers containing a 5-member ring is of the following formula:

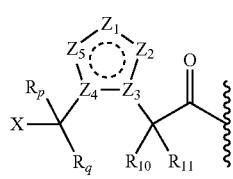

In some embodiments, Y is $C(R_pR_q)$, $J_1$ is $C(R_{10}R_{11})$, and one subclass of triazole based biodegradable linkers is of the following formula:

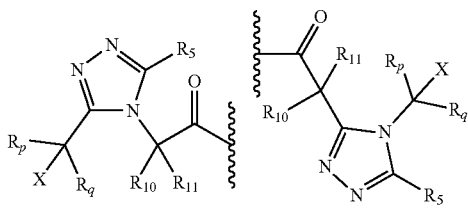

In some embodiments, X is OH, or HN—$R_0$;
In some embodiments, X is OH;
In some embodiment, X is HN—$R_0$.
In some embodiments, X is $NH_2$.

In some embodiments a subclass of triazole based biodegradable linkers is of the following formulae, wherein $R_5$ is the same as defined above:

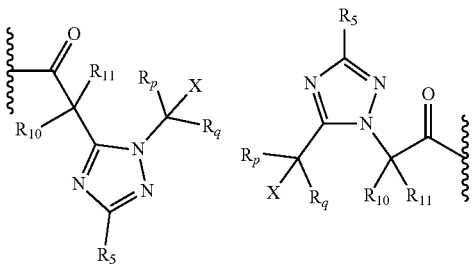

In some embodiments, Y is $C(R_pR_q)$, $J_1$ is $C(R_{10}R_{11})$, and one subclass of triazole based biodegradable linkers is of the following formulae wherein $R_5$ is the same as defined above:

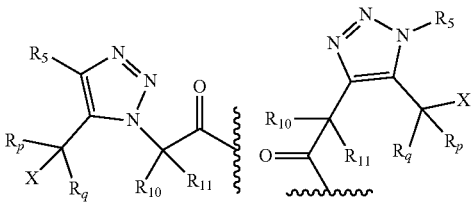

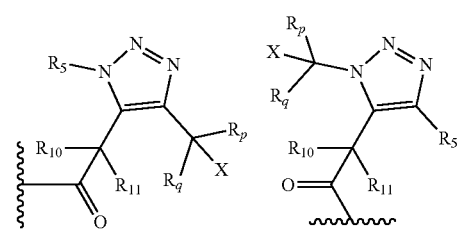

In some embodiments, X is OH or HN—$R_0$;
In some embodiments, X is OH;
In some embodiments, X is HN—$R_0$.
In some embodiments, X is $NH_2$.

In some embodiments, Y is $C(R_pR_q)$, $J_1$ is $C(R_{10}R_{11})$, and one subclass of tetrazole based biodegradable linkers is of the following formulae, wherein all of the variables are the same as defined above:

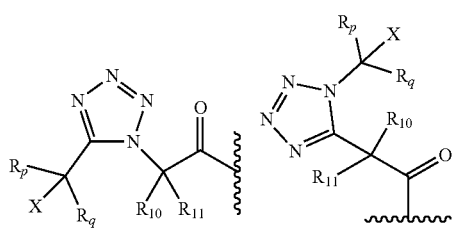

In some embodiments, X is OH or HN—$R_0$;
In some embodiments, X is OH;
In some embodiments, X is HN—$R_0$.
In some embodiments, X is $NH_2$.
In some embodiments, Y is $C(R_pR_q)$, $J_1$ is $C(R_{10}R_{11})$, and one subclass of imidazole based biodegradable linkers is of the following formulae, wherein $R_5$ and $R_6$ are the same as defined above:

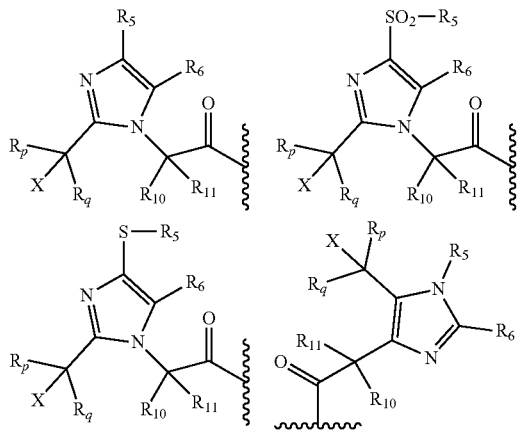

Examples of imidazole based biodegradable linkers include, but are not limited to, the following formulae:

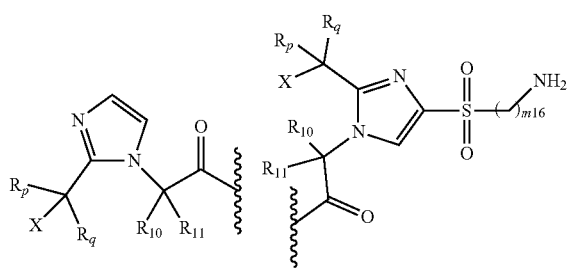

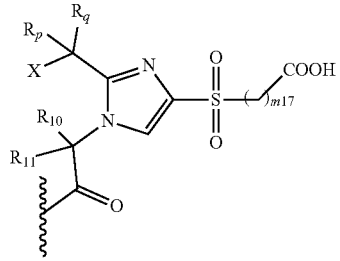

wherein m16 and m17 are each an integer of 1-10.
In some embodiments, X is OH or HN—$R_0$;
In some embodiments, X is OH;
In some embodiments, X is or HN—$R_0$.
In some embodiments, X is $NH_2$.
In some embodiments, Y is $C(R_pR_q)$, $J_1$ is $C(R_{10}R_{11})$, and one class of pyrrole based biodegradable linkers is of the following formulae, wherein $R_5$-$R_7$ are the same as defined above:

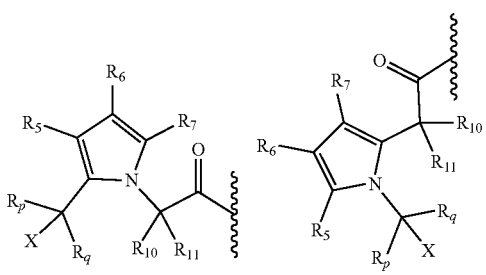

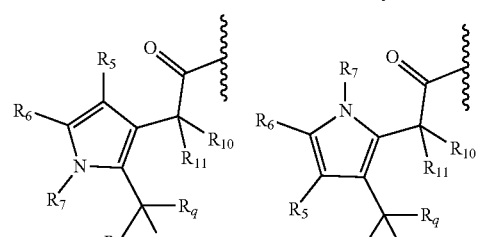

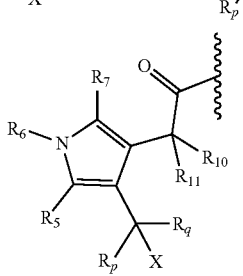

In some embodiments, X is OH or HN—$R_0$;
In some embodiments, X is OH;
In some embodiments, X is HN—$R_0$.
In some embodiments, X is $NH_2$.
In some embodiments, Y is $C(R_pR_q)$, $J_1$ is $C(R_{10}R_{11})$, and one subclass of pyrazole based biodegradable linkers is of the following formulae, wherein $R_5$ and $R_6$ are the same as defined above:

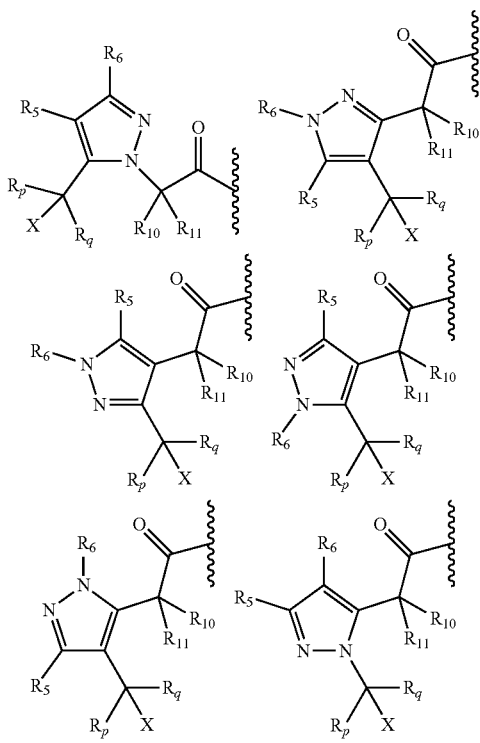

In some embodiments, X is OH or HN—R₀;
In some embodiments, X is OH;
In some embodiments, X is HN—R₀.
In some embodiments, X is NH₂.
In some embodiments, $R_5$ and $R_6$ are a hydrogen (H).
In some embodiments, $Y_1$ and $J_1$ are a bond, and one subclass of biodegradable linkers is of the following formula:

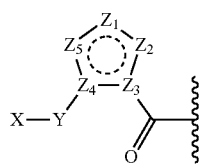

In some embodiments, Y is $C(R_pR_q)$.

In some embodiments, a subclass of triazole based biodegradable linkers is of the following formula, wherein $R_5$ is the same as defined above:

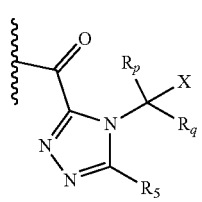

In some embodiments, a subclass of triazole based biodegradable linkers is of the following formula, wherein $R_5$ is the same as defined above:

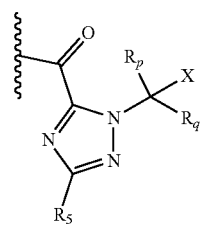

In some embodiments, a subclass of triazole based biodegradable linkers is of the following formulae, wherein $R_5$ is the same as defined above:

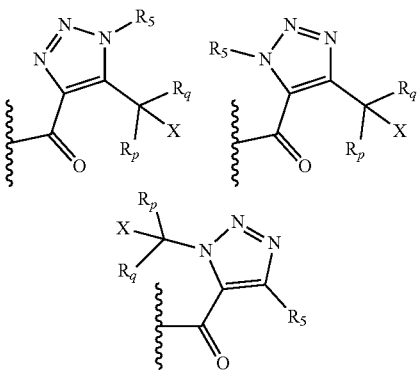

In some embodiments, a subclass of tetrazole based biodegradable linkers is of the following formula:

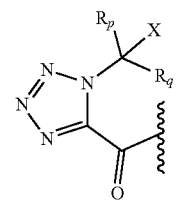

In some embodiments, a subclass of imidazole based biodegradable linkers is of the following formulae, wherein $R_5$ and $R_6$ are the same as defined above:

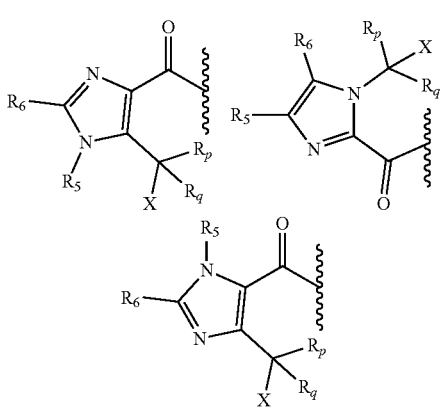

In some embodiments a subclass of pyrrole based biodegradable linkers is of the following formulae wherein $R_5$-$R_7$ are the same as those defined above:

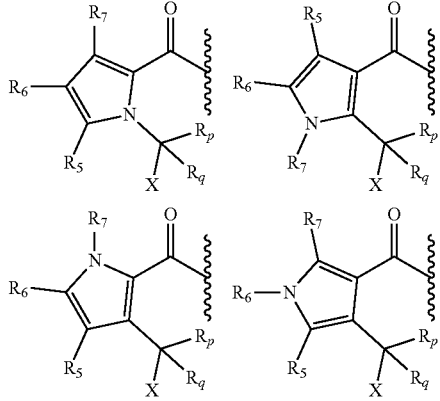

In some embodiments, a subclass of pyrazole based biodegradable linkers is of the following formulae, wherein $R_5$ and $R_6$ are the same as defined above:

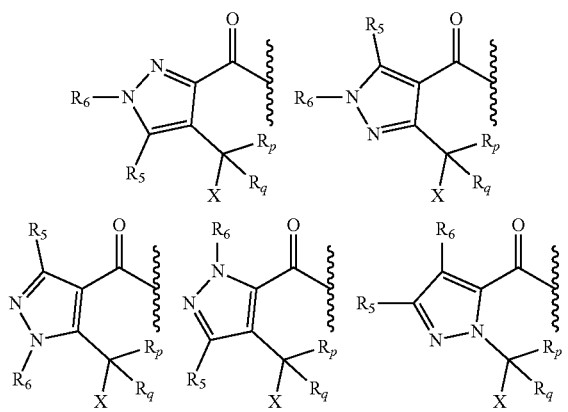

In some embodiments, X is OH or HN—$R_0$.

In some embodiments, X is OH.

In some embodiments, X is HN—$R_0$.

In some embodiments, X is $NH_2$.

In some embodiments, $Y_1$ is $C(R_3R_4)$, and one class of biodegradable linkers is of the following formula:

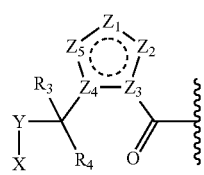

In some embodiments, Y is $C(R_pR_q)$.

In some embodiments, a subclass of triazole based biodegradable linkers is of the following formula, wherein $R_5$ is the same as defined above:

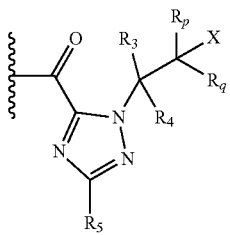

In some embodiments, a subclass of triazole based biodegradable linkers is of the following formula, wherein $R_5$ is the same as defined above:

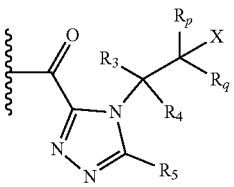

In some embodiments, a subclass of triazole based biodegradable linkers is of the following formulae, wherein $R_5$ is the same as defined above:

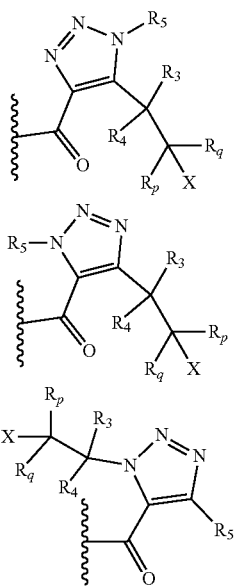

In some embodiments, a subclass of tetrazole based biodegradable linkers is of the following formula:

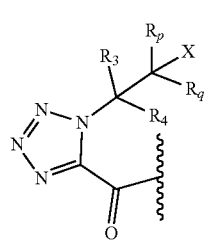

In some embodiments, a class of imidazole based biodegradable linkers is of the following formulae, wherein $R_5$ and $R_6$ are the same as defined above:

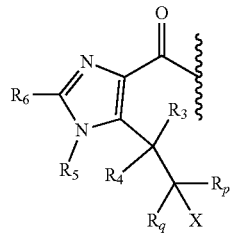

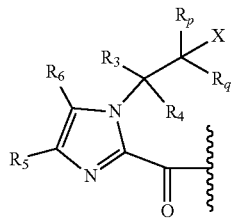

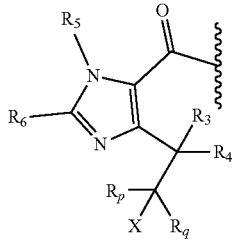

In some embodiments, a subclass of pyrrole based biodegradable linkers is of the following formulae, wherein $R_6$ and $R_7$ are the same as those defined above:

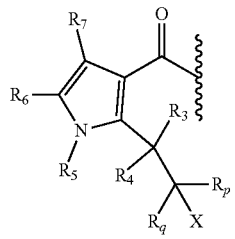

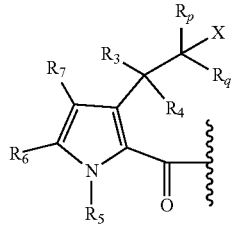

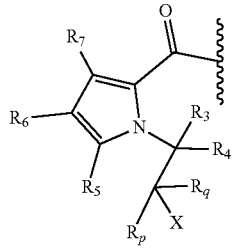

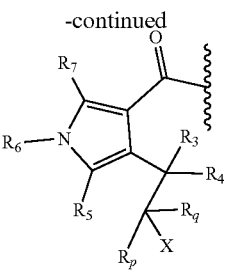

In some embodiments, a subclass of pyrazole based biodegradable linkers is the following formulae, wherein $R_5$ and $R_6$ are the same as defined above:

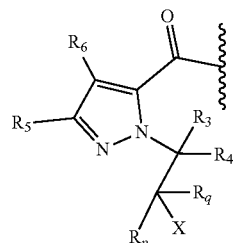

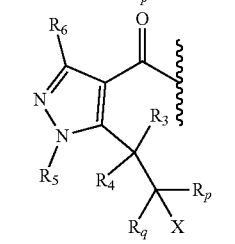

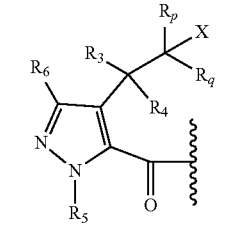

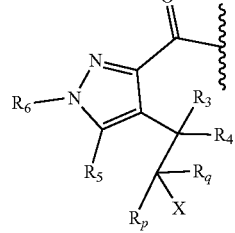

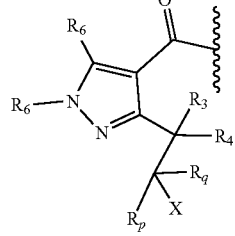

In some embodiments, X is OH or HN—$R_0$.
In some embodiments, X is OH.
In some embodiments, X is HN—$R_0$.
In some embodiments, X is $NH_2$.

Subclass 10

In some embodiments, $Y_1$ is C(O), and one subclass of biodegradable linkers is of the following formula:

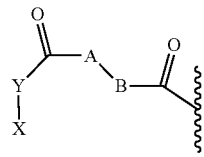

wherein X is OH or HN—$R_O$;

Y is:

(1) N—$R_O$;

(2) C($R_p R_q$);

(3) O, with the proviso that X is not OH;

(4) C($R_p R_q$), when X is HN—$R_O$, $R_O$ and $R_p$ together with the atoms to which they are attached form a 4, 5, or 6 membered heterocyclic ring;

wherein A, B, Ro, $R_O$, $R_p$, and $R_q$ are the same as defined above.

In some embodiments, biodegradable linkers in this subclass are of the following formula:

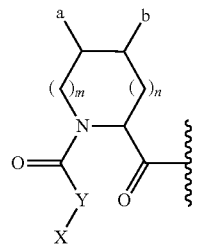

wherein a and b are the same as defined above, m and n are an integer independently selected from 0, 1, 2, 3, 4, 5, and 6.

In some embodiments, biodegradable linkers in this subclass are of the following formulae, wherein $R_5$ and $R_6$ are the same as defined above:

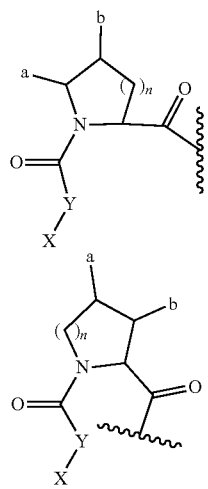

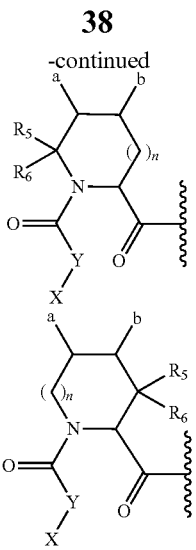

In some embodiments, Y is C($R_p R_q$), and biodegradable linkers in this subclass are of the following formulae, wherein $R_5$ and $R_6$ are the same as defined above:

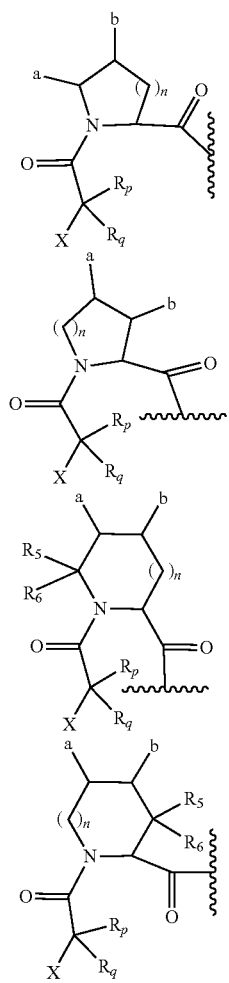

In some embodiments, X, Y, and $Y_1$ (C(O)) constitute a natural or unnatural amino acid or hydroxyl acid. Non limiting examples include alanine, arginine, asparagine, aspartic acid, cysteine, glycine, glutamic acid, histidine, isoleucine, leucine, lysine, methionine, proline, glutamine, phenylalanine, serine, threonine, valine, tryptophan, tyrosine, aminoisobutyric acid, sarcosine, glycolic acid, and phenyllactic acid.

Examples of biodegradable linkers in this subclass include, but not limited to:

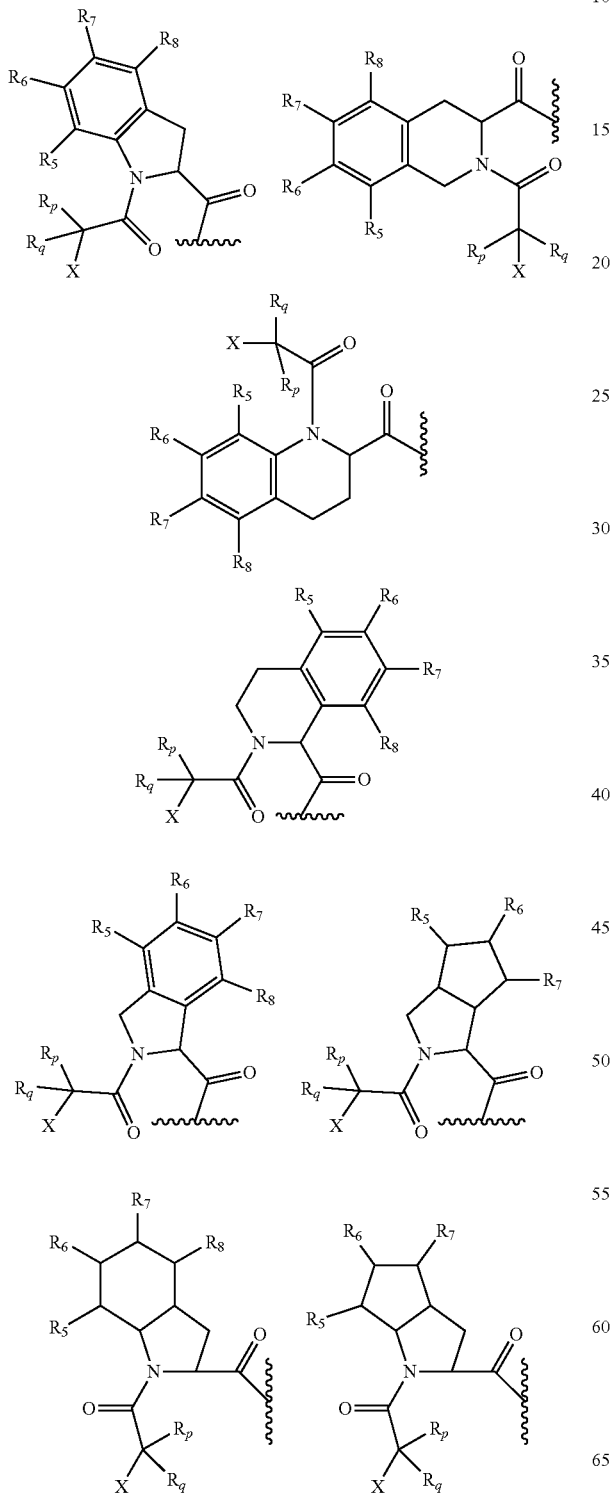
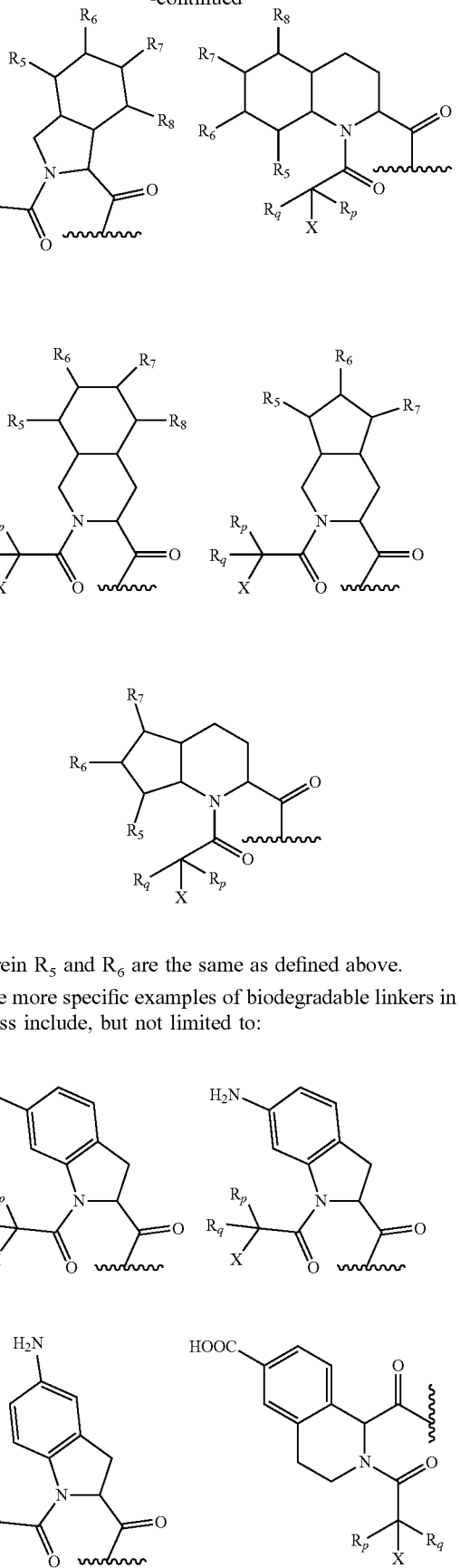

wherein $R_5$ and $R_6$ are the same as defined above.

Some more specific examples of biodegradable linkers in this class include, but not limited to:

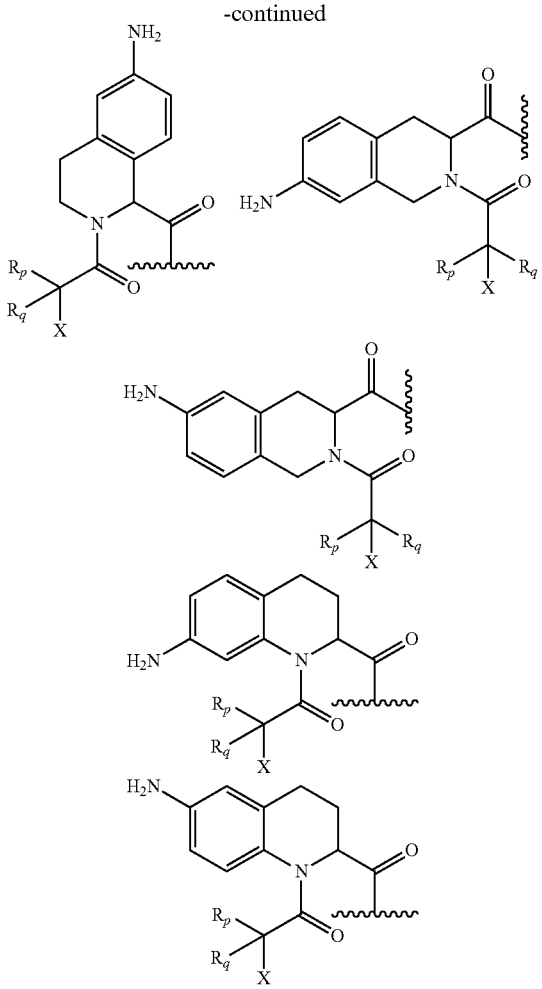

In some embodiments, X is OH or HN—R$_0$.
In some embodiments, X is OH.
In some embodiments, X is HN—R$_0$.
In some embodiments, X is NH$_2$.
In some embodiments, two R groups (selected from R$_0$, R$_3$, R$_4$, R$_5$, R$_6$, R$_7$, R$_8$, R$_9$, R$_{10}$, R$_{11}$, R$_{12}$, R$_{13}$, R$_O$, R$_n$, R$_p$, R$_q$) connected to the same atom or two atoms separated by a bond, together with the atoms to which they are attached, form a C$_4$-C$_{10}$ cycloalkyl group, cycloalkenyl group, cycloalkynyl group; a saturated or unsaturated monocyclic, polycyclic and fused rings, optionally substituted with the at least one group other than hydrogen atom (H); saturated or unsaturated monoheterocyclic, polyheterocyclic and fused heterocyclic ring, optionally substituted with the at least one group other than hydrogen atom (H); or two R groups together with the atoms to which they are attached form a monoaromatic or polyaromatic ring, optionally substituted with the at least one group other than hydrogen atom (H). The at least one group is selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate (or salt), isothiocyanate, thiocyanate (or salt), lower alkylthio, amino, imino, amino lower alkyl, lower alkylamino, lower dialkylamino, hydroxyl, hydroxyl alkyl, nitro, nitrile, isonitrile, pyridyl, azido, carboxyl, carboxamido, acetic acid, thioalkyl, carbonate (or salt), carbamate, loweralkylcarbamyl, diloweralkylcarbamyl, sulfonic acid group, sulfonamide group, sulfonate group (or salt), sulfonyl group, sulfoxide group, sulfide group, disulfide group, mercapto (or sulfhydryl) group.

In some embodiments, R$_5$, R$_6$, R$_7$, R$_8$, R$_9$, R$_{10}$, R$_{11}$, R$_{12}$, R$_{13}$, R$_p$, R$_q$ comprise at least a functional group which can form a covalent bond with a reactive polymer in order to connect one or more reactive polymers.

The hydrogels in the present invention can be composed of backbone moieties and optional crosslinking moieties.

A backbone moiety is characterized by having a branching core, from which at least two chains extend, preferably 2-16, more preferably 4-8. Such branching cores may be comprised of poly- or oligoalcohols in bound form, preferably pentaerythritol, tripentaerythritol, hexaglycerin, sorbitol, mannitol, polyvinyl alcohol, trimethylolpropane, sucrose, fructose, glucose, dextran, cellulose, starch, amylose, hyaluronic acid, or branching cores may be comprised of poly- or oligoamines such as ornithine, diaminobutyric acid, trilysine, tetralysine, pentalysine, hexalysine, heptalysine, octalysine, nonalysine, docalysine or oligomeric lysine in bound form.

Chains extending from the branching core can be of any length. In some embodiments, the backbone chain atoms are all carbon atoms. In some embodiments, the backbone chain atoms are selected from C, O, N and S, and the chain atoms can be selected based on their expected solubility to provide a chain with more suitable solubility. In some embodiments a chain comprises optional linking groups which can be degraded by enzymes or cleaved automatically under in vivo conditions. In some embodiments the chains are composed of several fragments connected by ester bonds or amide bonds. Chains include but are not limited to, PEG, long chain fatty acid, natural or unnatural amino acid (e.g. β-alanine, γ-aminobutyric acid, γ-glutamic acid), short peptides (e.g. R-alanine-β-alanine, γ-glutamic acid-γ-glutamic acid), or a combination of two or more above (e.g. optional long chain fatty acids, PEGs, amino acids, short peptides linked by covalent bonds to form a long chain). In some embodiments chains can be peptides of any length. An exemplary chain is from about 1 to 50 amino acids in length, 5-50, 3-5, 5-10, or 5-15 amino acids in length. In some embodiments, chains are polylysines, polyglutamic acids, polyaspartic acids, copolymers of these amino acids, and mixed polymers of these amino acids and other amino acids such as serine.

PEG-based polymeric chains are preferred. PEG-based polymeric chains may be linear, branched, or forked. One end of a PEG polymeric chain is attached to the core while the other end is connected to the structure having at least one crosslinking functional group and at least one optional reactive functional group. In some embodiments such a structure has hyperbranched moieties. Structures of polymeric chains may be identical or different. The number of PEG units in each polymeric chain may vary. A PEG-based polymeric chain may comprise alkyl groups, aryl groups, and heteroatoms. Hyperbranched moieties provide more functional groups. In some embodiments additional functional groups in hyperbranched moieties increase the number and density of the crosslinking functional groups. In some embodiments, additional functional group in hyperbranched moieties may enhance drug loading.

Preferred structures for PEG based polymeric chains extending from a branching core are multi-arm PEG derivatives such as 4-arm and 8-arm PEG derivatives provided by commercial vendors. It is preferred that the sum of crosslinking functional groups and reactive functional groups is equally divided by the number of PEG based polymeric chains extending from the branching core so that each PEG based polymeric chain has the same number of crosslinking functional groups and reactive functional groups.

In some embodiments the hydrogel backbone of the present invention is of the formula J(L$_1$-B$_1$)$_{n1}$, wherein J is the branching core; L$_1$ is a chain extending therefrom and two ends are covalently connected to J and B$_1$ respectively. L$_1$ may be a linear chain, a branched chain, or a forked chain.

In some embodiments the backbone chain atoms are all carbon atoms. In some embodiments backbone chain atoms are selected from C, O, N and S, and the chain atoms can be selected based on their expected solubility to provide a chain with more suitable solubility. In some embodiments, $L_1$ may comprise optional linkers which can be degraded by enzymes or cleaved automatically under in vivo conditions. $L_1$ may include but are not limited to, PEG, long chain fatty acid, natural or unnatural amino acid (e.g. β-alanine, γ-aminobutyric acid, γ-glutamic acid), short peptides (e.g. @-alanine-@-alanine, γ-glutamic acid-γ-glutamic acid), or a combination of two or more above (e.g. optional long chain fatty acids, PEGs, amino acids, short peptides linked by covalent bonds to form a long chain). Preferably, $L_1$ is a PEG-based polymeric chain. More preferably, each $L_1$ is independently selected from formula $-(CH_2)_{n4}(OCH_2CH_2)_nL_{n5}$ or $-(CH_2)_{n4}(CH_2CH_2O)_nL_{n5}$, wherein n4 is an integer of 0-5, n is an integer of 1-1000, $L_{n5}$ is a bond or a functional group connecting terminus of $L_1$ and $B_1$. In some embodiments $L_1$ is a peptide of any length. In some embodiments, $L_1$ is polylysine, polyglutamic acid, polyaspartic acid, copolymers of these amino acids, and mixed polymers of these amino acids and other amino acids such as serine. $B_1$ is a structure having at least one crosslinking functional group $C_2$ and at least one optional reactive functional group $C_1$. Reactive functional groups and crosslinking functional groups may be identical or different. Functional groups on the same backbone do not react with one another. n1 is an integer of 2-16. Each $L_1$ and $B_1$ can be selected independently. In some embodiments $B_1$ has optional hyperbranched moieties, thereby providing a plurality of crosslinking functional groups and reactive functional groups. In some embodiments $B_1$ has a dendritic structure. Preferably $L_1$ and B1 are connected by an amide bond.

In one embodiment a 4-arm hydrogel backbone moiety is of following formula:

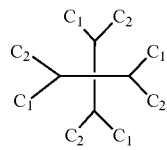

wherein $C_1$ is a reactive functional group, $C_2$ is a crosslinking functional group. In some embodiments $C_2$ undergoes an orthogonal reaction with a crosslinking functional group on a crosslinking moiety whereas $C_1$ does not react with crosslinking functional groups on a crosslinking moiety.

In some embodiments a hydrogel backbone moiety is of Formula $(C_1-L_1)_{n2}J(L_1-C_2)_{n3}$, wherein J is the branching core; $L_1$ is a chain extending therefrom; $C_1$ is a reactive functional group, $C_2$ is a crosslinking functional group. Reactive functional groups and crosslinking functional groups may be identical or different, and functional groups on the same backbone do not react with each other; n2 and n3 are an integer of 0-16.

Preferably hydrogel backbone moiety of the present invention is of the formula $(C_1-L_1)_4J(L_1-C_2)_4$, wherein J is a branching core, e.g. hexaglycerin and tripentaerythritol; $L_1$ is a chain extending therefrom; $C_1$ is a reactive functional group; $C_2$ is a crosslinking functional group. Preferably, $L_1$ is a PEG-based polymeric chain. More preferably, each $L_1$ is independently selected from the formula $(CH_2)_{n4}(OCH_2CH_2)_nL_{n5}$ or $-(CH_2)_{n4}(CH_2CH_2O)_nL_{n5}$, wherein n4 is an integer of 0-5, n is an integer of 1-1000, $L_{n5}$ is a bond or a chemical functional group connecting terminus of $L_1$ and $C_1$, $C_2$. Preferably, $L_1$ and $C_1$, $C_2$ are connected by an amide bond. Each $C_1$ and $C_2$ in backbone moiety $(C_1-L_1)_4J(L-C_2)_4$ is independently selected. In one embodiment, an 8-arm hydrogel backbone moiety is of following structure:

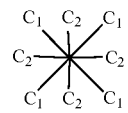

In some embodiments $C_1$ and $C_2$ are connected to forked or hyperbranched structures such as the following $B_1$. Preferably, $B_1$ is a highly branched polypeptide. In some embodiments the highly branched polypeptide comprises one or more lysines. One exemplary example is as follows:

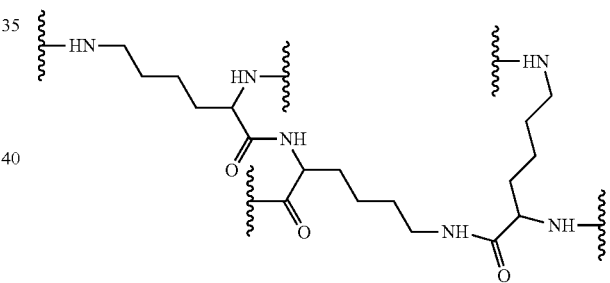

A wavy line represents connection with another moiety by a covalent bond. Lysine may be in L or D form. D-lysine tends to better resists enzymatic hydrolysis.

A preferred backbone moiety is as shown:

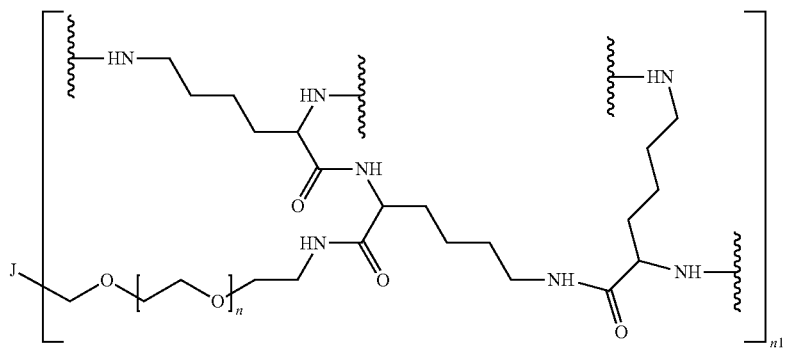

wherein J is a branching core. The number of lysine residues in each branch may be increased or decreased as required. Some of amino groups of lysine residues can be used for crosslinking and some used for loading of biologically active substances.

Preferably, the backbone moiety has a molecular weight in range of 1-40 kDa, preferably 5-kDa.

A crosslinking moiety comprises at least two crosslinking functional groups and optionally at least one optional biodegradable linker. In some embodiments a crosslinking functional group is connected to a crosslinking moiety via a biodegradable linker. A chain may be inserted between a crosslinking functional group and a biodegradable linker as needed. The crosslinking functional group of crosslinking moiety is capable of forming a covalent bond with the crosslinking functional group of hydrogel backbone moiety. The crosslinking functional groups may be identical or different (heterobifunctional). A crosslinking functional group of the heterobifunctional crosslinking moiety reacts with a crosslinking functional group on the hydrogel backbone moiety, and another functional group reacts with a crosslinking functional group on the same or a different hydrogel backbone moiety. In some embodiments, a crosslinking moiety comprises more than one biodegradable linkers. These biodegradable linkers may be identical or different. Functional groups on the same crosslinking moiety do not react with each other.

A crosslinking moiety may be a chain, for example, $C_4-Z_2-L_2-C_4$, $C_4-Z_2-L_2-Z_2-C_4$, $C_4-Z_2-L_2-C_4'$, $C_4-Z_2-L_2-Z_2-C_4'$ or $C_4-Z_2-L_2-Z_2'-C_4'$, wherein $L_2$ is connected to chains on both sides, $C_4$ and $C_4'$ are a crosslinking functional group, $Z_2$, and $Z_2'$ are an optionally biodegradable linker. A chain may be inserted between $C_4$ and $Z_2$, $C_4'$ and $Z_2'$.

A crosslinking moiety may be a multi-arm structure, e.g., a 4-arm structure, an 8-arm structure. The formula is $O(L_2-Z_2-C_4)_{n6}$, wherein 0 is a branching core, $L_2$ is a chain extending therefrom, $C_4$ is a crosslinking functional group, $Z_2$ is an optionally biodegradable linker, n6 is an integer of 2-8. $Z_2$ in each branch may be identical or different. $C_4$ in each branch may be identical or different. In one embodiment a 4-arm crosslinking moiety is as follows:

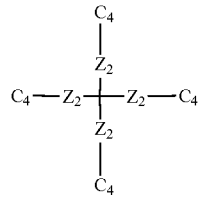

In some embodiments $C_4$ is absent, and $Z_2$ may react directly with a crosslinking functional group of the backbone moiety to form a covalent bond.

Crosslinking functional groups on a hydrogel backbone moiety of the present invention and crosslinking functional groups at corresponding sites of a crosslinking moiety are cognate reactive pairs. Some commonly used, non-limiting examples of cognate reactive pairs of functional groups include:

An amine can react with carboxylic acids, aldehydes and ketones.

A mercapto group can participate in thiol-Ene reactions. A mercapto group can react with maleimide, iodoacetic acid, vinyl sulfone, vinyl sulfonamide, acrylamides, acrylates, halogenated carbonyl group, and enone.

An azide compound may react with an alkynyl group (for example, alkynes of 2 to 20 carbon atoms, cyclooctyne, arylalkynyl), bicyclononyne (BCN), and maleimide. In click chemistry reactions azide-alkyne cycloaddition reaction comprises copper-catalyzed cycloaddition reactions and strain-promoted reactions. Commonly used functional groups in strain-promoted reactions include dibenzocyclooctyne (DBCO), monofluorocyclooctyne (MFCO), difluorinated cyclooctyne (DIFO) and aryl-less cyclooctyne (ALO), which vary over a ~1000 fold range in reaction rates with an azide compound (DBCO>MFCO>ALO). Thus, in the presence of more than one cyclooctyne functional groups an azide compound may selectively react with one or a few specific cyclooctyne functional groups, for example, react with DBCO first. In another class of strain-promoted reactions azide compounds react with bicyclononyne compounds.

Nitrones may react with alkynyl (e.g. cyclooctyne) and bicyclononyne compounds.

In Diels—Alder cycloaddition reaction, for example, maleimide can react with 1,3-dienes, furan, cyclopentadiene.

Tetrazine may react with an olefin. For example, 4-(6-methyl-1,2,4,5-tetrazine) phenylacetic acid reacts with norbornene by the inverse electron demand Diels—Alder cycloaddition reaction. Further, tetrazine may react with a trans-cyclooctene (TCO).

Condensation of an alkoxyamine with a ketone, e.g. pyruvamide, gives an oxime. An aldehyde can react with a hydroxylamine or a hydrazide.

Olefins and tetrazole undergoes light reaction. A bisthioester may react with a diene. Anthracene can react with maleimide.

Any chemical reactions known in the art may be applied to crosslinking, including acylation, reductive alkylation, Michael addition, thiol alkylation or chemoselective conjugation or connection through a reactive functional group on a molecule (e.g., an aldehyde, amino, ester, sulfhydryl, α-haloacetyl, maleimide, N-hydroxysuccinimide ester or hydrazino group) to another reactive functional group (e.g., an aldehyde, amino, ester, thiol, α-haloacetyl, maleimide, N-hydroxysuccinimide ester or hydrazino group) on the same or a different molecule. Activating groups used in the reactions include, but are not limited to, N-hydroxysuccinimide ester, sulfone, maleimide, triflate, tresylate, azidirine, oxirane, and 5-pyridyl.

In some embodiments, hydrogel backbone moieties are directly connected through biodegradable bonds or linkers and need not a crosslinking moiety. In some embodiments a backbone moiety is connected to a crosslinking moiety. Each crosslinking moiety comprises at least a biodegradable linker. Biodegradable hydrogels may contain one or more types of crosslinking moieties.

In some embodiments, a crosslinking moiety comprises at least two crosslinking functional groups, at least one biodegradable linker and at least one optional reactive functional group. In some embodiments, a crosslinking functional group or reactive functional group is connected to a crosslinking moiety via a biodegradable linker. A chain may be incorporated between a biodegradable linker and a crosslinking functional group or a reactive functional group as needed. A crosslinking functional group of a crosslinking moiety form a covalent bond with a crosslinking functional group on the hydrogel backbone moiety. The crosslinking functional groups may be identical or different (heterobifunctional). The first crosslinking functional group on a heterobifunctional crosslinking moiety reacts with a crosslinking functional groups of the hydrogel backbone moiety, and the second crosslinking functional group reacts with a crosslinking group on the same or a different hydrogel backbone moiety. Functional group on the crosslinking moiety do not react with each other.

This crosslinking moiety may be a chain. In some embodiments a crosslinking moiety is of formulae $B_2$—$Z_2$-$L_2$-$Z_2$—$B_2$, $B_2$—$Z_2$-$L_2$-$B_2$, $B_2$—$Z_2$-$L_2$-$Z_2$—$B_2'$, or $B_2$—$Z_2$-$L_2$-$Z_2'$—$B_2$, wherein $L_2$ is a chain connecting both sides, $B_2$, and $B_2'$ each having at least one crosslinking functional group and at least one optional reactive functional group. In some embodiments $B_2$ or $B_2'$ has an optional hyperbranched substructure, thereby providing a plurality of crosslinking functional groups and reactive functional groups. $Z_2$ and $Z_2'$ are optional biodegradable linkers. $B_2$ and $B_2'$, $Z_2$ and $Z_2'$ may be identical or different. In one embodiment a crosslinking moiety chain has the following structure:

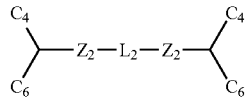

wherein $Z_2$ is an optional biodegradable linker, $C_4$ is a crosslinking functional group, $C_6$ is reactive functional group.

$B_2$ or $B_2'$ may comprise one or more optional biodegradable linkers in its branched structure.

In some embodiments a crosslinking moiety chain has the following structures:

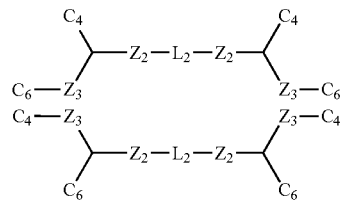

wherein $Z_2$ and $Z_3$ are optional biodegradable linkers, $C_4$ is a crosslinking functional group, $C_6$ is a reactive functional group. In some embodiments, $Z_2$ has a longer degradation half-life than $Z_3$.

In some embodiments, the crosslinking moiety is of formula $B_2$-$L_2$-$B_2$ or $B_2$-$L_2$-$B_2'$, wherein $L_2$ is a chain connecting both sides, $B_2$ and $B_2'$ have at least a crosslinking functional group and at least an optional reactive functional group, and a crosslinking functional group and a reactive functional group can be respectively coupled to an optional biodegradable linker. Functional groups on the same crosslinking moiety do not react with each other. In one embodiment a crosslinking moiety chain has the following structure:

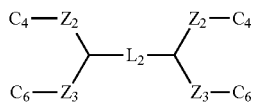

In one embodiment, a PEG-based crosslinking moiety chain with branching substructures (excluding optional biodegradable linkers and reactive or crosslinking functional groups to which they are attached) has the following structure:

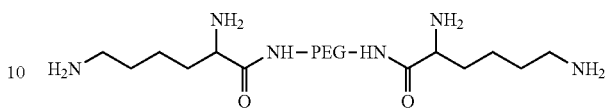

In some embodiments, the crosslinking moiety is of formula $O(L_2$-$Z_2$—$B_2)_{n6}$, wherein O is a branching core, $L_2$ is the chain extending therefrom, $Z_2$ is an optional biodegradable linker, $B_2$ having at least a crosslinkable functional group and at least an optional reactive functional group, and a reactive functional group or a crosslinkable functional group can be attached to an optional biodegradable linker. In some embodiment $B_2$ has an optional hyperbranched substructure, thereby providing a plurality of crosslinkable functional groups and reactive functional groups. In some embodiments, $B_2$ has a dendritic polymeric structure. n6 is an integer of 2-8. Preferably, $L_2$ is a PEG-based polymeric chain, both ends of which are covalently attached the braching core and $Z_2$ respectively. More preferably, each $L_2$ is independently selected from the formula $(CH_2)_{n4}(OCH_2CH_2)_nL_{n5}$ or $(CH_2)_{n4}(CH_2CH_2O)_nL_{n5}$, wherein n4 is an integer of 0-5, n is an integer of 1-1000, Los is a bond or a chemical functional group connecting the end of $L_2$ and $Z_2$. Preferably, $L_2$ and $Z_2$ are linked via an amide bond. Each $Z_2$ and $B_2$ of $O(L_2$-$Z_2$—$B_2)_4$ can be selected independently.

$B_2$ may comprise one or more optional biodegradable linker in its branched structure. In one embodiment, a 4-arm crosslinking moiety has the following structure:

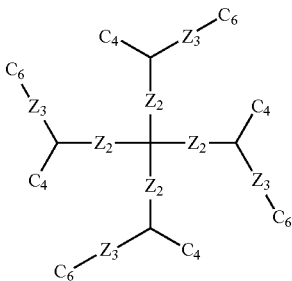

wherein $Z_2$, $Z_3$, $C_4$ and $C_6$ are the same as defined above. In some embodiments, $Z_2$ has a longer degradation half-life than $Z_3$.

In some embodiments, the crosslinking moiety is of formula $O(L_2$-$B_2)_{n6}$, wherein n6 is an integer of 2-8, $B_2$ has at least a crosslinkable functional group and at least an optional reactive functional group. Crosslinkable functional groups and reactive functional groups may be respectively connected with optional biodegradable linkers. In one embodiment a 4-arm crosslinking moiety has the following structure:

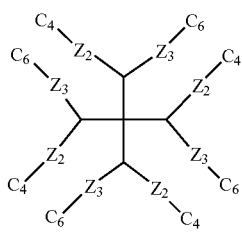

In some embodiments $C_4$ or $C_6$ is absent, $Z_2$ and $Z_3$ may react directly with the functional groups of the backbone moiety to form a covalent bond.

In one embodiment, a multi-arm PEG-based crosslinking moiety with branching substructures (excluding optional biodegradable linkers and reactive or crosslinking functional groups to which they are attached) has the following structure:

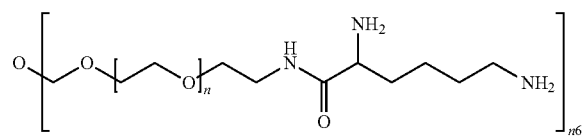

In some embodiments, monomers which are composed of the polymeric crosslinking moiety are connected through biodegradable bonds. Examples of the crosslinking moieties include polymers based on polyglycolic acid or polylactic acid.

In a "4×4" hydrogel crosslinking functional groups of the hydrogel backbone moiety and crosslinking functional groups of the four-arm crosslinking moiety react to form a network structure. Preferably, the hydrogel backbone moiety and crosslinking moiety are four-arm kDa PEG based. A non-limiting example is as follows:

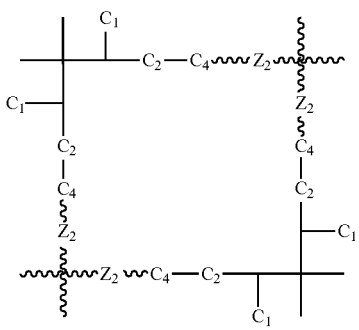

wherein $C_2$ is a crosslinking functional group of a hydrogel backbone moiety. $C_2$ and the crosslinking functional group $C_4$ at the corresponding site of crosslinking moiety are cognate reactive pairs. $C_1$ is a reactive functional group of hydrogel backbone moiety, $Z_2$ is an optional biodegradable linker.

Reactive functional groups of hydrogel backbone moiety and crosslinking moiety can have multiple functions, such as loading a biologically active substance or a biomarker. These functional groups can be used directly, or can be used after transformation or conversion into other orthogonal reactive functional groups.

In clinical applications, in order to reduce or avoid subcutaneous tissue reaction to a hydrogel subcutaneous injection doses of the hydrogel should be as small as possible, thus hydrogels with a high drug loading capacity are desired. Even if hydrogel backbone moiety comprises hyperbranched substructures, steric hindrance may affect the backbone loading when a drug molecule is large. In some embodiments of the present invention a crosslinking moiety comprises branched or bifurcated substructures, increasing the number of reactive functional groups, and reduces steric hindrance by using lengths of branched or bifurcated substructures, thus drug loading potential of hydrogels is significantly enhanced.

In the present invention, a biologically active substance may be connected to a biodegradable linker which is conjugated to a hydrogel via an optional reactive functional group, thus the biologically active substance is loaded on the hydrogel. In some embodiments, a biologically active substance in the present invention may be connected to a biodegradable linker via a nitrogen-containing (e.g. an amino group) or a hydroxyl-containing functional group, and the linker is coupled to a hydrogel via an optional reactive functional group. Connection mode is hydrogel-optional reaction functional group—biodegradable linker—biologically active substance.

In some embodiments, an optional reactive functional group of a four-arm hydrogel backbone moiety is connected to a biologically active substance via a biodegradable linker. A non-limiting example is as follows:

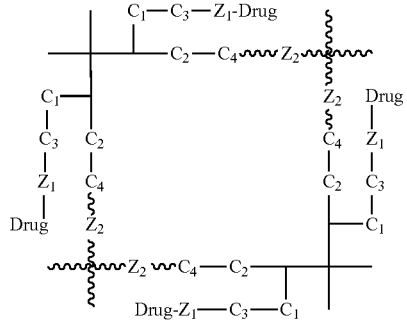

wherein $C_2$ is a crosslinking functional group on a hydrogel backbone moiety, and $C_2$ and the crosslinking functional group $C_4$ at the corresponding site of a crosslinking moiety are cognate reactive pairs. $C_1$ is a reactive functional group of a hydrogel backbone moiety, $C_1$ and reactive functional group $C_3$ are cognate reactive pairs. $Z_1$ and $Z_2$ are an optionally biodegradable linker. Drug represents a biologically active substance. In some embodiments, $C_3$ is absent, $Z_1$-drug and $C_1$ are connected via a covalent bond.

It is preferred that most of biologically active substances (>90%) loaded on hydrogels of the present invention are released before a significant amount of backbone moieties decompose (<10%). This can be achieved by introducing biodegradable linkers of different half-lives in crosslinking moieties between backbone moieties and in a chain connecting a hydrogel backbone moiety and a biologically active substance. The half-lives of biodegradable linkers used in crosslinking moieties between hydrogel backbone moieties are longer.

In a "8×4" hydrogel four crosslinking functional groups on an eight-arm hydrogel backbone moiety react with four crosslinking functional groups on a four-arm crosslinking moiety to form a network structure. Preferably, a hydrogel backbone moiety is based on a 40 kDa eight-arm PEG and a crosslinking moiety is based on a 20 kDa four-arm PEG. A non-limiting example is as follows:

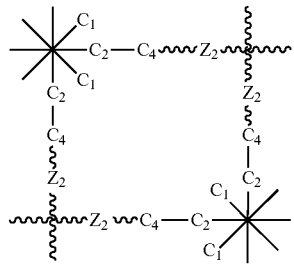

The remaining four reactive functional groups $C_1$ in an eight-arm hydrogel backbone moiety can be connected to biologically active substances via biodegradable linkers.

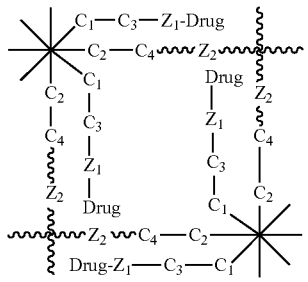

wherein $C_1$, $C_2$, $C_3$, $C_4$, $Z_1$, $Z_2$ and Drug are the same as defined above.

The hydrogels in the present invention is hydrolyzed in vivo through hydrolysis of biodegradable bonds either in a backbone moiety or a crosslinking moiety, or both in a backbone moiety and a crosslinking moiety.

Biodegradable linkers of the present invention connect two hydrogel backbone moieties or a hydrogel backbone moiety and a crosslinking moiety with amide bonds. Amide bonds are the most stable chemical bond in vivo. A hydrogel backbone moiety or a crosslinking moiety based on polyethylene glycol or polypropylene glycol typically does not contain a cleavage site of the enzymes in vivo. Accordingly, hydrogels constructed in this manner in the present invention have good stability in vivo, and their degradation rates are determined by biodegradable linkers. To our knowledge, this is the first set of hydrogels constructed with amide bonds and degraded automatically by cleavage of amide bonds.

Hydrogels using conventional non-covalent encapsulation method are typically degrade by hydrolysis of crosslinked ester bonds, releasing biologically active substances. Hydrogels using covalent depot usually employ a large number of ester bonds in the backbone to facilitate degradation, and a biologically active substance is often connected to a hydrogel by an ester bond. Hydrolysis rates of the ester bonds in a polymer vary in a narrow range, and the network structure and chemistry play a greater role in the degradation rate of a hydrogel. Thus, a delivery system needs to be optimized separately for each biologically active substance. Hydrogels in the present invention have an advantage of making use of linkers which are biodegradable under physiological conditions and do not require enzymatic catalysis. A hydrogel backbone moiety of the present invention may comprise biodegradable linkers, or backbone moieties are connected via biodegradable linkers, or backbone moieties are connected via crosslinking moieties containing biodegradable linkers. Chemistry and network structures of hydrogels remain substantially constant, so that the rates of hydrogel degradation and release of a biologically active substance depend on cleavage kinetics of biodegradable linkers. A biodegradable linker with an appropriate rate of degradation can be selected according to the requirements of administration. The present invention provides biodegradable linkers with a very wide range of half lives to meet different clinical needs. These hydrogel systems do not require optimization of polymer structures for each biologically active substance. Properties of carrier materials, e.g. biocompatibility (minimal irritation, immunogenicity, toxicity, etc.) can be independently optimized in addition to biologically active substance release properties.

Traditional drug encapsulation systems display early stage "burst release" or late stage "dose dumping", characterized by rapid, uncontrolled release of a biologically active substance from the hydrogel in the beginning and end of degradation. Early burst release can account for 20% of the total amount of the biologically active substance encapsulated. The hydrogel systems of the present invention, whether they are covalent depot methods or noncovalent depot methods, do not have the same problem.

In some embodiments of the present invention a non-covalent encapsulation method is used. The average pore diameter of three-dimensional network in the hydrogel is smaller than the size of the biologically active substance. A biologically active substance such as a drug is encapsulated within the hydrogel without chemical bond connection. In some embodiments, a hydrogel is formed in the presence of a biologically active substance and the biologically active substance is encapsulated in the hydrogel.

In some embodiments of the present invention a covalent depot method is used. If the molecular weight of a biologically active substance is 1~100 KDa, the distance between two hydrogel nodes is not less than 7 nm so that the biologically active substance may pass through pores of the hydrogel. The distance between the cores of two mutually crosslinked PEG-based multi-arm backbone moiety and crosslinking moiety is generally not shorter than the length of a 10 kDa PEG chain. If the loaded biologically active substance is a small molecule compound the distance between two hydrogel nodes should be shorter, and smaller molecular weight multi-arm PEG-based backbone moieties and crosslinking moieties may be used.

A hydrogel of the present invention may provide a single biologically active substance, or a composition of more than one bioactive substances. Biologically active substances in the composition may be used for the treatment of the same disease, or may also be used to treat different diseases. By selecting biodegradable linkers of similar or different half-lives release rates of biologically active substances may be similar or different.

Half-lives of hydrogels are in the range of 1-10000 hours, preferably 1-5000 hours, more preferably 1 to 1000 hours. When ranges are given in the present invention, for example 1-1000 hours, the intermediate interval numbers should be considered as disclosed as if specifically and explicitly set forth. This avoids the necessity of long list of numbers and the present invention intends to includes any arbitrary range between the outer boundaries. For example, the range 1-1000 also includes 1-500 and 100-500.

Enzymatic degradation is an important factor for short duration of action of biological agents, such as a polypeptide or protein, in vivo, and another factor is renal clearance. Commonly used method to increased duration of action of a drug in vivo is to attach a polypeptide or a protein to natural or synthetic macromolecules via hydrolyzable or non-hydrolyzable bonds. Biological macromolecules include albumin, polysaccharides (e.g. dextran), antibodies (e.g., IgG or IgG Fc) and the like. Synthetic macromolecules include polyethylene glycol and the like. Biological activities of drugs tend to be significantly reduced when drugs and macromolecules are connected via a nonhydrolyzable covalent bond. Drugs and macromolecules can be connected via hydrolysable bonds (e.g. ester, carbonate, hydrolyzable carbamate). Commonly used hydrolyzable bonds have low stability and are susceptible to enzymatic degradation or spontaneous hydrolysis in plasma. It is difficult to predict drug release. Further, many biologically active substances, especially small molecular weight drugs, lack suitable functional groups for conjugation with macromolecules. Conjugation or fusion protein method can only reduce enzymatic degradation and renal clearance to some extent. PEG40K is currently largest molecular weight polyethylene glycol, used clinically. Even if molecular weight of polyethylene glycol is increased to 60K or 80K, time that can be prolonged is very limited. However, the molecular weight of polyethylene glycol is so large that the risk of side effects is elevated. Therefore, long action methods dependent upon macromolecules has an insurmountable upper limit of time.

The hydrogels of the present invention use subcutaneous tissues as drug depot, and there is no enzymatic degradation and renal clearance prior to drug release, thus delivery time can be extended to weeks, months, or even years. For existing long-acting drugs multiple doses, or even doses of multi-days, are administered in one input. Initial blood concentrations of drugs are high and toxicity of narrow therapeutic index drugs is enhanced. Design of prodrugs with no biological activities is a solution, but many of the biologically active substances do not have functional groups appropriate for conjugation near their active sites, and a macromolecule conjugated to a functional group at the distal end might not be able to inhibit their activities. Hydrogels of the present invention confine a biologically active substance to the injection site and it cannot reach its target prior to its release, so its biological activity is not shown and the effect is similar to that of a prodrug. Unlike prodrugs, the hydrogels of the present invention can be adapted to various types and location of functional groups of the biologically active substances. Hydrogels slowly release drugs and plasma concentrations of drugs are stable. The safety of drugs with a narrow therapeutic index and the therapeutic effects of drugs can be improved. In addition, due to multiple cysteines or lysines in protein drugs, site specific conjugation is a challenge, and it is almost impossible to obtain a single product. Most pegylated protein drugs have this problem. For example, in ADAGEN® (bovan pegademase) and ONCASPAR® (pegaspargase), potential attachment sites of PEGs include lysines, serines, tyrosines, and histidines. Porcine uricase is a tetramer, each subunit containing 28-29 lysines which may theoretically react with polyethylene glycol. In fact, each subunit can be conjugated to an average of 10-11 PEG10 KDa. Uricase in Krystexxa® (pegloticase) contains an average of 9 polyethylene glycol molecules in each subunit. 8 lysines of INF-α2a may generate eight different products after reaction with polyethylene glycol, wherein there are 3 fold difference in potency between the product with the lowest activity and the product with the highest activity (Foser et al., Protein expression and purification 2003, 30, 78-87). Non-covalent encapsulation method of the present invention does not involve the reaction with a drug, and a drug retains its original sequence and structure in the hydrogel and after drug release. In covalently depot method of the present invention, a drug is covalently attached and attachment sites may not be identical, but a drug still maintains its original sequence and structure after release, which ensures the unity of the actual active drug.

Preparation of Hydrogels

The present invention provides a method for preparing biodegradable hydrogels, and said method comprises reaction of a hydrogel backbone moiety with a crosslinking moiety which contains functional groups capable of reacting with the corresponding sites of the backbone moiety and biodegradable linkers.

In some embodiments, biodegradable hydrogels are prepared by reaction of identical backbone moieties with biodegradable crosslinking moieties. The backbone moiety is multivalent and is able to form nodes in the three dimensional hydrogel matrix. One example is a reaction of a multi-arm PEG with a crosslinking agent to generate a hydrogel. Multi-arm PEG reagents having different functional groups and molecular weights are commercially available. Another example is a reaction of a linear polymer with a crosslinking moiety to form a hydrogel. Examples of linear polymers include hyaluronic acid, polyvinyl alcohol, carboxymethyl cellulose, poly (2-hydroxyethyl methacrylate), dextran, chitosan, collagen, alginate and agarose.

In some embodiments, the present invention provides a method of preparing biodegradable hydrogels by reaction of more than one type of backbone moieties with biodegradable crosslinking moieties. Biodegradable crosslinking moieties comprise functional group 1 that reacts with the first backbone moiety, and functional group 2 that reacts with the second backbone moiety, and biodegradable linkers. Functional groups 1 and 2 may be identical or different. Preferably, a backbone moiety has at least two arms, and preferably at least 4 arms.

The reactive polymers of the present invention may be homo- or copolymerized polyethylene glycols, polypropylene glycols, poly (N-vinyl pyrrolidone), poly methacrylates, polyphosphazenes, polylactides, polyacrylamides, polyglycolates, polyethylene imines, agarose, dextran, gelatin, collagen, polylysine, chitosans, alginates, hyaluronans, pectin, carrageenan or polyamino acids, which have suitable reactive functional groups and crosslinking functional groups in native state, or can be derivatized to have suitable reactive functional groups and crosslinking functional groups. Suitable reactive functional groups and crosslinking functional groups include, but are not limited to: amines, alcohols, thiols, carboxylic acids, maleimides, acrylates, acrylamides, azides, alkynes (including cyclic alkynes), 1,3-dienes (including cyclopentadiene and furans), α-halocarbonyls, N-hydroxy succinimide, N-hydroxy sulfosuccinimide esters or carbonates.

The hydrogels of the present invention may further comprise reactive functional groups not consumed in gelation process. These functional groups do not participate in the gelation process due to excess or orthogonal reactivity. These functional groups can be used to further modify hydrogels, for example, by covalently linking biologically active substances.

There are three methods to prepared drug delivery hydrogels. In some embodiments, reactive functional groups on a backbone moiety react with reactive functional group-optionally biodegradable linker—biologically active substance to give an intermediate drug-loaded polymer. Then the crosslinking functional groups on the backbone moiety react with crosslinking moieties to generate biodegradable drug delivery hydrogel. In some embodiments, crosslinking functional groups on a backbone moiety react with crosslinking moieties first to give a hydrogel, followed by reaction of reactive functional groups on the backbone moiety with reactive functional group-optionally biodegradable linker—biologically active substance, producing drug-loaded biodegradable drug delivery hydrogel. In some embodiments, backbone moieties, crosslinking moieties, and reactive functional group-optionally biodegradable linker—biologically active substance react in a single step (one pot). If there are still unreacted functional groups contained in hydrogels after gel formation, these excess functional groups can be capped by appropriate reagents.

Microporous, mesoporous or macroporous hydrogels can be produced by selecting backbone moieties and crosslinking moieties of different structures and sizes. A microporous hydrogel refers to a hydrogel having a pore diameter of less than 1 nm. A mesoporous hydrogel has a pore diameter of 1-100 nm. A macroporous hydrogel has a pore diameter larger than 100 nm.

The hydrogels of the present invention can be prepared in vitro, and then implanted. The hydrogels may be cast into specific shapes. In some embodiments, the hydrogel is a shaped article such as a stent or a mesh.

The hydrogels of the present invention can be prepared in the form of microparticulate. Preferably, the hydrogel is microparticle beads which can be administered as subcutaneous or intramuscular injection by means of a syringe. Beads are 1-500 microns in diameter. Preferably, the microparticles, if suspended in an isotonic formulation buffer, have a diameter of 10-100 microns, preferably 20-100 microns, most preferably 30-70 microns. Preferably, the microparticles can be injected using an injection needle having an internal diameter of less than 0.6 mm, preferably an injection needle having an internal diameter of less than 0.3 mm, more preferably an injection needle having an internal diameter of less than 0.25 mm, and even more preferably an injection needle having an internal diameter of less than 0.175 mm, most preferably an injection needle having an internal diameter smaller than 0.16 mm.

Alternatively, the hydrogels may be formed by in situ gelation. Pharmaceutically acceptable formulations of the hydrogel components are prepared first, and mixing of the components is followed by injection or application prior to gelation. Injection may be subcutaneous, intramuscular, intraocular, intratumoral or intravenous. The hydrogels of the present invention may be topically applied, for example by in situ gelation of the mixed components after application to the skin or surgical wounds. The hydrogels of the present invention have other applications such as regenerative medicine, implants for orthopedics or orthopedics, coatings for medical devices or surgical dressings.

The present invention is further illustrated, but are not limited to the following examples.

EXAMPLES

Protecting Groups:
Bom, benzyloxymethyl; Br—Z, 2-bromobenzyloxycarbonyl; tBu, t-butyl; Bz, benzoyl; Bzl, benzyl; Boc, tert-butyloxycarbonyl; CHO, formyl; cHx, cyclohexyl; Cbz or Z, benzyloxycarbonyl; Cl—Z, 2-chlorobenzyloxycarbonyl; Fm, 9-fluorenylmethyl; Fmoc, 9-fluorenylmethoxycarbonyl; Mtt, 4-methyltrityl; Pmc, (2,2,5,7,8-pentametylchroman-6-sulphonyl; Tos, 4-toluenesulphonyl; Trt, tripheylmethyl.

Reagents and Solvents
ACN, acetonitrile; BOP, benzotriazol-1-yloxytris(dimethylamino) phosphonium hexafluorophosphate; DCC, N,N'-Dicyclohexylcarbodiimide; DCM, dicholoromethane; DEPBT, 3-(Diethoxyphosphoryloxy)-1,2,3-benzotriazin-4(3H)-one; DIC, N,N'-Diisopropylcarbodiimide; DIPEA (or DIEA), diisopropylethylamine; DMAP, 4-N,N-dimethyl amino pyridine DMF, Dimethylformamide; DMSO, Dimethyl sulfoxide; EDC or EDCl, 1-ethyl-3-(3-dimethylaminopropyl)carbodiimide; EtOAc, Ethyl acetate; HBTU O-(1H-benzotriazole-1-yl)-N,N,N',N'-tetramethyluronium hexafluorophosphate; HOBT 1-hydroxybenzotriazole; Cl-HOBT, 6-Chloro-1-hydroxybenzotriazole; MTBE, methyl tert-butyl ether; NMM, N-Methylmorpholine; NMP, N-methylpyrrolidinone; Su, succinimide; TEA, triethylamine; TFA, trifluoroacetic acid; THF, tetrahydrofuran; TIS, triisopropylsilane 4-arm PEG20K and 8-arm PEG40K reagents are purchased from NOF America.

Unless otherwise specified, the reagents used in the present invention are from commercial sources or prepared by conventional methods known in the art, and the experiments and the procedures thereof can be performed by those skilled in the art according to the contents of the present invention and conventional techniques in the field.

Chemical Synthesis of Polypeptides
Linear peptides are synthesized with Boc or Fmoc solid phase method. Peptides with C-terminus acids are synthesized on Wang resin and peptides with C-terminus amide on Rind amide resin using Fmoc chemistry. Peptides with C-terminus acids are synthesized on 4-Hydroxymethyl-phenylacetamidomethyl (PAM) resin and peptides with C-terminus amide on 4-methylbenzhyryl amine (MBHA) resin using Boc chemistry. The coupling reagent and activator are DIC and HOBT. Other optional coupling reagents include EDC, BOP, HBTU, DEPBT and the like. Amino acids are 5-fold in excess. Condensation time is 1 hour. Fmoc protecting group is removed by treating the resin attached peptides with 50% piperidine/DMF. Boc protecting group is removed by TFA. Ninhydrin (2,2-Dihydroxyindane-1,3-dione) test was used to monitor the progress of coupling.

The commonly used amino acids and protecting groups in Fmoc solid phase peptide synthesis are as follows:
Fmoc-Cys(Trt)-OH, Fmoc-Asp(OtBu)-OH, Fmoc-Glu(OtBu)-OH, Fmoc-His(Trt)-OH, Fmoc-Lys(Boc)-OH, Fmoc-Asn(Trt)-OH, Fmoc-Gln(Trt)-OH, Fmoc-Arg(Pmc)-OH, Fmoc-Ser(tBu)-OH, Fmoc-Thr(tBu)-OH, Boc-Trp(Boc)-OH or Fmoc-Tyr(tBu)-OH.

Resin-bound peptides synthesized with Fmoc chemistry are cleaved from the solid support by treatment with TFA. To dry resin are added TFA/TIS/H$_2$O (95:2.5:2.5, 10-25 mL/g resin). After two hours of shaking, the resin is filtered and 8-10 volumes of ice-cold diethyl ether is added to the filtrate. The precipitated crude peptide is collected by centrifugation.

The commonly used amino acids and protecting groups in Boc solid phase peptide synthesis are as follows:
Boc-Cys(4-MeBzl)-OH, Boc-Asp(OcHx)-OH, Boc-Glu(OcHx)-OH, Boc-His(Bom)-OH, Boc-Lys(2-Cl—Z)—OH, Boc-Asn(Xan)-OH, Boc-Arg(Tos)-OH, Boc-Ser(Bzl)-OH, Boc-Thr(Bzl)-OH, Boc-Trp(CHO)—OH and Boc-Tyr(2-Br—Z)—OH.

After completion of synthesis with Boc chemistry peptides on PAM and MBHA resins are cleaved from the resin by HF. 5 mL of HF is added per 0.1 mmole of resin in addition to p-cresol or anisole. The mixture is stirred in ice batch for 1 hour. After HF removal in vacuo, peptides are precipitated by ice cold ether and crude peptides are collected by centrifugation.

Example 1

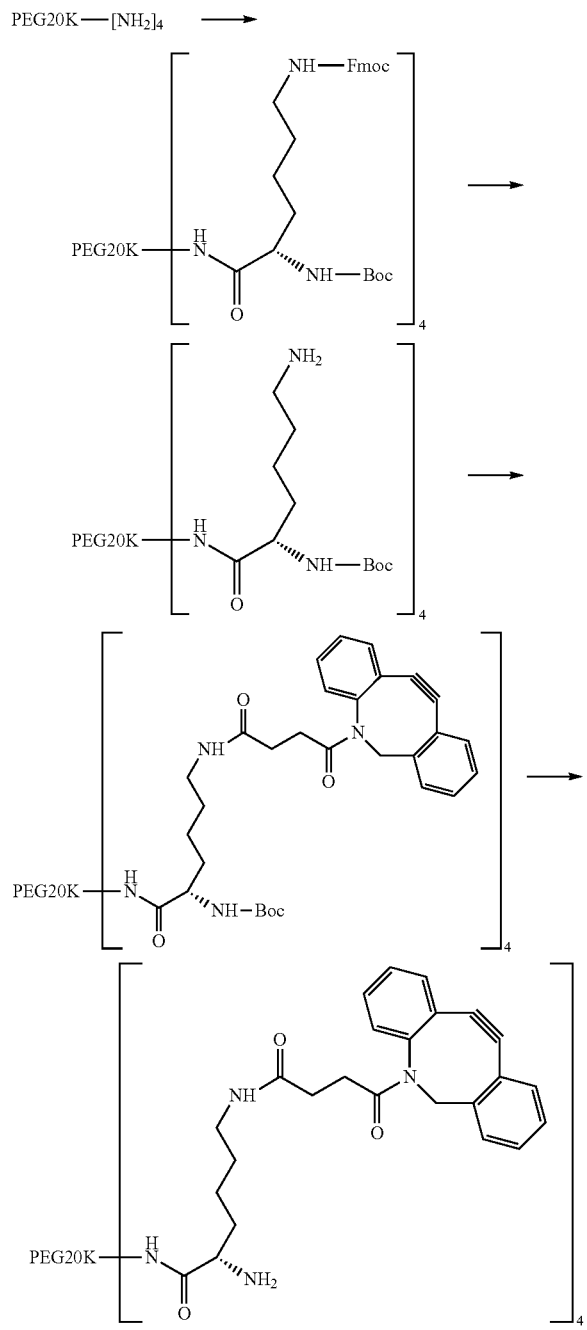

Boc-Lys(Fmoc)-OH (187 mg, 400 µmole), DEPBT (120 mg, 400 µmole), DIPEA (140 µL, 800 µmole) were added to PEG20K—(NH$_2$)$_4$ (2 g, 1001 µmole) in dichloromethane (30 mL), and the reaction was stirred at room temperature for 4 hours. Acetic anhydride (50 µL, 526 µmole) was added to the reaction, and stirring continued for 15 minutes. The reaction solution was concentrated to 10 mL. MTBE (100 mL) was added and stirred for 15 minutes. The solid precipitate was filtered and dried in vacuo. The reaction product of two batches were combined and used directly in the next reaction.

[Boc-Lys(Fmoc)-NH]$_4$-PEG20K (4.14 g, 190 µmole) was dissolved in DMF (25 mL), and piperidine (2 mL, 20 mmol) was added. The reaction was stirred at room temperature for 20 min. MTBE (150 mL) was added, and [Boc-Lys-NH]$_4$-PEG20K was obtained after filtration (3.14 g, 79%).

DBCO—OSu (81.2 mg, 200 µmole) and DIPEA (69 µL, 400 µmole) were added to [Boc-Lys-NH]$_4$-PEG20K (837 mg, 40 µmole) in acetonitrile (8 mL). The reaction was stirred at room temperature for 2 hours and then acetic anhydride (20 µL, 210.4 µmole) was added. Stirring continued for 20 minutes. The solvent was removed under reduced pressure, and the resulting solid was purified by HPLC to give [Boc-Lys(DBCO)—NH]$_4$-PEG20K (776 mg).

[Boc-Lys(DBCO)—NH]$_4$-PEG20K (776 mg) was dissolved in CH$_2$Cl$_2$ (2 ml), and TFA (1.5 ml) was added. The reaction was stirred at room temperature for 10 min. Diethyl ether (50 mL) was added. The precipitate was filtered and dried under vacuum to give a white powder [H-Lys(DBCO)—NH]$_4$-PEG20K (653 mg).

Example 2

PEG40K(NH$_2$)$_8$ (2 g, 50 µmole) was dissolved in acetonitrile (50 mL), and Fmoc-OSu (67.5 mg, 200 µmole) and DIEA (35 µl, 200 µmole) were added. The reaction was stirred overnight at room temperature. Acetonitrile was evaporated under reduced pressure to 10 mL. Two batches of reaction products were combined and added to an aqueous solution containing 0.1% TFA, and purified by preparative HPLC, A solution: 0.1% TFA B solution: 0.1% TFA, 100% acetonitrile, to give PEG40K(NH-Fmoc)$_4$(NH$_2$)$_4$ (0.83 g). The other incorrect products may be reused in another round of reaction after Fmoc removal.

PEG40K(NH-Fmoc)$_4$(NH$_2$)$_4$ (0.8 g) was dissolved in acetonitrile (5 ml), DBCO—OSu (36.2 mg) and DIEA (35 µL) were added. The reaction was stirred at room temperature for 3 hours and was then purified by dialysis (Slide-A-lyzer Dialysis Cassette, 20K MWCO, Thermo Fisher Scientific), to give PEG40K(NH-Fmoc)$_4$(DBCO)$_4$ (0.71 g).

PEG40K(NH-Fmoc)$_4$(DBCO)$_4$ (0.71 g) was dissolved in DMF (6 ml), and piperidine (173 µl) was added. The reaction was stirred at room temperature for 15 minutes. MTBE was added dropwise to the reaction. The precipitate was filtered, washed 3 times with MTBE, and dried in vacuo to give a white solid PEG40K(NH$_2$)$_4$(DBCO)$_4$ (0.6 g).

Iodoacetic acid (11.2 mg, 60 µmole), DEPBT (18 mg, 60 µmole) and DIEA (10.4 µL, 60 µmole) were added to PEG40K(NH$_2$)$_4$(DBCO)$_4$ (0.6 g) in dichloromethane (3 mL). The reaction was stirred at room temperature for 8 hours. MTBE was added dropwise to the reaction. The precipitate was filtered, washed 3 times with MTBE, and dried in vacuo to give a white solid PEG40K(NHC(O)CH$_2$I)$_4$(DBCO)$_4$ (0.6 g).

Example 3

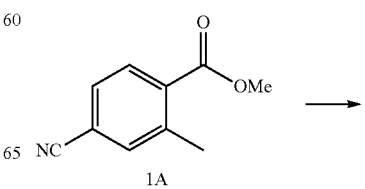

1A

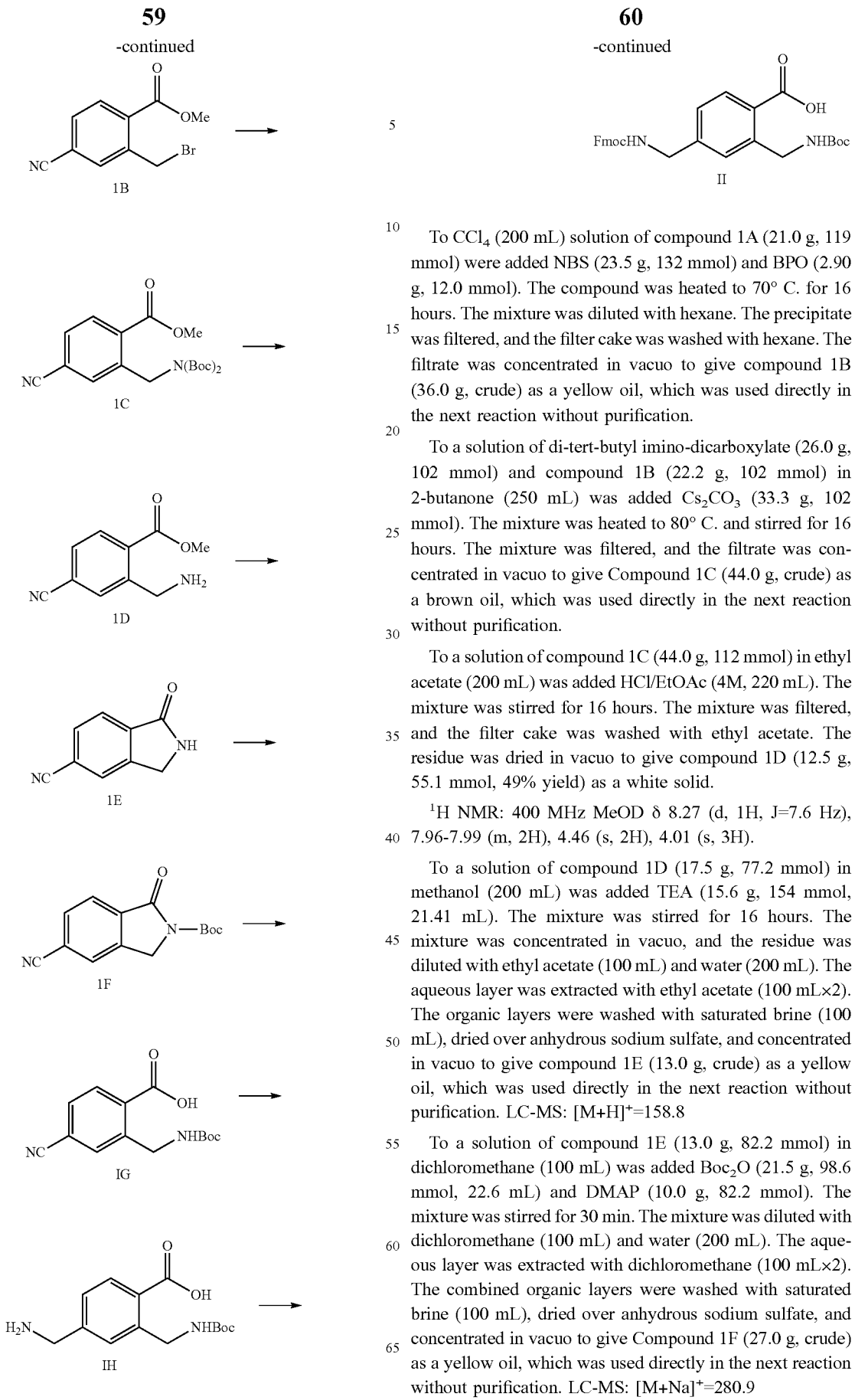

To CCl$_4$ (200 mL) solution of compound 1A (21.0 g, 119 mmol) were added NBS (23.5 g, 132 mmol) and BPO (2.90 g, 12.0 mmol). The compound was heated to 70° C. for 16 hours. The mixture was diluted with hexane. The precipitate was filtered, and the filter cake was washed with hexane. The filtrate was concentrated in vacuo to give compound 1B (36.0 g, crude) as a yellow oil, which was used directly in the next reaction without purification.

To a solution of di-tert-butyl imino-dicarboxylate (26.0 g, 102 mmol) and compound 1B (22.2 g, 102 mmol) in 2-butanone (250 mL) was added Cs$_2$CO$_3$ (33.3 g, 102 mmol). The mixture was heated to 80° C. and stirred for 16 hours. The mixture was filtered, and the filtrate was concentrated in vacuo to give Compound 1C (44.0 g, crude) as a brown oil, which was used directly in the next reaction without purification.

To a solution of compound 1C (44.0 g, 112 mmol) in ethyl acetate (200 mL) was added HCl/EtOAc (4M, 220 mL). The mixture was stirred for 16 hours. The mixture was filtered, and the filter cake was washed with ethyl acetate. The residue was dried in vacuo to give compound 1D (12.5 g, 55.1 mmol, 49% yield) as a white solid.

$^1$H NMR: 400 MHz MeOD δ 8.27 (d, 1H, J=7.6 Hz), 7.96-7.99 (m, 2H), 4.46 (s, 2H), 4.01 (s, 3H).

To a solution of compound 1D (17.5 g, 77.2 mmol) in methanol (200 mL) was added TEA (15.6 g, 154 mmol, 21.41 mL). The mixture was stirred for 16 hours. The mixture was concentrated in vacuo, and the residue was diluted with ethyl acetate (100 mL) and water (200 mL). The aqueous layer was extracted with ethyl acetate (100 mL×2). The organic layers were washed with saturated brine (100 mL), dried over anhydrous sodium sulfate, and concentrated in vacuo to give compound 1E (13.0 g, crude) as a yellow oil, which was used directly in the next reaction without purification. LC-MS: [M+H]$^+$=158.8

To a solution of compound 1E (13.0 g, 82.2 mmol) in dichloromethane (100 mL) was added Boc$_2$O (21.5 g, 98.6 mmol, 22.6 mL) and DMAP (10.0 g, 82.2 mmol). The mixture was stirred for 30 min. The mixture was diluted with dichloromethane (100 mL) and water (200 mL). The aqueous layer was extracted with dichloromethane (100 mL×2). The combined organic layers were washed with saturated brine (100 mL), dried over anhydrous sodium sulfate, and concentrated in vacuo to give Compound 1F (27.0 g, crude) as a yellow oil, which was used directly in the next reaction without purification. LC-MS: [M+Na]$^+$=280.9

To a solution of compound 1F (27.0 g, 104 mmol) in THF (200 mL) and water (200 mL) was added sodium hydroxide (12.5 g, 313 mmol). The reaction was stirred for 1 hour. Water (200 mL) was added to the mixture. The aqueous layer was acidified with 10% citric acid (300 mL) to pH 2~3, and extracted with ethyl acetate (200 mL×2). The combined organic layer was washed with saturated brine (200 mL), dried over anhydrous sodium sulfate, and concentrated in vacuo to give compound 1G (12.0 g, 43.4 mmol, 41% yield) as a white solid.

$^1$H NMR: 400 MHz CDCl$_3$ δ 8.27 (d, 1H, J=7.6 Hz), 8.07 (t, 1H, J=6.8 Hz), 7.66-7.70 (m, 2H), 4.59 (d, 1H, J=6.8 Hz), 1.48 (s, 9H).

To a solution of compound 1G (12.0 g, 43.4 mmol) in ammonia-containing methanol (150 mL) was added Raney-Ni (12.0 g, 140 mmol). The mixture was stirred in hydrogen atmosphere at 50 Psi for 16 hours. The mixture was filtered through celite, and the filter cake was washed with methanol (200 mL). The filtrate was concentrated in vacuo to give compound 1H (8.00 g, crude) as a white solid, which was used directly in the next reaction without purification. LC-MS: [M−99]$^+$=180.9

To a solution of compound 1H (8.00 g, 28.5 mmol) in dioxane (50 mL) and water (50 mL) was added sodium hydrogen carbonate (7.19 g, 85.6 mmol, 3.33 mL). After stirring for 10 min Fmoc-Cl (7.38 g, 28.5 mmol) was added. The mixture was stirred for 16 hours. The mixture was diluted with ethyl acetate (100 mL) and water (100 mL). The aqueous layer was extracted with ethyl acetate (100 mL×2). The combined organic layer was washed with saturated brine (100 mL) wash, dried over anhydrous sodium sulfate, concentrated in vacuo. The residue was purified by silica gel column. The eluate was concentrated in vacuo to give the title compound 11 (2.00 g, 3.98 mmol, 14% yield) as a white solid. LC-MS: [M−99]$^+$=403.0

$^1$H NMR: 400 MHz DMSO-d$_6$ δ12.9 (s, 1H), 7.86-7.89 (m, 3H), 7.80-7.84 (m, 1H), 7.66-7.68 (m, 2H), 7.37-7.39 (m, 2H), 7.30-7.32 (m, 3H), 7.13-7.25 (m, 2H), 4.43 (d, 2H, J=6.4 Hz), 4.30 (d, 2H, J=7.2 Hz), 4.18-4.21 (m, 3H), 1.35 (s, 9H).

Example 4

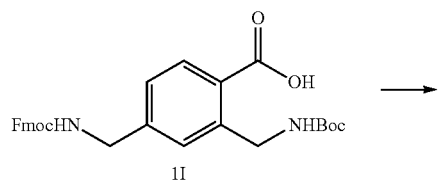

11

Compound 11 (1 g, 2 mmole), DEPBT (598 mg, 2 mmole), DIPEA (348 µL, 2 mmole) were added sequentially to PEG20K—(NH$_2$)$_4$ (10 g, 500 µmole) in dichloromethane (30 mL). The reaction was stirred at room temperature for 4 hours. Acetic anhydride (50 µL, 526 µmole) was added to the reaction, and stirring continued for 15 minutes. The reaction solution was concentrated to 10 mL. MTBE (100 mL) was added and stirred for 15 minutes. The solid precipitate was filtered and dried in vacuo. Intermediate product (10.5 g, 477 µmole) was dissolved in DMF (50 mL), and piperidine (10 ml, 100 mmol) was added. The reaction was stirred at room temperature for 20 min, and MTBE (500 mL) was added. Product 2B was obtained after filtration, which was used directly in the next reaction.

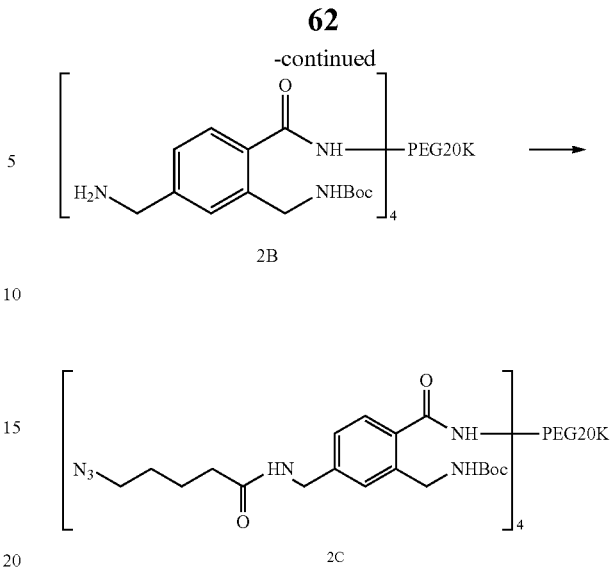

To a solution of compound 2B (9 g, 429 µmole) in dichloromethane (40 mL) were added 5-azido pentanoic acid (64 mg, 56.5 µL, 450 µmole), DEPBT (135 mg, 450 µmole), and DIEA (58 mg, 78 µL, 450 µmole). The reaction was stirred for 12 hours at room temperature. The reaction solution was concentrated to 15 mL. MTBE (100 ml) was added and stirred for 15 minutes. The solid precipitate was filtered and purified by Sephadex G-50, and dried in vacuo to give a white powder 2C (8.2 g).

Example 5

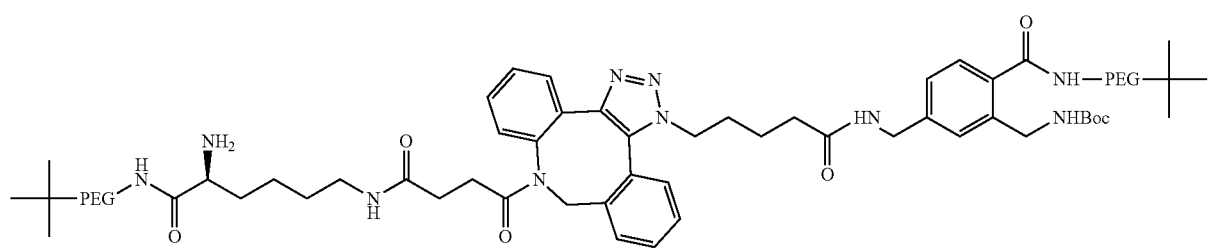

3A

[H-Lys(DBCO)—NH]₄-PEG20K (50 mg) and 2C (50 mg) were first dissolved in PBS (2 mL), and stood for 5 hours after mixing to obtain a hydrogel containing free amino groups. The backbone moieties and crosslinking moieties are connected as shown in 3A. The hydrogel was washed successively with purified water (2 mL), ethanol (2 mL) and acetonitrile (2 mL), and dried in vacuo. The free amino groups of the hydrogel can continue to be derivatized into other orthogonal reaction functional groups for different purposes, such as loading biologically active substances. Boc protecting group on the biodegradable linkers may be cleaved by TFA in a subsequent synthesis step. Gelation time is defined as the conversion of the solution from liquid to gel and can no longer be extracted with a pipette. Gelation time of 3A is 2 minutes.

Example 6

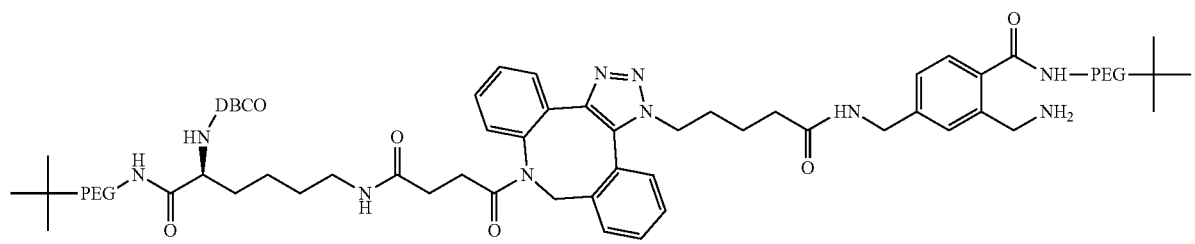

3B

The hydrogel (50 mg) obtained in Example 5 was suspended in acetonitrile (200 μL), and DBCO—OSu (4 mg, 10 μmol) and DIEA (2 μL, 11.5 μmol) were added. After 12 hours, the supernatant was removed. The hydrogel was washed with acetonitrile (2×1 mL), re-suspended in acetonitrile (200 μL), and DIEA (4 μL, 23 μmol) and acetic anhydride (2.2 μL, 23 μmol) were added. The supernatant was removed after 1 hour and the hydrogel was dried. 50% TFA/CH₂Cl₂ (200 μL) was added to the hydrogel and was removed after 15 minutes. The hydrogel was washed with acetonitrile (2×1 mL), and dried in vacuo. The DBCO substituted hydrogel backbone moieties and the crosslink moieties are connected as shown in FIG. 3B, and are able to react with N₃— biodegradable linker—biologically active substances and becomes a drug delivery hydrogel.

Example 7

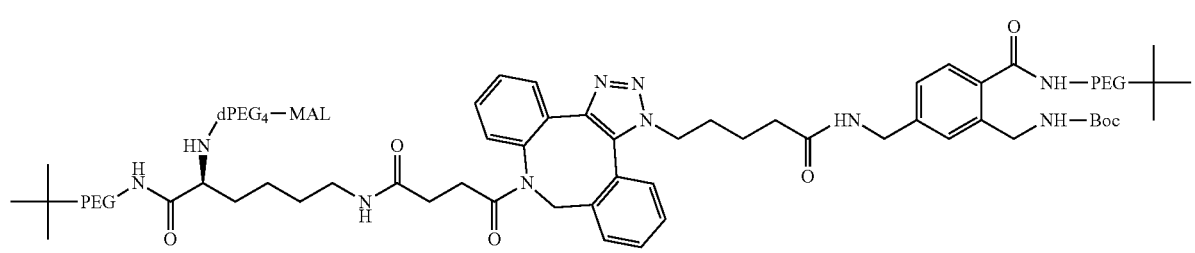

3C

The hydrogel (50 mg) obtained in Example 5 was suspended in DMF (500p), and MAL-dPEG₄-NHS (Quanta Biodesign, 5.3 mg, 20 μmol) and DIEA (4 μL, 23 μmol) were added. After 30 minutes, the supernatant was removed. The hydrogel was washed successively with purified water (1 mL), ethanol (1 mL) and acetonitrile (1 mL), and dried in vacuo to give a hydrogel, in which the backbone moieties and the crosslink moieties are connected as shown in 3C.

Example 8

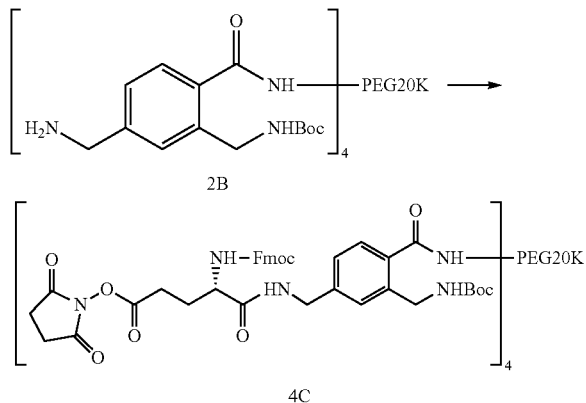

To 2B (2 g) in DMF (40 ml) were added Fmoc-L-glutamic acid-γ-2-phenylisopropyl ester (CAS 200616-39-3) (53.6 mg, 110 μmole), DEPBT (33 mg, 110 μmole) and DIEA (19 μL, 110 μmole). The reaction was stirred at room temperature overnight. The solvent was evaporated under reduced pressure. The solid residue was dissolved in 1% TFA/CH$_2$Cl$_2$ (10 ml), and stirred at room temperature for 10 minutes. The solvent was evaporated under reduced pressure, and the residue was purified by HPLC, to give [Fmoc-Glu-NH]$_4$-2B (1.87 g).

[Fmoc-Glu-NH]$_4$-2B (1 g) was dissolved in DMF (15 mL), and N, N'-dicyclohexyl carbodiimide (41.7 mg, 200 μmole) and N-hydroxysuccinimide (23.4 mg, 200 μmole) were added. The reaction was stirred at room temperature overnight, and the precipitate was filtered. The solvent was evaporated under reduced pressure to give a white solid 4C (0.7 g).

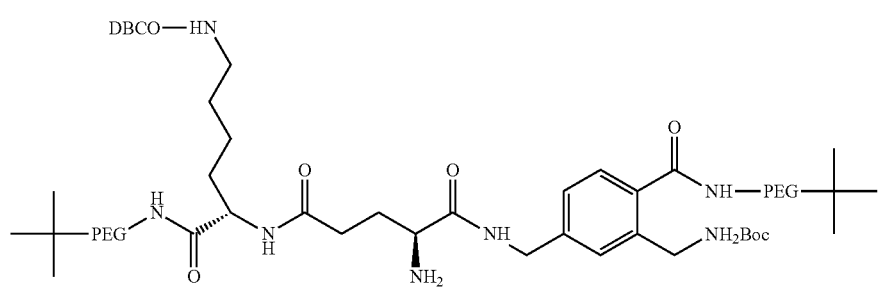

[H-Lys(DBCO)—NH]$_4$-PEG20K (0.5 g) and 4C (0.5 g) were dissolved in DMSO (2 mL), and Arlacel P135 (20 mg) in heptane (20 mL) was added. The mixture was stirred rapidly and N, N, N',N'-tetramethyl-ethylenediamine (0.2 mL) was added dropwise. Stirring continued at room temperature for 15 hours. Acetic acid (0.5 mL) and water (15 mL) were added. The aqueous phase was separated after stirring for 5 minutes. The water—hydrogel suspension was wet sieved on steel sieves of #200, #300, #360 and #500 mesh. Fractions were collected, washed successively with water, ethanol and acetonitrile, and then suspended in DMF (5 mL). Piperidine (1 mL) was added, and the supernatant was discarded after 15 minutes. The hydrogel was washed with dichloromethane, water and ethanol, and dried in vacuo to give white powdery hydrogel beads, in which the backbone moieties and crosslinking moieties are connected as shown in 4D, and in which free amino groups can continue to be derived into other orthogonal reactive functional groups. This hydrogel comprise two different reactive functional groups which can be used for different purposes, such as loading of two different biologically active substances. Boc protecting groups on the biodegradable linkers can be cleaved with TFA in a subsequent synthesis step. Compared to 3C, adding reaction functional groups to the crosslinking moieties can enhance drug loading.

Example 9

Synthesis of 4-((3-(((9H-fluoren-9-yl)methoxy)carbonyl)amino)propyl)carbamoyl)-2-(((tert-butoxycarbonyl)amino)methyl)benzoic acid

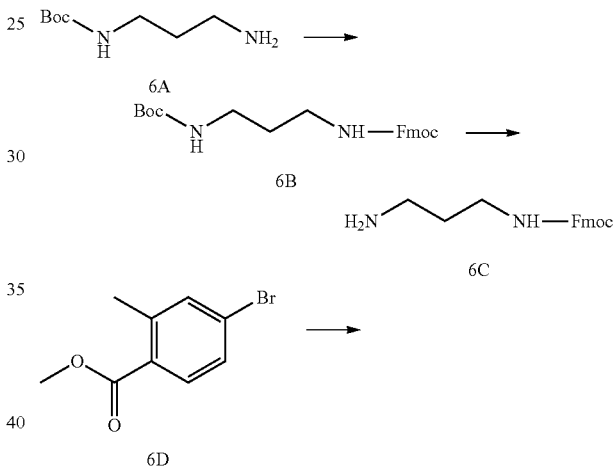

-continued

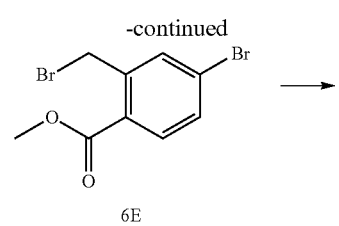

-continued

6F — 5-bromoisoindolin-1-one

6G — methyl 1-oxoisoindoline-5-carboxylate

6H — methyl 2-Boc-1-oxoisoindoline-5-carboxylate

6I — 2-((Boc-amino)methyl)-4-(hydroxycarbonyl)benzoic acid

6J — BocHN-CH2-[aryl]-C(O)NH-(CH2)3-NH-Fmoc

To a solution of 6A (10 g, 57.4 mmol) in dichloromethane (200 mL) were added saturated sodium bicarbonate (200 mL) and FmocCl (17 g, 66 mmol). The mixture was stirred overnight.

The mixture was separated. The organic layer was washed with water, brine, dried over anhydrous sodium sulfate, and concentrated in vacuo. The residue was purified by flash column chromatography to give 6B (15 g, 66%).

To a solution of 6B (15 g, 38 mmol) in dichloromethane (200 mL) was added TFA (100 mL). The mixture was stirred at room temperature for 3 hours. The mixture was concentrated in vacuo. The residue was poured into ice water (200 mL), basified with sodium bicarbonate solution to pH>8. The mixture was filtered, and the filter cake was washed with water, and dried in vacuo to give 6C (11 g, 98%) as a white solid.

To a solution of 6D (50 g, 0.22 mol) in CCl$_4$ (750 mL) were added N-bromosuccinimide (38.9 g, 0.22 mol) and benzoyl peroxide (1.1 g, 4.4 mmol). The reaction mixture was stirred for 4 hours at 60° C. under a 250W lamp. The mixture was cooled to room temperature, washed with 1M aqueous solution of sodium hydroxide and water, and dried over anhydrous sodium sulfate. The solvent was evaporated to give the crude product 6E (75 g) as an oil, which was used directly in the next reaction.

Crude 6E (75 g) was suspended in NH$_3$/MeOH (2M, 750 mL) and concentrated ammonium hydroxide (250 mL) and was stirred overnight. The mixture was filtered, and the filter cake was dried in vacuo to give 6F (35 g, 75% yield in two steps) as a white solid.

$^1$H-NMR (400 MHz, DMSO_d$_6$): 8.64-8.66 (s, 1H), 7.83 (s, 1H), 7.66-7.68 (d, 1H), 7.59-7.61 (s, 1H), 4.37 (s, 2H)

To a solution of 6F (6 g, 28 mmol) in methanol (100 mL) were added palladium acetate (0.12 g), Et$_3$N (8.6 g, 85 mmol) and xantphos (0.6 g). The reaction mixture was stirred overnight at 140° C. in CO (3 MPa) environment. The mixture was cooled to room temperature and filtered. The filtrate was concentrated in vacuo to give 6G (6 g).

$^1$H-NMR (400 MHz, DMSO_d$_6$): 8.82-8.84 (s, 1H), 8.16-8.18 (s, 1H), 8.05-8.07 (s, 1H), 7.79-7.81 (s, 1H), 4.44-4.46 (s, 2H), 3.90-3.92 (s, 3H)

To a solution of 6G (6 g) in CH$_2$Cl$_2$ (180 mL) were added di-tert-butyl dicarbonate (12.2 g, 56 mmol), Et$_3$N (2.8 g, 28 mmol) and DMAP (3.4 g, 28 mmol). The reaction mixture was stirred at room temperature for 2 hours. The mixture was washed with 0.5N HCl and water, dried over anhydrous sodium sulfate, and concentrated in vacuo. The crude product was purified by flash column chromatography to give 6H (4.2 g, 51% yield in two steps) as a white solid.

$^1$H-NMR (400 MHz, CDCl$_3$): 8.15-8.17 (m, 2H), 7.96-7.98 (m, 1H), 4.80-4.82 (s, 2H), 3.96-3.98 (s, 3H), 1.59-1.61 (s, 9H)

To a solution of 6H (5.8 g, 20 mmol) in THF (100 mL) was added an aqueous solution (100 mL) of LiOH.H$_2$O (4.2 g, 100 mmol). The reaction mixture was stirred at room temperature for 5 hours. The reaction mixture was concentrated in vacuo. Aqueous layer was acidified with citric acid to PH<6, and then filtered. The filter cake was dried in vacuo to give 6I (4.6 g, 78%) as a white solid.

$^1$H-NMR (400 MHz, DMSO_d$_6$): 7.86-7.98 (m, 3H), 7.38-7.40 (m, 1H), 4.48-4.49 (m, 2H), 1.40-1.42 (s, 9H)

To a solution of 6I (3 g, 10.1 mmol) and 6C (3 g, 10.1 mmol) in DMF (30 mL) were added EDCl (1.9 g, 10.1 mmol), HOBt (1.3 g, 10.1 mmol) and NMM (1.11 mL, 10.1 mmol). The mixture was stirred at room temperature for 2 hours. Three batches were combined, poured into water and extracted with ethyl acetate. The combined organic layers were washed with brine, dried over anhydrous sodium sulfate, filtered, and concentrated in vacuo. The residue was purified by flash column chromatography (1.7 g). The crude product was recrystallized to give pure 6J (1.1 g, 6.3%) as a white solid.

$^1$H-NMR (400 MHz, DMSO_d$_6$): 13.21 (br, 1H), 8.55-8.53 (m, 1H), 7.89-7.87 (m, 4H), 7.76-7.67 (m, 3H), 7.43-7.23 (m, 6H), 4.50-4.20 (m, 5H), 3.32-3.24 (m, 2H), 3.07-3.02 (m, 2H), 1.70-1.65 (m, 2H), 1.40-1.27 (m, 9H). LC-MS: m/z=473.9 (M-100+1).

Example 10

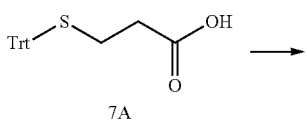

7A

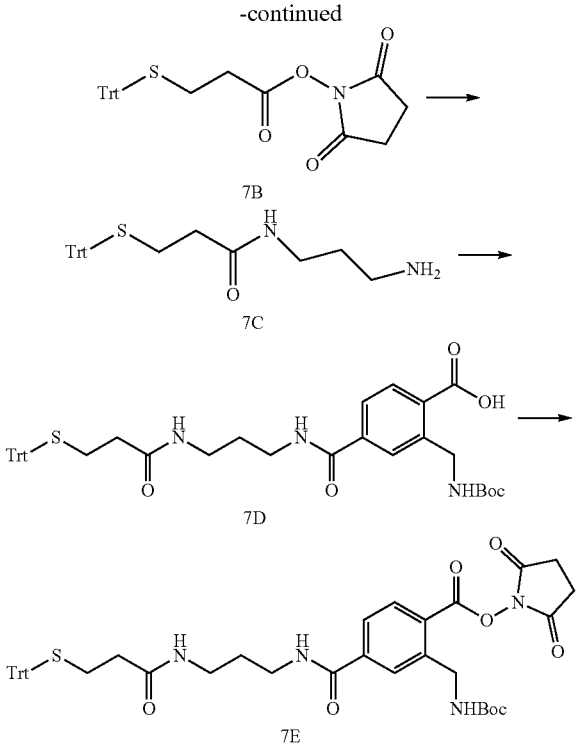

To a solution of 7A (5.0 g, 14.3 mmol) in dichloromethane (100 mL) were added triethylamine (2.9 g, 28.7 mmol, 3.98 mL), HATU (6.55 g, 17.2 mmol) and N-hydroxysuccinimide (1.98 g, 17.2 mmol). The reaction was stirred for 2 hours to obtain 7B, which was used directly in the next reaction without purification.

To a solution of 7B (1.28 g, 2.87 mmol) in dichloromethane (20 mL) was added 1,3-propanediamine (5.00 g, 28.7 mmol) in dichloromethane (40 mL). The reaction was stirred at room temperature for 12 hours. The solvent was evaporated under reduced pressure, and the residue was purified by silica gel column chromatography to give 7C (500 mg, 43% yield) as a yellow solid.

$^1$H NMR: 400 MHz CDCl$_3$,δ 7.41-7.39 (m, 6H), 7.28-7.26 (m, 6H), 7.24-7.17 (m, 3H), 6.30 (br, s, 1H), 3.25 (q, J=6.0 Hz 2H), 2.75 (t, J=6.0 Hz, 2H), 2.49-2.38 (m, 5H), 2.05 (t, J=6.8 Hz, 2H), 1.62-1.59 (m, 2H). LCMS: (M+23)+: 427.2.

To a solution of 6l (729 mg, 2.47 mmol) in dichloromethane (20 mL) were added triethylamine (1.00 g, 9.88 mmol, 1.37 mL), HATU (939 mg, 2.47 mmol) and 7C (1.00 g, 2.47 mmol). The reaction was stirred for 12 hours and then diluted with dichloromethane (20 mL) and water (20 ml). The aqueous layer was extracted with dichloromethane. The combined organic layers were washed with saturated brine (20 mL), dried over anhydrous sodium sulfate, and concentrated under reduced pressure to give a residue, which was purified by preparative HPLC to give 7D (1.00 g, 59% yield) as a white solid.

$^1$H NMR: 400 MHz CDCl$_3$ δ 7.43-7.41 (m, 6H), 7.29-7.20 (m, 7H), 4.57 (d, J=2.0 Hz, 2H), 3.45 (s, 2H), 3.31 (s, 2H), 3.13 (d, J=7.6 Hz, 1H), 2.52 (t, J=6.0 Hz, 2H), 2.09 (t, J=6.8 Hz, 2H), 1.69 (s, 2H), 1.40 (s, 9H). LCMS: (M+23)+: 704.2

To a solution of 7D (1.50 g, 2.20 mmol) in THF (20 mL) was added DCC (590 mg, 2.86 mmol) and N-hydroxysuccinimide (329 mg, 2.86 mmol). The reaction was stirred for 12 hours. The reaction mixture was filtered and concentrated under reduced pressure to give a residue, which was purified by silica gel column chromatography to give 7E (0.87 g) as a white solid.

$^1$H NMR: 400 MHz CDCl$_3$ δ 8.16 (t, J=6.4 Hz, 1H), 8.00 (s, 1H), 7.87 (d, J=8.0 Hz, 1H), 7.42-7.40 (m, 6H), 7.28-7.17 (m, 9H), 6.02 (br, s, 1H), 5.68 (br, s, 1H), 4.56 (d, J=6.0 Hz, 2H), 3.44 (d, J=12 Hz, 3H), 3.27 (d, J=5.6 Hz, 2H), 2.91 (s, 4H), 2.56-2.47 (m, 2H), 2.13-2.07 (m, 2H), 1.69 (s, 2H), 1.40 (s, 9H)

Example 11

Human insulin (18 mg, 3.1 μmol) and 7E (2 mg, 2.57 μmol) were dissolved in DMSO (300 L), and DIEA (1.56 μL, 9 μmol) was added. The reaction was stirred for 1 hour and then purified by RP-HPLC. To the lyophilized solid was added TFA (2 mL) and stirred for 15 minutes. 20% acetonitrile (5 mL) was added, and purification by RP-HPLC gave the following product after lyophilization

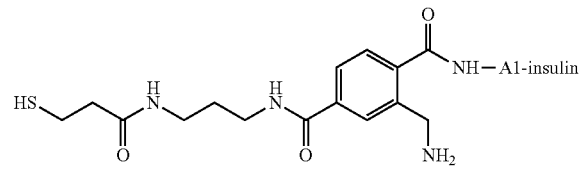

LCMS: [M+1]$^+$=6130.2

Example 12

The following exenatide derivative can be synthesized with the above mentioned peptide synthesis methods and purified by RP-HPLC.

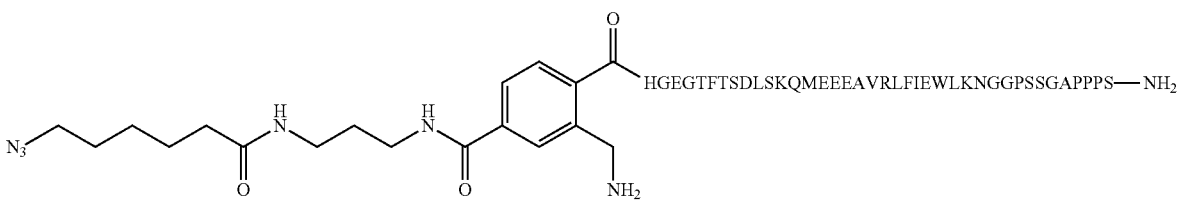

(SEQ ID NO:1)

MS: [M+1]$^+$=4559.1

This exenatide derivative may react with a hydrogel which comprises DBCO reactive groups, and is loaded on the hydrogel.

Example 13

Determination of Half Life in Pbs

Peptides GIVEQAA-NH$_2$ (SEQ ID NO: 3) and GIVEQAAY (SEQ ID NO: 2), two mimics of the N-terminus section of insulin A chain, were used as model peptides to determine the half lives of various biogradable linkers linked to the N-terminus of the peptides through an amide bond. The model peptides were prepared with Fmoc chemistry, cleaved by TFA and purified by preparative RP-HPLC.

A model peptide capped with a biodegradable linker was dissolved at 1 mg/mL concentration in PBS and the solution was incubated at 37° C. in a water bath. Samples were collected for analysis at different time points (e.g., 8 h, 16 h, 24 h, 48 h, 72 h, 96 h, 120 h). If the half life of a peptide capped with a biodegradable linker is significantly longer or shorter, the time frame for sample analysis would be changed accordingly. The cleavage of a biodegradable linker was quenched by lowering pH to 2 by addition of 0.1% TFA solution. RP-HPLC was used to monitor the cleavage reactions and the cleavage rates were quantitatively studied by measuring the peak areas of model peptides when they are capped with biodegradable linkers and when linkers are released. Agilent 6110 Quadrupole LC-MS was employed to verify the change of mass in the course of reaction.

RP-HPLC analysis was performed using a Shimadzu LC-2010A HT system and a 150 mm×4.6 mm Zorbax 300SB-C18 column. The flow rate was 1 ml/min. Solvent A contained 0.1% TFA/5% CH$_3$CN in deionized water, and solvent B contained 0.1% TFA in 100% CH$_3$CN. A linear gradient was employed (e.g., 10-70% B in 10 minutes).

The rate of cleavage was determined for the model peptides capped with respective biodegradable linkers. The concentrations of the model peptides capped with biodegradable linkers and the released model peptides were determined by their respective peak areas. The first order dissociation rate constant of a model peptide capped with a biodegradable linker was determined by plotting the logarithm of [starting model peptide capped with the biodegradable linker]/[remaining model peptide capped with the biodegradable linker] at various time intervals. The cleavage half life of a peptide capped with a biodegradable linker was calculated by using the equation and the slope derived from this plot.

The cleavage half lives of the model peptides capped with various biodegradable linkers were determined using the procedures described above. The data generated in these experiments is presented in Tables 1 and 2.

TABLE 1

Cleavage of various biodegradable linkers attached to the N terminus of model peptide X-GIVEQAAY (SEQ ID NO: 2)

| X | $t_{1/2}$ (h) |
|---|---|
| 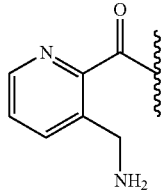 [SMILES: *C(=O)c1ncccc1CN] | 596.8 |
| 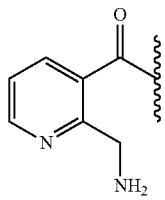 [SMILES: *C(=O)c1cccnc1CN] | 457.5 |
| 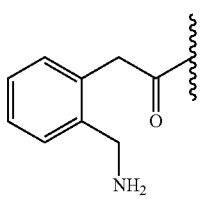 [SMILES: *C(=O)Cc1ccccc1CN] | 481.8 |
| 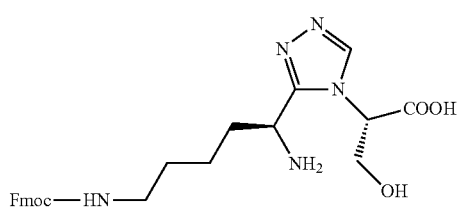 | 79.7 |

TABLE 1-continued
Cleavage of various biodegradable linkers attached to the N terminus of model peptide X-GIVEQAAY (SEQ ID NO: 2)
| X | $t_{1/2}$ (h) |
|---|---|
| 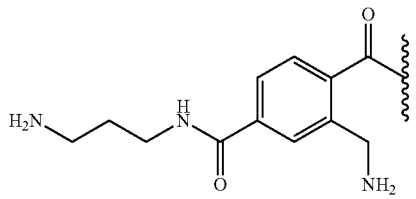 [SMILES: *C(=O)c1ccc(C(=O)NCCCN)cc1CN] | 112.1 |
| 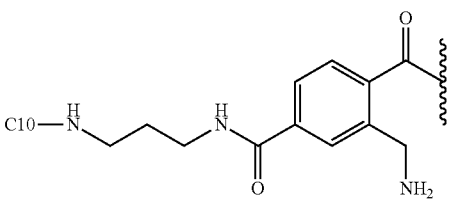 | 181.3 |
| 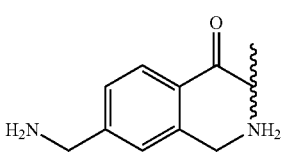 | 263.7 |
| 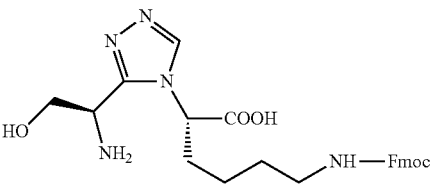 | 193.1 |
| 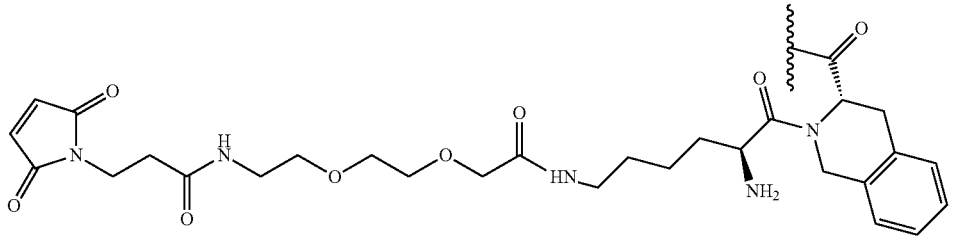 [SMILES: *C(=O)[C@@H]1Cc2ccccc2CN1C(=O)[C@@H](N)CCCCNC(=O)COCCOCCNC(=O)CCN1C(=O)C=CC1=O] | 72.6 |
| 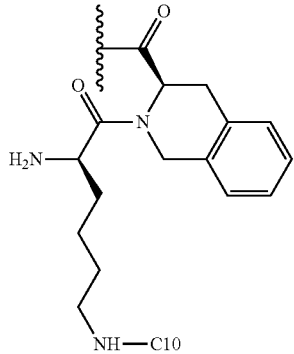 | 50.6 |

TABLE 1-continued
Cleavage of various biodegradable linkers attached to the N terminus of model peptide X-GIVEQAAY (SEQ ID NO: 2)
| X | $t_{1/2}$ (h) |
|---|---|
| 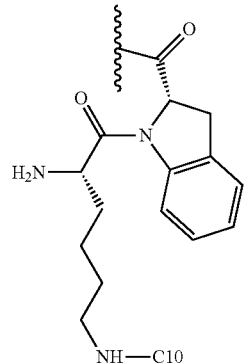 | 6.0 |
| 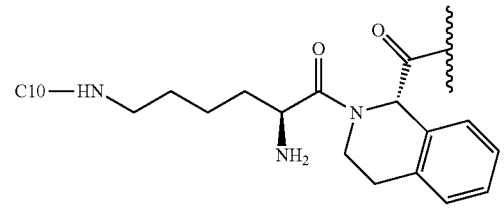 | 262.4 |
| 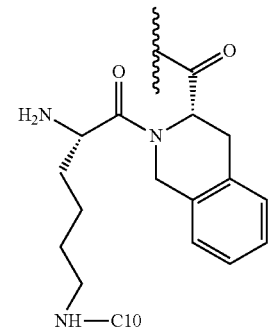 | 46.9 |
TABLE 2
Cleavage of various biodegradable linkers attached to the N terminus of model peptide X-GIVEQAA (SEQ ID NO: 3)
| X | $t_{1/2}$ (h) |
|---|---|
| 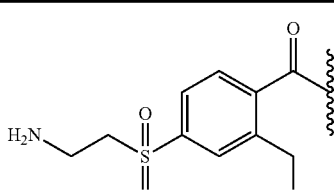 | 28.1 |
| 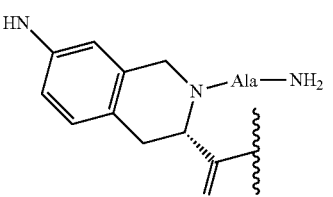 | 38.9 |

TABLE 2-continued

Cleavage of various biodegradable linkers attached to the N terminus of model peptide X-GIVEQAA (SEQ ID NO: 3)

| X | $t_{1/2}$ (h) |
|---|---|
| 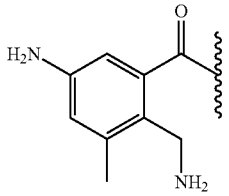 [SMILES: *C(=O)c1cc(N)cc(C)c1CN] | 85.0 |
| 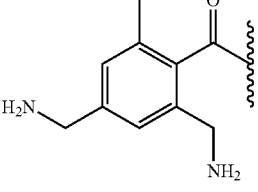 | 300.1 |

Cleavage half life of the compound below is 779 h.

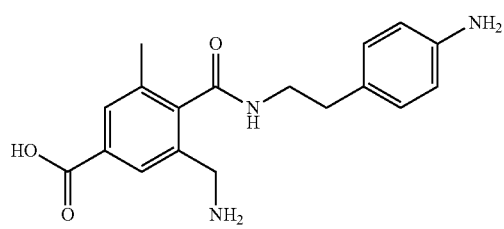 [SMILES: Cc1cc(C(=O)O)cc(CN)c1C(=O)NCCc1ccc(N)cc1]

Example 14

Determination of Half Life in Serum

Model peptides X-G-dI-dV-dE-dQ-dA-dA (SEQ ID NO:4) capped with various biodegradable linkers were used in the assay. D amino acids were used to prevent other enzymatic cleavage of the model peptides. The peptides were dissolved in 100% serum and incubated at 37° C. Samples were collected for analysis at different time points (e.g., 8 h, 16 h, 24 h, 48 h, 72 h, 96 h, and 120 h). If the half life of a model peptide capped with a biodegradable linker is significantly longer or shorter, the time frame for sample analysis would be changed accordingly.

The rate of cleavage was determined for the model peptides capped with respective biodegradable linkers. The concentrations of the model peptides capped with biodegradable linkers and the released model peptides were determined by their respective peak areas. The first order dissociation rate constant of a model peptide capped with a biodegradable linker was determined by plotting the logarithm of [starting model peptide capped with the biodegradable linker]/[remaining model peptide capped with the biodegradable linker] at various time intervals. The cleavage half life of a peptide capped with a biodegradable linker was calculated by using the equation and the slope derived from this plot.

TABLE 3

Cleavage of various biodegradable linkers attached to the N terminus of model peptide X-G-dI-dV-dE-dQ-dA-dA (SEQ ID NO: 4)

| X | $t_{1/2}$ (h) |
|---|---|
| 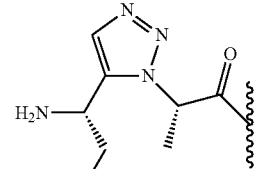 | 96.4 |
| 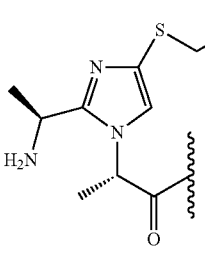 | 72.3 |
| 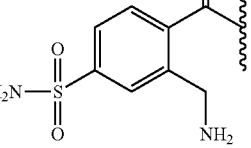 | 39.9 |
| 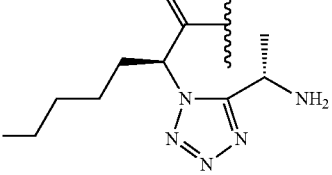 | 91.5 |
| 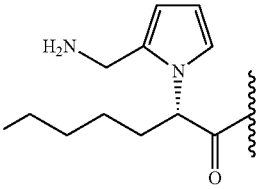 | 102.8 |
| 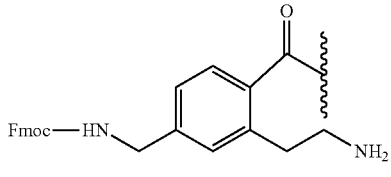 | 734.6 |

Example 15

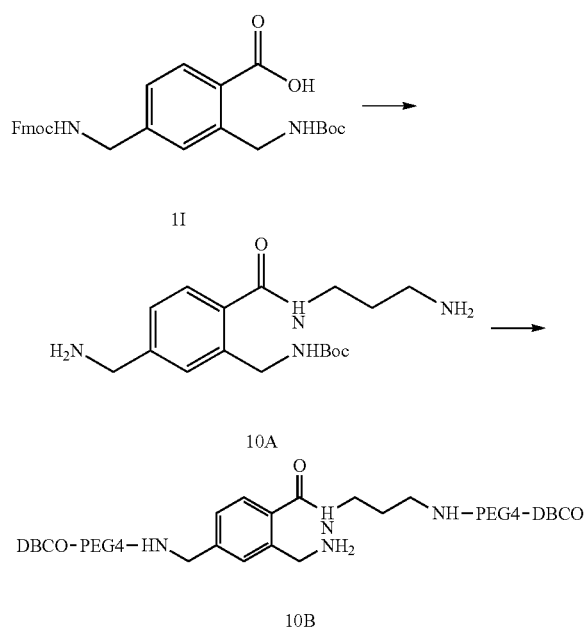

Compound 11 (100 mg, 0.2 mmole), DEPBT (60 mg, 0.2 mmole), DIPEA (35 µL, 0.2 mmole) were added sequentially to 6C (44.5 mg, 0.15 mmole) in DMSO (2 mL) and stirred at room temperature overnight. The mixture was diluted with ethyl acetate (100 mL) and water (100 mL). The aqueous layer was extracted with ethyl acetate (100 mL×2). The combined organic layer was washed with saturated brine (100 mL), dried over anhydrous sodium sulfate, and concentrated in vacuo. The residue was dissolved in 50% piperidine/DMF (3 mL), and stirred at room temperature for 15 minutes. The mixture was diluted with ethyl acetate (20 mL) and water (20 mL). The aqueous layer was extracted with ethyl acetate (15 mL×2). The combined organic layer was washed with saturated brine (10 mL), dried over anhydrous sodium sulfate, and concentrated in vacuo. The residue was purified by silica gel chromatography. The eluate was concentrated in vacuo to give 10A (61 mg, 91% yield). 10A (61 mg) and DIEA (48 mg, 65 µl) were added slowly to DBCO-PEG4-NHS (CAS: 1427004-19-0,259.6 mg, 0.4 mmole) in dichloromethane (2 mL) and was stirred at room temperature for 1 hour. The solvent was evaporated. 50% TFA/dichloromethane (2 mL) was added and stirred for 15 min. The solvent was evaporated. The residue was purified by flash chromatography to give 10B (183 mg).

Example 16

3-azido-propionic acid (202.5 mg, 1.76 mmole), DEPBT (528 mg, 1.76 mmole), and DIEA (306.6 µL, 1.76 mmole) were added to PEG5K—(NH$_2$)$_8$ (1 g, 0.2 mmole) in dichloromethane (15 mL) and stirred at room temperature for 8 hours. The reaction solution was concentrated to 5 mL. MTBE (30 mL) was added and stirred for 15 minutes, and the solid precipitate was filtered and dried in vacuo to give PEG5K—[NHC(O)—CH$_2$CH$_2$N3]$_8$ (1.03 g).

Example 17

10B (10 mg) was added to PEG5K—[NHC(O)—CH$_2$CH$_2$N3]s (10 mg) in PBS (400 µL) to give a hydrogel 17A. 10B (20 mg) was added to PEG5K—[NHC(O)—CH$_2$CH$_2$N3]s (10 mg) in PBS (400 µL) to give the hydrogel 17B. 17A and 17B were suspended in PBS respectively, incubated in a water bath at 37° C., and collected for sample analysis by HPLC at fixed time intervals using Phenomenex Bio-Sep SEC-S2000 4.6×300 mm 5 µM gel filtration column. Degradation time of 17A is 301 hours, and 17B is 487 hours, indicating, when crosslinking density increases, degradation rate of the hydrogel decreases.

Example 18

The hydrogel (5 mg) obtained in Example 7 was suspended in PBS and 8A (6 mg) was added to react at room temperature for 30 minutes. After supernatant removal and wash with PBS, insulin-containing hydrogel was obtained and dried in vacuo. 50% TFA/CH$_2$Cl$_2$ (200 µL) was added to the hydrogel and was removed after 15 minutes. The hydrogel was washed with acetonitrile (3×1 mL) and purified water.

To measure the loading of insulin in the hydrogel, the insulin containing hydrogel (1 mg) was incubated at pH10 in a water bath to completely release insulin from the hydrogel. The insulin content of the sample is calculated by comparing the area of the insulin peak in the HPLC with the area of the known precisely quantified insulin standard under the same system. The actual amount of insulin is 0.3 mg. The insulin-containing hydrogel (1 mg) was suspended in PBS (1 ml), incubated in a water bath at 37° C., and sampled once every 48 hours. The half life of insulin release in PBS was calculated according to the method in Example 13. The half-life of insulin release is 197 hours.

Example 19

The hydrogel (10 mg) obtained in Example 6 was suspended in PBS (2 ml), and 9A (5 mg) was added. After 1 hour the supernatant was removed and the product was washed with pure water to give an exenatide loaded hydrogel. The exenatide content of hydrogel and the half life of exenatide release were measured and calculated according to the method in Example 18.1 mg of hydrogel contains 0.2 mg of exenatide. The half-life of exenatide release is 143 hours.

Example 20

The hydrogel (100 mg) obtained in Example 8 was suspended in dichloromethane (500 µL), MAL-dPEG$_4$-NHS (Quanta Biodesign, 1.59 mg) and DIEA (2 µL) were added. After 30 minutes TFA (500 µL) was added. The supernatant was removed after 20 minutes and the hydrogel was washed with dichloromethane (2×1 mL), acetonitrile (2×1 mL) and PBS (2×1 mL), and then suspended in PBS (500 L). 8A (36.8 mg) was added. After reaction at room temperature for 30 minutes, the supernatant was removed. 9A (45.6 mg) in PBS solution was added. After reaction at room temperature for 30 minutes, the supernatant was removed and the product was washed with pure water (3×1 mL) to give a hydrogel loaded with insulin and exenatide.

Example 21

The lyophilized powder of recombinant urate oxidase (1 mg), 10B (20 mg) and PEG5K—[NHC(O)—CH$_2$CH$_2$N3]s (10 mg) were dissolved in PBS (400 µL), and left standing after mixing for five hours. HPLC analysis found no free urate oxidase in the supernatant, indicating urate oxidase has been encapsulated in the hydrogel. Human serum (600 µL) was added to urate oxidase hydrogel and incubated at 37° C. in a water bath. Samples were collected at different time points for HPLC analysis with a Phenomenex Bio-Sep SEC-S2000 4.6×300 mm 5 µM gel filtration column. Urate oxidase was completely released in 416 hours. Rasburicase (recombinant urate oxidase) is a short acting drug for intravenous administration. An urate oxidase hydrogel can be made into a long-acting dosage form that is injected subcutaneously by the patient himself.

Conventional protein encapsulated hydrogels usually require a crosslinking reagent with functional groups such as methacrylate at the end, and proteins are encapsulated in a redox system (eg, amine persulfate/N,N,N',N'-tetramethylethylenediamine). Such reactions and solvents may have an impact on the normal function of the protein. The cognate reactive pairs of azide and alkynyl, amino and succinimide, sulfhydryl and maleimide used in the present invention avoid this risk, and the release rates of the encapsulated proteins may be adjusted by changing biodegradable linkers, molecular weights of backbone moieties (e.g., a 8-arm PEG in this example), length of crosslinking moieties, and crosslink density. In general, the higher molecular weight of backbone moieties, the longer the length of crosslinking moieties, the larger the pore size of hydrogels, and more easily the encapsulated protein diffuses. Crosslinking density is also an effective way to adjust the pore size of hydrogels. Many protein drugs require intravenous injection, e.g. imiglucerase, RIXUBIS (recombinant coagulation factor IX), etc. Intravenous infusion time of NAGLAZYME (Galsulfase formulation) is at least 4 hours and it therefore needs to be performed at a medical facility. All of these drugs can be used to develop long-acting hydrogel formulations that patients can subcutaneously administer by using a method similar to that of this example to improve the treatment effect and user experience.

Example 22

Fmoc-Lys(Mtt)-OH (250 mg, 400 µmole), DEPBT (120 mg, 400 µmole), DIPEA (140 µL, 800 µmole) were added to PEG20K—(NH$_2$)$_4$ (2 g, 100 µmole) in dichloromethane (25 mL). The reaction was stirred for 6 hours at room temperature, and acetic anhydride (50 µL, 526 µmole) was then added. Stirring continued for 10 minutes. The reaction solution was concentrated to 10 mL. MTBE (80 mL) was added and stirred for 10 minutes. The solid precipitate was filtered and dried in vacuo for the next reaction.

[Fmoc-Lys(Mtt)-NH]$_4$-PEG20K (2.02 g, 90 µmole) was dissolved in DMF (15 mL), and piperidine (1 mL, 10 mmol) was added. The reaction was stirred at room temperature for 15 min, and then MTBE (80 mL) was added. The product [H-Lys(Mtt)-NH]$_4$-PEG20K (1.76 g, 91%) was obtained after filtration.

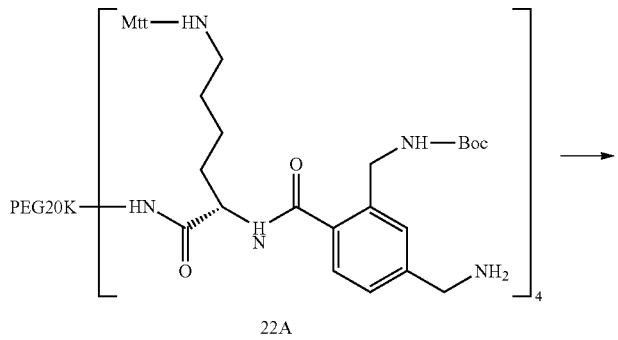

22A

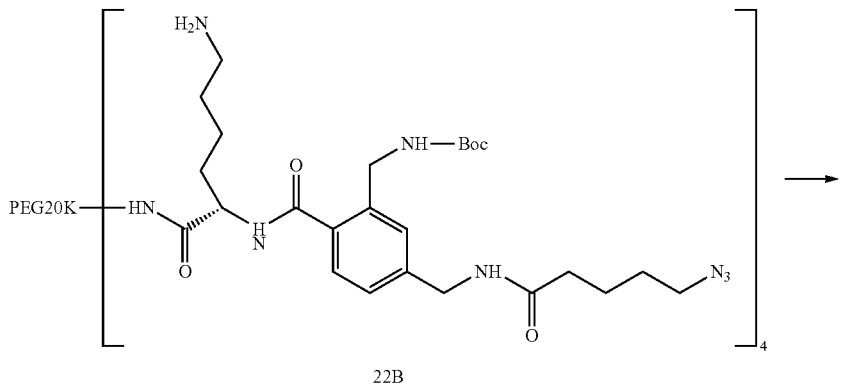

22B

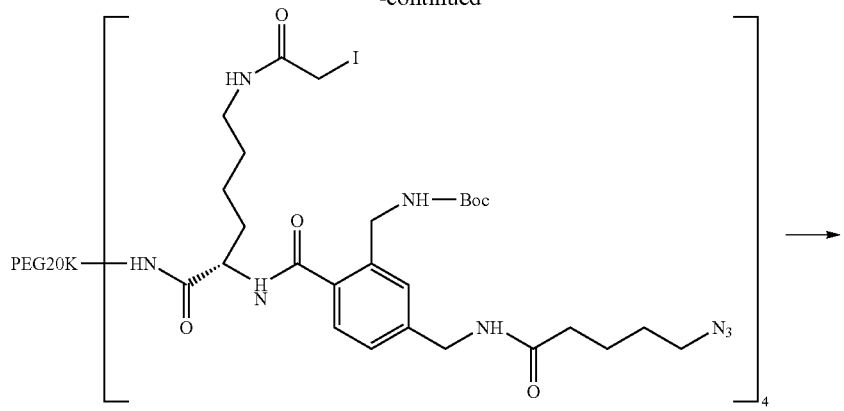

22C

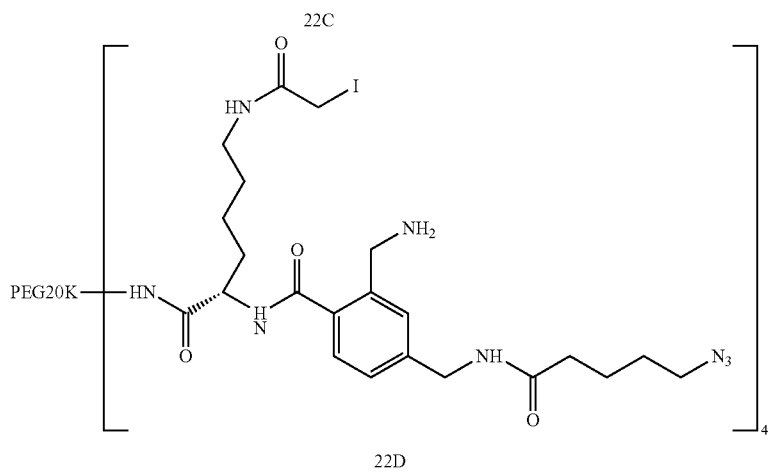

22D 11 (176 mg, 350 μmole), DEPBT (105 mg, 350 mole) and DIEA (61 μL, 360 μmole) were added to [H-Lys(Mtt)-NH] 4-PEG20K (1.76 g, 82 μmole) in DMF (15 mL). The reaction was stirred at room temperature for 6 hour. The solvent was removed under reduced pressure. 50% piperidine/DMF (10 mL) was added and stirred for 15 minutes. The solvent was removed under reduced pressure, and the residue was purified by HPLC to give 22A (1.59 g).

5-azidopentanoic acid (50 mg, 350 μmole), DEPBT (105 mg, 350 μmole) and DIEA (61 μL, 350 μmole) were added to 22A (1.59 g) in DMF (15 mL). The reaction was stirred at room temperature for 8 hours. After most of the solvent was removed under reduced pressure, MTBE (50 mL) was added and stirred for 10 minutes. The solid precipitate was filtered, dissolved in 1% TFA/CH$_2$Cl$_2$ (10 mL), and stirred for 30 minutes. The solution was concentrated to 5 mL, and MTBE (30 mL) was added. The mixture was stirred for 10 minutes. The solid precipitate was filtered and dried in vacuo to give 22B (1.24 g), which was used directly in the next reaction.

Iodoacetic acid (60 mg, 320 μmole), DEPBT (96 mg, 320 μmole) and DIEA (56 μL, 320 μmole) were added to 22B (1.14 g) in DMF (12 mL). The reaction was stirred at room temperature overnight. MTBE (100 mL) was added and stirred for 10 minutes. The solid precipitate was filtered and dried in vacuo to give 22C (1.03 g), which was used directly in the next reaction. 22C (1 g) was dissolved in CH$_2$Cl$_2$ (4 mL), and TFA (2 mL) was added. The reaction was stirred at room temperature for 10 min, and MTBE (20 mL) was added. The precipitate was filtered and purified by HPLC to give 22E (0.9 g) as a white powder.

Example 23

22E (100 mg) was added to PEG40K(NHC(O)CH$_2$I)$_4$ (DBCO)$_4$ (200 mg) of Example 2 in PBS (6 mL), mixed, and allowed to stand for 6 hours. The supernatant was removed, and the product was washed successively with purified water (10 mL), ethanol (10 mL) and acetonitrile (10 mL), and dried in vacuo to give hydrogel 23A.

22B (100 mg) was dissolved in 50% TFA/CH$_2$Cl$_2$ (1 mL) and stirred for 15 minutes at room temperature. The solvent was removed under reduced pressure, and the residue was dissolved in dichloromethane (1 mL). MTBE (6 mL) was added and stirred for 10 minutes. The solid precipitate was filtered, and PEG40K(NHC(O)CH$_2$I)$_4$ (DBCO)$_4$ (200 mg) in PBS (6 mL) was added and allowed to stand for 6 hours after mixing. The supernatant was removed, and the product was washed successively with purified water (10 mL), ethanol (10 mL) and acetonitrile (10 mL), and dried in vacuo to give hydrogel 23B.

Example 24

The hydrogel 23A (20 mg) obtained in Example 23 was suspended in PBS, and 8A (20 mg) was added. The reaction continued overnight. The supernatant was removed and the product was washed with PBS (2×3 mL) to give an insulin-containing hydrogel 23A-insulin. Hydrogel 23B (20 mg)

was suspended in PBS, and 8A (20 mg) was added. The reaction continued overnight. The supernatant was removed and the product was washed with PBS (2×3 mL), to give an insulin-containing hydrogel 23B-insulin.

To measure the insulin loading of the hydrogels, 23A-insulin and 238-insulin were incubated in a water bath at pH 10 to completely release insulin from the hydrogels. The insulin content in the sample was calculated by comparing the area of the insulin peak in the HPLC with the area of the known precisely quantified insulin standard under the same system. 23A released 10.5 mg of insulin and 23B released 4.7 mg. It was demonstrated that increasing the number of reactive functional groups on the crosslinking moiety of hydrogel can effectively increase the drug loading of the hydrogel.

Example 25

Hyaluronic acid (MW: 100K, 200 mg) was dissolved in 0.1M MES buffer solution (100 mL). EDC (144 mg, 0.75 mmole) and N-hydroxysuccinimide (86 mg, 0.75 mmole) were added and stirred for 30 minutes. N-(2-aminoethyl) maleimide hydrochloride (110 mg, 0.63 mmole) was dissolved in 0.1M MES buffer (40 mL) and was added to hyaluronic acid reaction. After 4 hours, the reaction mixture was washed with 20 nM sodium chloride solution and deionized water, dialyzed and lyophilized to give a white foamy solid. $^1$H-NMR ($D_2O$) spectrum of hyaluronic acid—maleimide showed a 67.0 peak, corresponding to the vinyl protons of the maleimide. Degree of substitution of hyaluronic acid—maleimide is defined as the number of maleimides per 100 hyaluronic acid disaccharide rings, by comparison of 62.0 and 67.0 peaks corresponding to acetamide methyl protons of hyaluronic acid and maleimide vinyl protons. The degree of substitution of the above reaction was 8. Reducing the ratio of N-(2-aminoethyl) maleimide to hyaluronic acid in the reaction can reduce the degree of substitution.

Hyaluronic acid-maleimide and PEG10K—(SH)$_4$ were dissolved in PBS, 1-3% w/v, the ratio of thiol to maleimide 1.1. As the concentration increased, gelation time decreased. When the degree of substitution was 4, 1% w/v gelation time was 40 s, 3% w/v the gelation time was 15 s. As the degree of substitution increased, the gelation time also decreased. When the degree of substitution was 8, 3% w/v gelation time was 7 s.

Hyaluronic acid-maleimide, PEG10K—(SH)$_4$ and 8A were dissolved in PBS, maleimide:thiol group of PEG: thiol group of 8A ratio 1:0.8:0.3, 1% w/v, mixed and stood for 1 hour to give hyaluronic acid—maleimide –8A, which can be used for subcutaneous injection.

Example 26

9-week-old male Wistar rats, average weight 240±10 g, were housed in polypropylene cages and maintained at constant temperature and humidity on a 12 hour light/dark cycle, and allowed access to food and water ad libitum. When diabetes was induced, rats were fasted for 48 hours and intraperitoneally injected with streptozotocin (60 mg/kg, dissolved in nM sodium citrate buffer, pH 4.5), then food was provided. Blood glucose was checked after three days. Animals with blood glucose above 250 mg/dl was considered diabetic, and the rats with blood glucose higher than 450 mg/dl were used in the experiment. Recombinant insulin (24 nmol/kg) was injected daily to maintain blood glucose no higher than 550 mg/dl.

The insulin hydrogels were prepared according to the methods in Examples 8 and 20, but the hydrogel used in this example was loaded only with insulin. The actual insulin content was calculated with the method in Example 18.

Rats showing hyperglycemia (400-450 mg/dl) were divided into 3 groups, each containing 8 rats. Rats in the first group were intraperitoneally injected saline (100 μL). Rats in the second group were intraperitoneal injected insulin detemir (40 nmol/kg) daily. Rats in the third group were Injected hydrogel (75 nmol/kg, calculated according to the actual amount of human insulin in the hydrogel). Another group of 8 healthy rats were intraperitoneally injected saline (100 μL) as the control. The result is shown in FIG. 1.

Insulin detemir is a representative long-acting insulin used clinically as a daily injection. Insulin hydrogel is subcutaneously injected and its hypoglycemic effect lasts for at least a week. Insulin detemir utilizes a fatty acid for long action and its biological activity is reduced, so a dose of 40 nmol/kg cannot effectively lower blood glucose. Insulin released from the insulin hydrogel retains its full activity, lowering blood glucose near normal values at a lower dose than insulin detemir. In addition, the insulin hydrogel is not like many other hydrogels, which show "burst release" phenomenon at an early stage or cause hypoglycemia by excessive insulin. The blood glucose of animals in the insulin hydrogel group was basically stable in 1-7 days, indicating that insulin was released at a constant rate. This example illustrates that the hydrogel of the present invention can be an effective long-acting drug delivery technology.

The invention claimed is:

1. A hydrogel, which is biodegradable under physiological conditions, wherein the hydrogel comprises moieties which are biodegradable under physiological conditions and have the formula

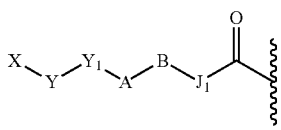

wherein X is OH or —HN—$R_0$;

Y is selected from the group consisting of:
(1) $NR_0$;
(2) $C(R_pR_q)$;
(3) O, with the proviso that X is not OH; and
(4) $C(R_pR_q)$, when X is —HN—$R_0$, $R_0$ and $R_p$ together with the atoms attached form a 4, 5 or 6-membered heterocyclic ring;

$Y_1$ is selected from the group consisting of:
(1) $C(R_3R_4)$;
(2) C(O) or C(S), with the proviso that A is not C(O), C(S), SO, and $SO_2$;
(3) O, S, SO or $SO_2$, with the proviso that A and Y are not O;
(4) —$NR_n$; and
(5) a bond;

$J_1$ is C ($R_{10}R_{11}$) or a covalent bond;
the wavy line indicates an attachment point;

A and B together form a ring system selected from the group consisting of an aryl having from 6 to 15 carbon atoms; a cycloalkyl having a 3, 4, 5, 6, 7, 8, 9, or 10 membered ring; a cycloalkenyl having a 4, 5, 6, 7, 8, 9, or 10 membered ring; a cycloalkynyl having a 5, 6, 7, 8, 9, or membered ring; a saturated or unsaturated monocyclic, polycyclic or fused cyclic; an unsaturated monoheterocyclic; a saturated or unsaturated polyheterocyclic; and a saturated or unsaturated fused heterocyclic, containing one or more heteroatoms N, S or O in each heterocyclic ring thereof and each ring being from 3- to 10-membered;

each of aforementioned ring is optionally substituted with one or more groups selected from the group consisting of alkyl, alkoxy, acyl, acyloxy, alkoxycarbonyl, aryl, phenyl, benzyl, halo, haloformyl, haloalkyl, trifluoromethyl, trifluoromethoxy, trichloromethyl, cyanato, isocyano, isocyanate ester, isocyanate salt, isothiocyanate, thiocyanate ester, thiocyanate salt, alkylthio, amino, imino, amino alkyl, alkylamino, dialkylamino, hydroxyl, hydroxyl alkyl, nitro, nitrile, isonitrile, pyridyl, azido, carboxyl, carboxamido, acetic acid, thiolalkyl, carbonate ester, carbonate salt, carbamate, alkylcarbamyl, dialkylcarbamyl, sulfonic acid, sulfonamide, sulfonate ester, sulfonate salt, sulfonyl, sulfoxide, sulfide, disulfide, and mercapto;

or A and B together with the atoms to which they are attached form an aromatic ring or a heteroaromatic ring optionally substituted by at least one group defined above; or A and B together with the atoms to which they are attached form a polyaromatic ring or a polyheteroaromatic ring optionally substituted by at least one group defined above;

Y, A, or B contains at least one reactive group which can form a covalent bond with a reactive polymer to connect to one or more reactive polymers;

$R_0$, $R_O$, $R_3$, $R_4$, $R_{10}$, $R_{11}$, $R_n$, $R_p$, and $R_q$ are independently selected from the group consisting of hydrogen, alkyl, alkoxy, acyl, acyloxy, alkoxycarbonyl, aryl, phenyl, benzyl, halo, haloformyl, haloalkyl, trifluoromethyl, trifluoromethoxy, trichloromethyl, cyanato, isocyano, isocyanate ester, isocyanate salt, isothiocyanate, thiocyanate ester, thiocyanate salt, alkylthio, amino, imino, amino alkyl, alkylamino, dialkylamino, hydroxyl, hydroxyl alkyl, nitro, nitrile, isonitrile, pyridyl, azido, carboxyl, carboxamido, acetic acid, thiolalkyl, carbonate ester, carbonate salt, carbamate, alkylcarbamyl, dialkylcarbamyl, sulfonic acid, sulfonamide, sulfonate ester, sulfonate salt, sulfonyl, sulfoxide, sulfide, disulfide, and mercapto;

or $R_0$, $R_O$, $R_3$, $R_4$, $R_{10}$, $R_{11}$, $R_n$, $R_p$, and $R_q$ are independently selected from the group consisting of $-SO_2-OH$, $-SO_2-NR_{m1}R_{m2}$, $-SO_2-R_{m3}$, $-O-R_{m4}$, $-S-R_{m5}$, $-N-R_{m6}R_{m7}$, $-C(O)R_{m8}$, $-C(O)OR_{m9}$, $-OC(O)R_{m10}$, $-NHC(O)R_{m11}$, $-C(O)NR_{m12}R_{m13}$, and $-NHC(O)NR_{m14}R_{m15}$, wherein $R_{m1}$, $R_{m2}$, $R_{m3}$, $R_{m4}$, $R_{m5}$, $R_{m6}$, $R_{m7}$, $R_{m8}$, $R_{m9}$, $R_{m10}$, $R_{m11}$, $R_{m12}$, $R_{m13}$, $R_{m14}$, and $R_{m15}$ are independently selected from hydrogen (H), $(C_1-C_{18})$ alkyl, aryl, $(C_1-C_{18}$ alkyl)OH, $(C_1-C_{18}$ alkyl)SH, $(C_1-C_{18}$ alkyl)COOH, $(C_1-C_{18}$ alkyl)NH$_2$, $(C_0-C_4$ alkyl)$(C_5-C_6$ cycloalkyl), $(C_0-C_{10}$ alkyl)$(C_5-C_6$ heterocyclic), $(C_0-C_4$ alkyl)$(C_6-C_{10}$ aryl), and $(C_0-C_4$ alkyl)$(C_4-C_9$ heteroaryl);

or $R_p$ and $R_q$ are independently selected from the group consisting of $(C_1-C_{20})$ alkyl, $(C_1-C_{10}$ alkyl)OH, $(C_1-C_{10}$ alkyl)SH, $(C_2-C_3$ alkyl)SCH$_3$, $(C_1-C_4$ alkyl)CONH$_2$, $(C_1-C_{10}$ alkyl)COOH, $(C_1-C_{10}$ alkyl)NH$_2$, $(C_1-C_4$ alkyl)NHC(NH$_2^+$)NH$_2$, $(C_0-C_4$ alkyl)$(C_3-C_6$ cycloalkyl), $(C_0-C_4$ alkyl)$(C_2-C_5$ heterocyclic), $(C_0-C_4$ alkyl)$(C_6-C_{10}$ aryl), $(C_0-C_4$ alkyl)$(C_6-C_{10}$ aryl)$R_{16}$, $(C_1-C_4$ alkyl)$(C_3-C_9$ heteroaryl), and $C_1-C_{12}$ alkyl$(W_1)C_1-C_{12}$ alkyl, wherein $W_1$ is a heteroatom selected from N, S and O; $R_{16}$ is selected from H, OH, halo, $C_1-C_7$ alkyl, $C_2-C_7$ alkenyl, $C_2-C_7$ alkynyl, $CO_2H$, $CO_2(C_1-C_7$ alkyl), NH($C_0-C_{10}$ alkyl), O($C_1-C_{10}$ alkyl), aryl, and heteroaryl.

2. The hydrogel according to claim 1, wherein the hydrogel comprises a backbone comprising homopolymers of a substance selected from the group consisting of polyethylene glycol, polypropylene glycol, poly(N-vinylpyrrolidone), polymethylacrylate, polyphosphazene, polylactide, polyacrylamide, polyglycolic acid, polyethylene imine, agarose, dextran, gelatin, collagen, polylysine, chitosan, alginates, hyaluronic acid, pectin, carrageenan, and polyamino acids, which have suitable reactive functional groups and crosslinkable functional groups in the natural state, or are derivatized to have suitable reactive functional groups and crosslinkable functional groups; or copolymers of two or more substances selected from the group consisting of polyethylene glycol, polypropylene glycol, poly(N-vinylpyrrolidone), polymethylacrylate, polyphosphazene, polylactide, polyacrylamide, polyglycolic acid, polyethylene imine, agarose, dextran, gelatin, collagen, polylysine, chitosan, alginates, hyaluronic acid, pectin, carrageenan, and polyamino acids, which have suitable reactive functional groups and crosslinkable functional groups in the natural state, or are derivatized to have suitable reactive functional groups and crosslinkable functional groups.

3. The hydrogel according to claim 2, wherein the backbone comprises a moiety of the formula $J(L_1-B_1)_{n1}$, wherein J is a branching core; $L_1$ is a chain extending therefrom; $B_1$ has at least one crosslinkable functional group and at least one optional reactive functional group; said at least one optional reactive functional group and said at least one crosslinkable functional group are identical or different; the at least one crosslinkable functional group and the at least one optional reactive functional group on the same backbone moiety cannot react with one another; and n1 is an integer of 2-32.

4. The hydrogel according to claim 3, wherein $L_1$ is a PEG-based polymeric chain; each $L_1$ is independently $-(CH_2)_{n4}(OCH_2CH_2)_nL_{n5}$ or $(CH_2)_{n4}(CH_2CH_2O)_nL_{n5}$, wherein n4 is an integer of 0-5, n is an integer from 1 to 1000, and $L_{15}$ is a chemical bond or a functional group connecting ends of $L_1$ and $B_1$.

5. The hydrogel according to claim 2, wherein the backbone comprises a moiety of the formula $(C_1-L_1)_{n2}J(L_1-C_2)_{n3}$, wherein J is a branching core; $L_1$ is a chain extending therefrom; $C_1$ is a reactive functional group, $C_2$ is a crosslinkable functional group; said reactive functional group and said crosslinkable functional group are identical or different; the crosslinkable functional group and reactive functional group on the same backbone moiety cannot react with each other; and n2 and n3 are an integer of 1-32.

6. The hydrogel according to claim 5, wherein n2 is 4, and n3 is 4.

7. The hydrogel according to claim 1, wherein the hydrogel comprises a crosslinking moiety of a formula $B_2-Z_2-L_2-Z_2-B_2$, $B_2-Z_2-L_2-B_2$, $B_2-Z_2-L_2-Z_2'-B_2$, or $B_2-Z_2-L_2-Z_2-B_2'$, wherein $L_2$ is a chain connecting both ends; $B_2$, and $B_2$ each has at least one crosslinkable functional group and at least one optional reactive functional group; $Z_2$ and $Z_2'$ are optional biodegradable linkers, $B_2$ and $B_2'$, $Z_2$ and $Z_2'$ are identical or different; and said at least one crosslinkable functional group and said at least one optional reactive functional group on the same crosslinking moiety cannot react with one another.

8. The hydrogel according to claim 7, wherein $B_2$ or $B_2'$ in the crosslinking moiety comprises one or more optional biodegradable linkers in its branched structure, and the at least one crosslinkable functional groups and the at least one optional reactive functional groups of $B_2$ and $B_2'$ are respectively connected to optional biodegradable linkers.

9. The hydrogel according to claim 1, wherein the hydrogel comprises a crosslinking moiety of a formula $O(L_2-Z_2-B_2)_{n6}$, wherein O is a branching core, $L_2$ is a chain extending therefrom, n6 is an integer of 2-16, $Z_2$ is an optional biodegradable linker; $B_2$ has at least one crosslinkable functional group and at least one optional reactive functional group; and the at least one crosslinkable functional group and the at least one optional reactive functional group are connected to $B_2$ via an optional biodegradable linker.

10. The hydrogel according to claim 9, wherein $L_2$ of the crosslinking moiety is a PEG-based polymeric chain, two ends of which are connected to $B_2$ and the branching core respectively by covalent bonds; each $L_2$ is independently selected from the formulae —$(CH_2)_{n4}(OCH_2CH_2)_nL_{n5}$ and —$(CH_2)_{n4}(CH_2CH_2O)_n L_{n5}$, wherein n4 is an integer of 0-5, n is an integer from 1 to 1000, and $L_{n5}$ is a chemical bond or a functional group connecting end of $L_2$ and $Z_2$.

11. The hydrogel according to claim 9, wherein the crosslinking moiety has the formula $O(L_2-B_2)_{n6}$, wherein $B_2$ has at least one crosslinkable functional group and at least one optional reactive functional group; and said at least one crosslinkable functional group and said at least one optional reactive functional group are connected to optional biodegradable linkers respectively.

12. The hydrogel according to claim 1, wherein the moieties have the formula:

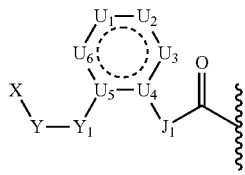

wherein $U_1$, $U_2$, $U_3$, $U_4$, $U_5$ and $U_6$ are independently $CR_{12}$ or N;
X is OH or —HN—$R_O$;
Y is selected from the group consisting of:
(1) $NR_O$;
(2) $C(R_pR_q)$;
(3) O, with the proviso that X is not OH; and
(4) $C(R_pR_q)$, when X is —HN—$R_O$, $R_O$ and $R_p$ together with the atoms attached form a 4, 5 or 6-membered heterocyclic ring;
$Y_1$ is selected from the group consisting of:
(1) $C(R_3R_4)$;
(2) C(O) or C(S), with the proviso that A is not C(O), C(S), SO, and $SO_2$;
(3) O, S, SO or $SO_2$, with the proviso that A and Y are not O;
(4) —$NR_n$; and
(5) a bond;
$J_1$ is C $(R_{10}R_{11})$ or a covalent bond;
$R_{12}$ is selected from the group consisting of hydrogen, alkyl, alkoxy, acyl, acyloxy, alkoxycarbonyl, aryl, phenyl, benzyl, halo, haloformyl, haloalkyl, trifluoromethyl, trifluoromethoxy, trichloromethyl, cyanato, isocyano, isocyanate ester, isocyanate salt, isothiocyanate, thiocyanate ester, thiocyanate salt, alkylthio, amino, imino, amino alkyl, alkylamino, dialkylamino, hydroxyl, hydroxyl alkyl, nitro, nitrile, isonitrile, pyridyl, azido, carboxyl, carboxamido, acetic acid, thiolalkyl, carbonate ester, carbonate salt, carbamate, alkylcarbamyl, dialkylcarbamyl, sulfonic acid, sulfonamide, sulfonate ester, sulfonate salt, sulfonyl, sulfoxide, sulfide, disulfide, and mercapto;
or $R_{12}$ is selected from the group consisting of —$SO_2$—OH, —$SO_2$—$NR_{m1}R_{m2}$, —$SO_2$—$R_{m3}$, —O—$R_{m4}$, —S—$R_{m5}$, —N—$R_{m6}R_{m7}$, —$C(O)R_{m8}$, —$C(O)OR_{m9}$, —$OC(O)R_{m10}$, —$NHC(O)R_{m11}$, —$C(O)NR_{m12}R_{m13}$, and —$NHC(O)NR_{m14}R_{m15}$, wherein $R_{m1}$, $R_{m2}$, $R_{m3}$, $R_{m4}$, $R_{m5}$, $R_{m6}$, $R_{m7}$, $R_{m8}$, $R_{m9}$, $R_{m10}$, $R_{m11}$, $R_{m12}$, $R_{m13}$, $R_{m14}$, and $R_{m15}$ are independently selected from hydrogen (H), ($C_1$-$C_{18}$) alkyl, aryl, ($C_1$-$C_{18}$ alkyl)OH, ($C_1$-$C_{18}$ alkyl)SH, ($C_1$-$C_{18}$ alkyl)COOH, ($C_1$-$C_{18}$ alkyl)$NH_2$, ($C_0$-$C_4$ alkyl)($C_5$-$C_6$ cycloalkyl), ($C_0$-$C_{10}$ alkyl)($C_5$-$C_6$ heterocyclic), ($C_0$-$C_4$ alkyl)($C_6$-$C_{10}$ aryl), and ($C_0$-$C_4$ alkyl)($C_4$-$C_9$ heteroaryl).

13. The hydrogel according to claim 12, wherein the moieties have the formula:

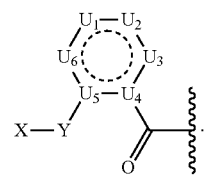

14. A drug delivery hydrogel, comprising the hydrogel according to claim 1 and a biologically active substance loaded into the hydrogel by non-covalent encapsulation or connected to the hydrogel by a covalent bond.

15. The drug delivery hydrogel according to claim 14, characterized in that the biologically active substance is connected to a biodegradable linker which is attached to the hydrogel covalently.

16. The drug delivery hydrogel according to claim 14, wherein the biologically active substance and one of the moieties together have the formula

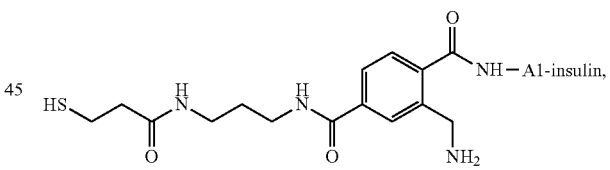

which is conjugated to a remaining portion of the drug delivery hydrogel via the thiol group.

17. The drug delivery hydrogel according to claim 14, wherein the biologically active substance and one of the moieties together have the formula (SEQ ID NO: 1)

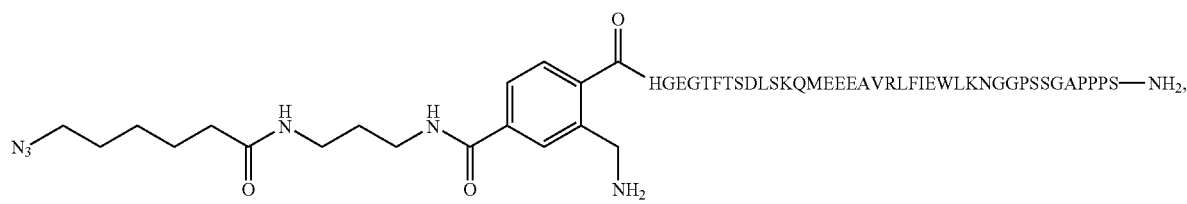

which is conjugated to a remaining portion of the drug delivery hydrogel via the azide group.

18. The hydrogel according to claim 1, wherein the moieties have the formula:

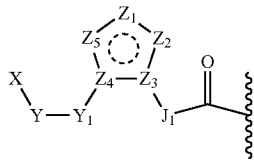

wherein $Z_1$, $Z_2$, $Z_3$, $Z_4$, and $Z_5$ are independently selected from the group consisting of $CR_{12}$, N, $NR_{13}$, O, and S;
X is OH or HN—$R_O$;
Y is selected from the group consisting of
(1) N—$R_O$;
(2) $C(R_pR_q)$;
(3) O, with the proviso that X is not OH; and
(4) $C(R_pR_q)$, when X is HN—$R_O$, $R_O$ and $R_p$ together with the atoms to which they are attached can form a 4, 5, or 6 membered heterocyclic ring;
$Y_1$ is selected from the group consisting of
(1) $C(R_3R_4)$;
(2) C(O) or C(S), with the proviso that Y and A are not C(O), C(S), SO, and $SO_2$;
(3) O, S, SO, or $SO_2$, with the proviso that Y and A are not O;
(4) N—$R_n$; and
(5) a covalent bond;
$J_1$ is $C(R_{10}R_{11})$ or a covalent bond; and
$R_{12}$ is selected from the group consisting of hydrogen, alkyl, alkoxy, acyl, acyloxy, alkoxycarbonyl, aryl, phenyl, benzyl, halo, haloformyl, haloalkyl, trifluoromethyl, trifluoromethoxy, trichloromethyl, cyanato, isocyano, isocyanate ester, isocyanate salt, isothiocyanate, thiocyanate ester, thiocyanate salt, alkylthio, amino, imino, amino alkyl, alkylamino, dialkylamino, hydroxyl, hydroxyl alkyl, nitro, nitrile, isonitrile, pyridyl, azido, carboxyl, carboxamido, acetic acid, thiolalkyl, carbonate ester, carbonate salt, carbamate, alkylcarbamyl, dialkylcarbamyl, sulfonic acid, sulfonamide, sulfonate ester, sulfonate salt, sulfonyl, sulfoxide, sulfide, disulfide, and mercapto;
or $R_{12}$ is selected from the group consisting of —$SO_2$—OH, —$SO_2$—$NR_{m1}R_{m2}$, —$SO_2$—$R_{m3}$, —O—$R_{m4}$, —S—$R_{m5}$, —N—$R_{m6}R_{m7}$, —C(O)$R_{m8}$, —C(O)O$R_{m9}$, —OC(O)$R_{m10}$, —NHC(O)$R_{m11}$, —C(O)N$R_{m12}R_{m13}$, and —NHC(O)N$R_{m14}R_{m15}$, wherein $R_{m1}$, $R_{m2}$, $R_{m3}$, $R_{m4}$, $R_{m5}$, $R_{m6}$, $R_{m7}$, $R_{m8}$, $R_{m9}$, $R_{m10}$, $R_{m11}$, $R_{m12}$, $R_{m13}$, $R_{m14}$, and $R_{m15}$ are independently selected from hydrogen (H), ($C_1$-$C_{18}$) alkyl, aryl, ($C_1$-$C_{18}$ alkyl)OH, ($C_1$-$C_{18}$ alkyl)SH, ($C_1$-$C_{18}$ alkyl)COOH, ($C_1$-$C_{18}$ alkyl)$NH_2$, ($C_0$-$C_4$ alkyl)($C_5$-$C_6$ cycloalkyl), ($C_0$-$C_{10}$ alkyl)($C_5$-$C_6$ heterocyclic), ($C_0$-$C_4$ alkyl)($C_6$-$C_{10}$ aryl), and ($C_0$-$C_4$ alkyl)($C_4$-$C_9$ heteroaryl);
$R_{13}$ is selected from the group consisting of hydrogen, alkyl, alkoxy, acyl, acyloxy, alkoxycarbonyl, aryl, phenyl, benzyl, halo, haloformyl, haloalkyl, trifluoromethyl, trifluoromethoxy, trichloromethyl, cyanato, isocyano, isocyanate ester, isocyanate salt, isothiocyanate, thiocyanate ester, thiocyanate salt, alkylthio, amino, imino, amino alkyl, alkylamino, dialkylamino, hydroxyl, hydroxyl alkyl, nitro, nitrile, isonitrile, pyridyl, azido, carboxyl, carboxamido, acetic acid, thiolalkyl, carbonate ester, carbonate salt, carbamate, alkylcarbamyl, dialkylcarbamyl, sulfonic acid, sulfonamide, sulfonate ester, sulfonate salt, sulfonyl, sulfoxide, sulfide, disulfide, and mercapto;
or $R_{13}$ is selected from —$SO_2$—OH, —$SO_2$—$NR_{m1}R_{m2}$, —$SO_2$—$R_{m3}$, —O—$R_{m4}$, —S—$R_{m5}$, —N—$R_{m6}R_{m7}$, —C(O)$R_{m8}$, —C(O)O$R_{m9}$, —OC(O)$R_{m10}$, —NHC(O)$R_{m11}$, —C(O)N$R_{m12}R_{m13}$, and —NHC(O)N$R_{m14}R_{m15}$, wherein $R_{m1}$, $R_{m2}$, $R_{m3}$, $R_{m4}$, $R_{m5}$, $R_{m6}$, $R_{m7}$, $R_{m8}$, $R_{m9}$, $R_{m10}$, $R_{m11}$, $R_{m12}$, $R_{m13}$, $R_{m14}$, and $R_{m15}$ are independently selected from hydrogen (H), ($C_1$-$C_{18}$) alkyl, aryl, ($C_1$-$C_{18}$ alkyl)OH, ($C_1$-$C_{18}$ alkyl)SH, ($C_1$-$C_{18}$ alkyl)COOH, ($C_1$-$C_{18}$ alkyl)$NH_2$, ($C_0$-$C_4$ alkyl)($C_5$-$C_6$ cycloalkyl), ($C_0$-$C_{10}$ alkyl)($C_5$-$C_6$ heterocyclic), ($C_0$-$C_4$ alkyl)($C_6$-$C_{10}$ aryl), and ($C_0$-$C_4$ alkyl)($C_4$-$C_9$ heteroaryl).

19. The hydrogel according to claim 1, wherein the moieties have the formula:

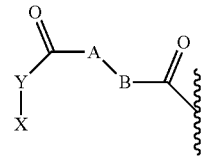

wherein X is OH or HN—$R_O$; and
Y is selected from the group consisting of:
(1) N—$R_O$;
(2) $C(R_pR_q)$;
(3) O, with the proviso that X is not OH; and
(4) $C(R_pR_q)$, when X is HN—$R_O$, $R_O$ and $R_p$ together with the atoms to which they are attached form a 4, 5, or 6-membered heterocyclic ring.

* * * * *

SEQUENCE LISTING

```
<160> NUMBER OF SEQ ID NOS: 4

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30
```

```
Ser Gly Ala Pro Pro Pro Ser
        35

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Gly Ile Val Glu Gln Ala Ala Tyr
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3

Gly Ile Val Glu Gln Ala Ala
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Gly Ile Val Glu Gln Ala Ala
1               5
```